(12) United States Patent
Narine et al.

(10) Patent No.: US 10,000,601 B2
(45) Date of Patent: *Jun. 19, 2018

(54) METATHESIZED TRIACYLGLYCEROL POLYOLS FOR USE IN POLYURETHANE APPLICATIONS AND THEIR RELATED PROPERTIES

(71) Applicant: Trent University, Peterborough (CA)

(72) Inventors: Suresh Narine, Peterborough (CA); Prasanth Kumar Sasidharan Pillai, Peterborough (CA); Shaojun Li, Peterborough (CA); Laziz Bouzidi, Peterborough (CA); Ali Mahdevari, Peterborough (CA)

(73) Assignee: Trent University, Peterborough, Ontario (CA)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/670,028

(22) Filed: Mar. 26, 2015

(65) Prior Publication Data

US 2015/0337073 A1 Nov. 26, 2015

Related U.S. Application Data

(60) Provisional application No. 61/971,475, filed on Mar. 27, 2014.

(51) Int. Cl.
| | |
|---|---|
| *C08G 18/36* | (2006.01) |
| *C07C 69/675* | (2006.01) |
| *C07C 69/34* | (2006.01) |
| *C11C 3/00* | (2006.01) |
| *C08L 75/06* | (2006.01) |
| *C08L 83/06* | (2006.01) |
| *C08G 18/66* | (2006.01) |
| *C08G 101/00* | (2006.01) |

(52) U.S. Cl.
CPC ............. *C08G 18/36* (2013.01); *C07C 69/34* (2013.01); *C07C 69/675* (2013.01); *C08G 18/6696* (2013.01); *C08L 75/06* (2013.01); *C08L 83/06* (2013.01); *C11C 3/00* (2013.01); *C08G 2101/00* (2013.01); *C08G 2101/0008* (2013.01); *C08G 2101/0025* (2013.01); *C11C 3/006* (2013.01)

(58) Field of Classification Search
CPC ...................... C08G 18/36; C11C 3/006; B01J 2231/54–2231/543; C07C 69/675
See application file for complete search history.

(56) References Cited

U.S. PATENT DOCUMENTS

| | | | |
|---|---|---|---|
| 4,545,941 A | 10/1985 | Rosenburg | |
| 4,997,858 A * | 3/1991 | Jourquin | .................. C08J 9/142 |
| | | | 521/118 |
| 5,312,940 A | 5/1994 | Grubbs et al. | |
| 5,342,909 A | 8/1994 | Grubbs et al. | |
| 5,710,298 A | 1/1998 | Grubbs et al. | |
| 5,728,917 A | 3/1998 | Grubbs et al. | |
| 5,750,815 A | 5/1998 | Grubbs et al. | |
| 5,831,108 A | 11/1998 | Grubbs et al. | |
| 5,922,863 A | 7/1999 | Grubbs et al. | |
| 6,306,988 B1 | 10/2001 | Grubbs et al. | |
| 6,414,097 B1 | 7/2002 | Grubbs et al. | |
| 6,696,597 B2 | 2/2004 | Pederson et al. | |
| 6,794,534 B2 | 9/2004 | Grubbs et al. | |
| 7,102,047 B2 | 9/2006 | Grubbs et al. | |
| 7,378,528 B2 | 5/2008 | Herrmann et al. | |
| 7,745,652 B2 | 6/2010 | Lysenko et al. | |
| 2009/0264672 A1 | 10/2009 | Abraham et al. | |
| 2010/0145086 A1 | 6/2010 | Schrodi et al. | |
| 2010/0160506 A1 | 6/2010 | Wu et al. | |

FOREIGN PATENT DOCUMENTS

| | | | |
|---|---|---|---|
| WO | WO2007103398 | 9/2007 | |
| WO | WO2008048520 | 4/2008 | |
| WO | WO2009020667 | 8/2008 | |
| WO | WO2011133208 | 10/2011 | |
| WO | WO 2013192384 A1 * | 12/2013 | ............... C11C 3/00 |
| WO | WO2015143562 | 10/2015 | |
| WO | WO2015143563 | 10/2015 | |
| WO | WO2015143568 | 10/2015 | |

OTHER PUBLICATIONS

Zlatanic, A.; Petrovic, Z. S.; Dusek, K. Structure and properties of triolein-based polyurethane networks. Biomacromolecules, 2002, vol. 3, pp. 1048-1056.*

Desroches, M.; Escouvous, M.; Auvergne, R.; Caillol, S.; Boutevin, B. From vegetable oils to polyurethanes: synthetic routes to polyols and main industrial products. Polymer Reviews, 2012, vol. 52, pp. 38-79.*

Zhao, H-P; Zhang, J-F.; Sun, X. S.; Hua, D. H. Synthesis and properties of cross-linked polymers from functionalized triglycerides. Journal of Applied Polymer Science, 2008, vol. 110, pp. 647-565.*

Luong, T. M.; Schriftman, H.; Swern, D. Direct hydroxylation of fats and derivatives with a hydrogen peroxide tungstic acid system. Journal of the American Oil Chemists' Society, 1967, vol. 44, pp. 316-320.*

Damiani, P.; Burini, G. Determination of the triglyceride composition of olive oil by a multistep procedure. Journal of Agricultural and Food Chemistry, 1980, vol. 28, pp. 1232-1236.*

Scholnick, F.; Saggese, E. J.; Wrigley, A. N.; Ault, W. C.; Monroe Jr., H. A.; Zubillaga, M. Urethane foams from animal fats. IV. Rigid foams from epoxidized glycerides. Journal of the American Oil Chemists' Society, 1968, pp. 76-77.*

Dunkle, M. N.; David, F.; Sandra, P.; Vollmer, M. Analysis of triglycerides in vegetable oils using the Agilent 1260 Infinity Analytical SFC System with evaporative light scattering detection. Agilent Technologies. Aug. 1, 2015.*

(Continued)

*Primary Examiner* — Stephen E Rieth
(74) *Attorney, Agent, or Firm* — Bereskin & Parr LLP/S.E.N.C.R.L., s.r.l.; Michael Fenwick

(57) ABSTRACT

Metathesized triacylglycerol polyols and their related physical and thermal properties are disclosed. Such metathesized triacylglycerol polyols are also used as a component of polyurethane applications, including polyurethane foams.

19 Claims, 32 Drawing Sheets

(56) References Cited

OTHER PUBLICATIONS

Rouhi, A. M. Olefin Metathesis: Big-Deal Reaction. Chemical & Engineering News, 2002, vol. 80, No. 51, pp. 29-33.*

K.J. Ivin and J.C. Mol. Olefin Metathesis and Metathesis Polyermization. Survey of Catalyst Systems, Chapter 2, pp. 12-49, 1997.

J.C. Mol. Application of olefin metathesis in oleochemistry: an example of green chemistry. Green Chem. 4:5-13, 2002.

T. Gibson and L.Tulich. Novel Synthesis of Long-chain Primary Alkyl Compounds. J. Org. Chem. 46:1821-1823, 1981.

G. Doyle. Olefin Metatheesis Catalyzed by Zero-Valent, Anionic Group VI Metal Comounds. J. Catal. 30:118-127, 1973.

R. Spronk and J.C. Mol. Metathesis of 1-alkenes in the liquid phase over a Re2O7/gamma-Al2O3 caatalyst. Applied Catalysis 70:295-306, 1991.

Harold H. Fox, Richard R. Schrock,. and Rick O'Dell. Coupling of Terminal Olefins by Molybdenum(VI) Imido Alkylidene Complexes. Organometallics 13:635-639, 1994.

Igor Elkin and Patrice Hildgen. Selective synthesis of glyceryl tris[9,10-(threo)-dihydroxyoctadecanoate. Journal of the American Oil Chemists' Society, 2013, 90(10):1465-1474.

Lucas Montero De Espinosa, Juan C. Ronda, Marina Galia, Virginia Cadiz. Quinoline-Containing Networks from Enone and Aldehyde Triglyceride Derivatives. Journal of Polymer Science, Part A: Polymer Chemistry, 2010, 48(4): 869-878.

T. Gibson and L. Tulich. Novel Synthesis of Long-chain Primary Alkyl Compounds. J. Org. Chem. 46:1821-1823, 1981.

* cited by examiner

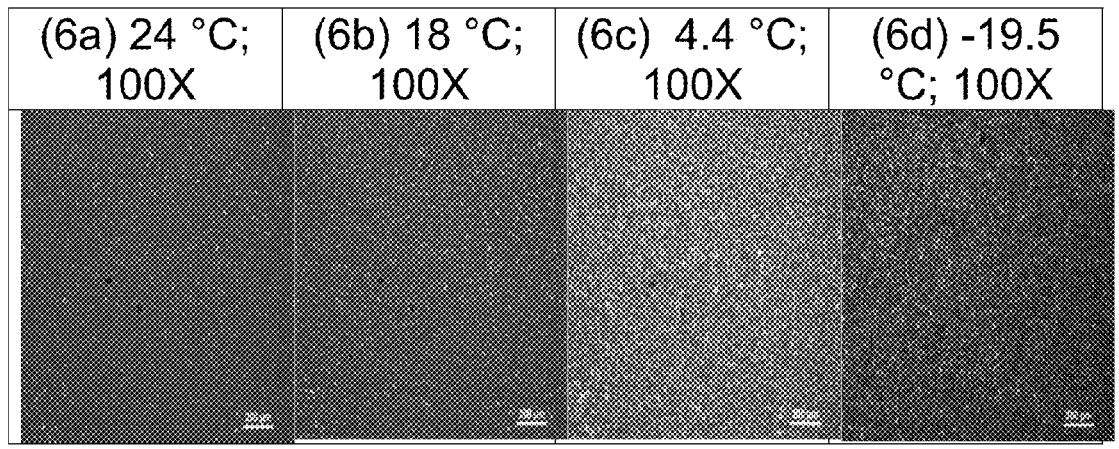
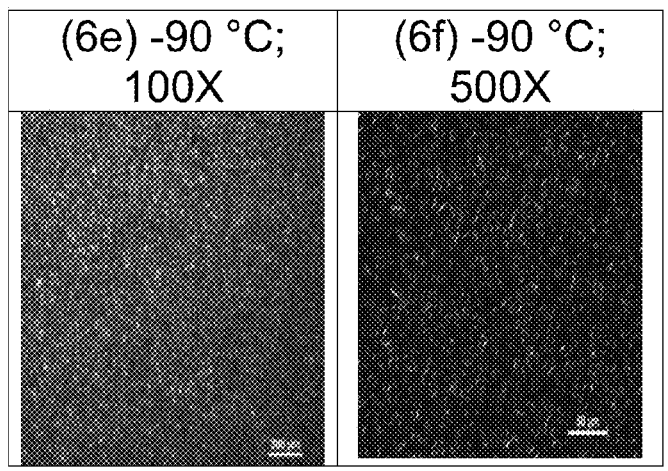
Figures 6a-f

METATHESIZED TRIACYLGLYCEROL POLYOLS FOR USE IN POLYURETHANE APPLICATIONS AND THEIR RELATED PROPERTIES

CROSS REFERENCE TO RELATED APPLICATIONS

A claim of priority for this application under 35 U.S.C. § 119(e) is hereby made to the following U.S. Provisional patent application: U.S. Ser. No. 61/971,475 filed Mar. 27, 2014; and this application is incorporated herein by reference in its entirety.

TECHNICAL FIELD

This application relates to metathesized triacylglycerol polyols and their related physical and thermal properties. Such metathesized triacylglycerol polyols are also used as a component of polyurethane applications, including polyurethane foams.

BACKGROUND

Polyurethanes are one of the most versatile polymeric materials with regards to both processing methods and mechanical properties. Polyurethanes are formed either based on the reaction of NCO groups and hydroxyl groups, or via non-isocyanate pathways, such as the reaction of cyclic carbonates with amines, self-polycondensation of hydroxyl-acyl azides or melt transurethane methods. The most common method of urethane production is via the reaction of a polyol and an isocyanate which forms the backbone urethane group. Cross-linking agents, chain extenders, blowing agents and other additives may also be added as needed. The proper selection of reactants enables a wide range of polyurethane elastomers, sheets, foams, and the like.

Traditionally, petroleum-derived polyols have been widely used in the manufacturing of polyurethane foams. However, there has been an increased interest in the use of renewable resources in the manufacturing of polyurethane foams. This has led to research into developing natural oil-based polyols for use in the manufacturing of foams. The present effort details the synthesis of natural oil based metathesized triacylglycerols (MTAG), and in particular, palm oil based metathesized triacylglycerols (PMTAG), and polyols thereof. Any polyols derived from such metathesized triacylglycerols may be utilized in polyurethane applications, such as rigid and flexible polyurethane foams. The present effort also discloses physical and thermal properties of such polyols, and the formulation of polyurethane foams using such polyols as a component.

BRIEF DESCRIPTION OF THE DRAWINGS

FIGS. 6a, 6b, 6c, and 6d depict microstructure (100×) development of the PMTAG during cooling (5° C.) from the melt.

FIGS. 6e and 6f depict the final microstructure of the PMTAG at −90° C. obtained at 100× and 500× magnification, respectively.

DETAILED DESCRIPTION

A. Metathesized Triacylglycerols of Natural Oils

Figure 1:
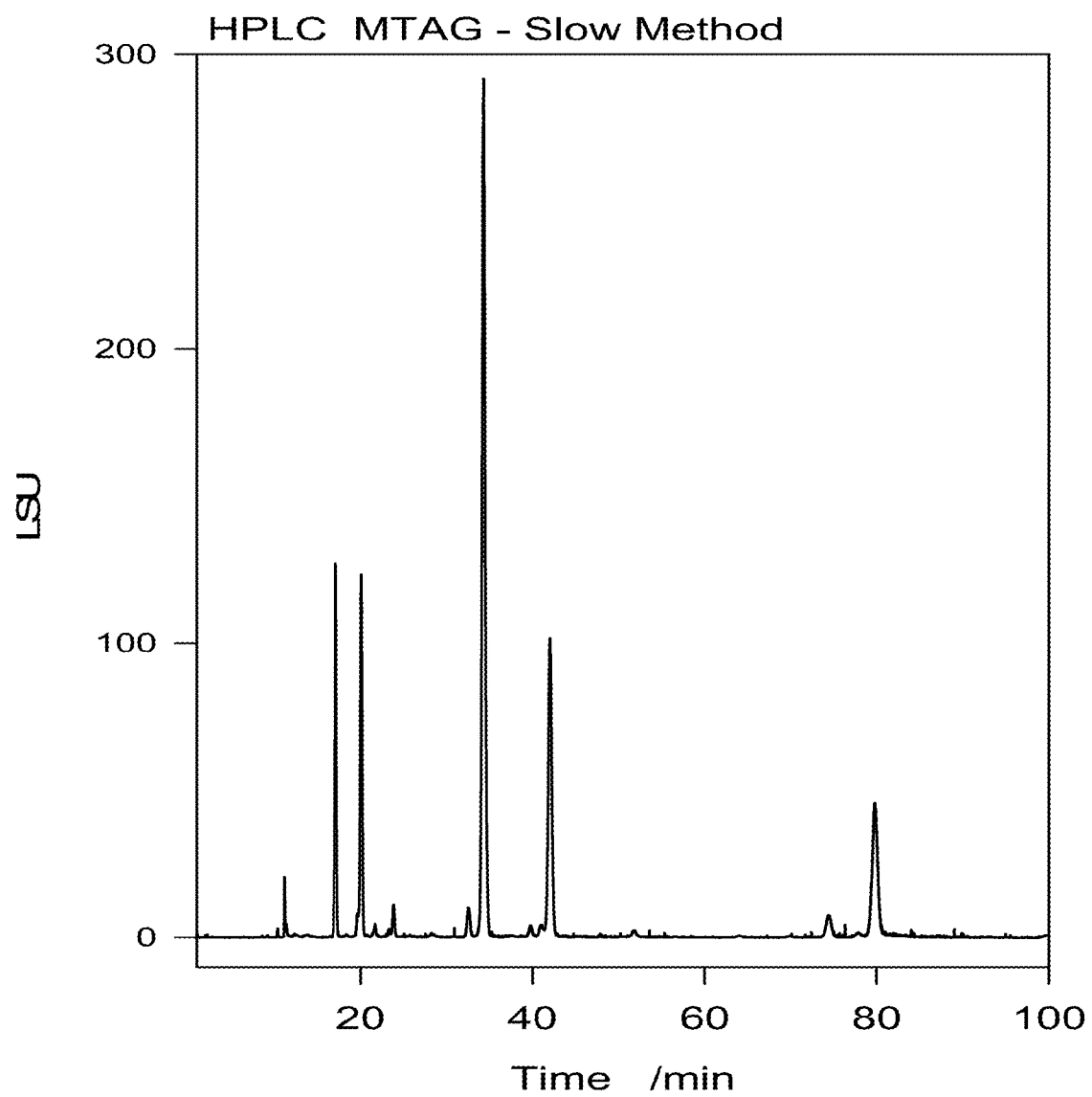
FIG. 1 depicts a HPLC of PMTAG.

Synthesis of Metathesized Triacylglycerols for Production of Polyols

The synthesis of rigid and flexible polyurethane foams, and other polyurethanes, from natural oil based metathesized triacylglycerol (MTAG), including palm oil MTAG or PMTAG, and polyols thereof, begins with the initial synthesis of the MTAGs themselves. A general definition of a metathesized triacylglycerol is the product formed from the metathesis reaction (self-metathesis or cross-metathesis) of an unsaturated triglyceride in the presence of a metathesis catalyst to form a product including one or more metathesis monomers, oligomers or polymers.

Metathesis is a catalytic reaction that involves the interchange of alkylidene units among compounds containing one or more double bonds (i.e., olefinic compounds) via the formation and cleavage of the carbon-carbon double bonds. The metathesis catalyst in this reaction may include any catalyst or catalyst system that catalyzes a metathesis reaction. Cross metathesis may be represented schematically as shown in Scheme 1 below:

Scheme 1. Representation of cross-metathesis reaction.

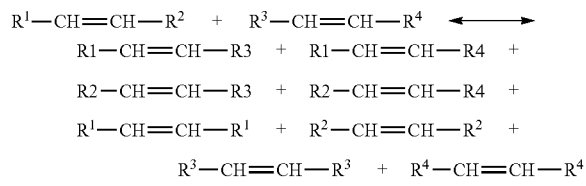

Wherein R¹, R², R³, and R⁴ are organic groups.

Suitable homogeneous metathesis catalysts include combinations of a transition metal halide or oxo-halide (e.g., WOCl₄ or WCl₆) with an alkylating cocatalyst (e.g., Me₄Sn). Homogeneous catalysts include well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

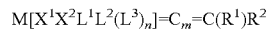

$$M[X^1X^2L^1L^2(L^3)_n]=C_m=C(R^1)R^2$$

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference. Second-generation Grubbs catalysts also have the general formula described above, but $L^1$ is a carbene ligand where the carbene carbon is flanked by N, O, S, or P atoms, e.g., by two N atoms. The carbene ligand may be part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like. In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. A neutral oxygen or nitrogen may coordinate to the metal while also being bonded to a carbon that is α-, β-, or γ- with respect to the carbene carbon to provide the bidentate ligand. Examples of suitable Grubbs-Hoveyda catalysts appear in the '086 publication.

The structures below (Scheme 2) provide just a few illustrations of suitable catalysts that may be used:

Scheme 2. Structures of few metathesis catalysts.

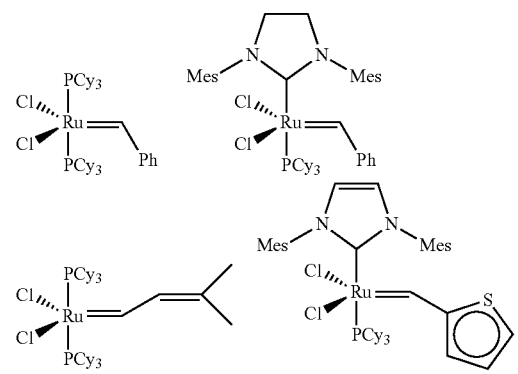

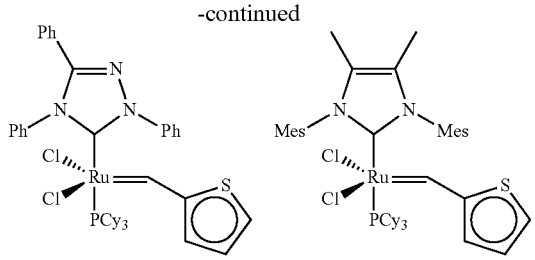

Heterogeneous catalysts suitable for use in the self- or cross-metathesis reactions include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins. For additional examples of suitable catalysts for self- or cross-metathesis, see U.S. Pat. No. 4,545,941, the teachings of which are incorporated herein by reference, and references cited therein. See also *J. Org. Chem.* 46 (1981) 1821; *J. Catal.* 30 (1973) 118; *Appl. Catal.* 70 (1991) 295; *Organometallics* 13 (1994) 635; *Olefin Metathesis and Metathesis Polymerization* by Ivin and Mol (1997), and *Chem. & Eng. News* 80(51), Dec. 23, 2002, p. 29, which also disclose useful metathesis catalysts. Illustrative examples of suitable catalysts include ruthenium and osmium carbene catalysts as disclosed in U.S. Pat. Nos. 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.).

As a non-limiting aspect, a route to obtain MTAG (or PMTAG) may be via the cross metathesis of a natural oil (e.g., palm oil) with a lower weight olefin. As a non-limiting aspect, reaction routes using triolein with 1,2-butene and triolein with ethylene are shown below in Scheme 3a and 3b, respectively.

Scheme 3a. Metathesis reaction of triolein with 1,2-butylene.

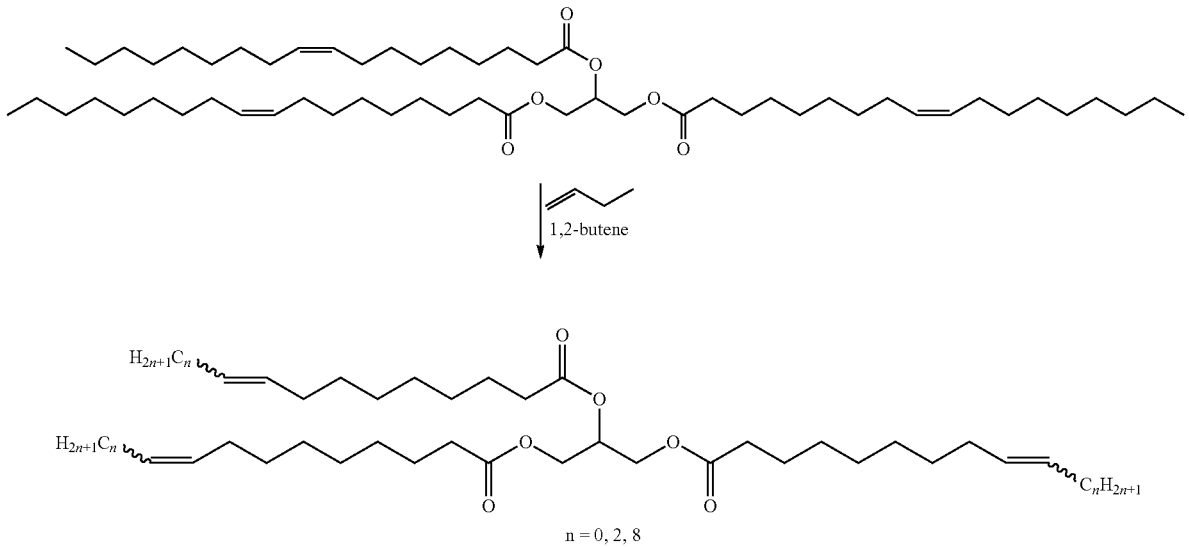

n = 0, the fatty acid is 9-denenoic acid (D),
n = 2, the fatty acid is 9-dodecenoic acid (Dd) and
n = 8, the fatty acid is oleic acid (O).

Scheme 3b. Metathesis reaction of triolein with ethylene.

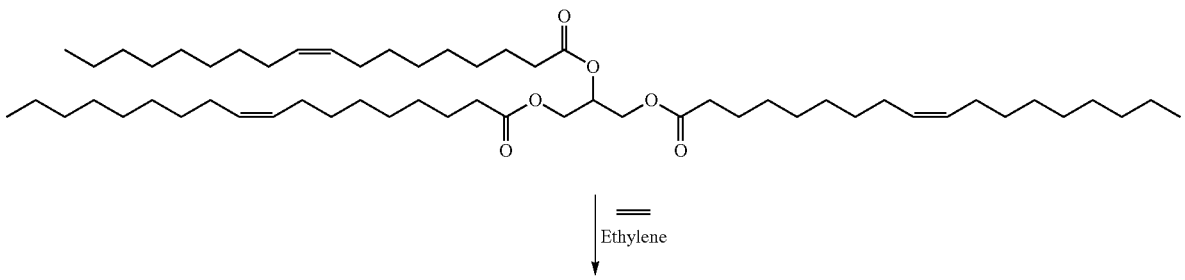

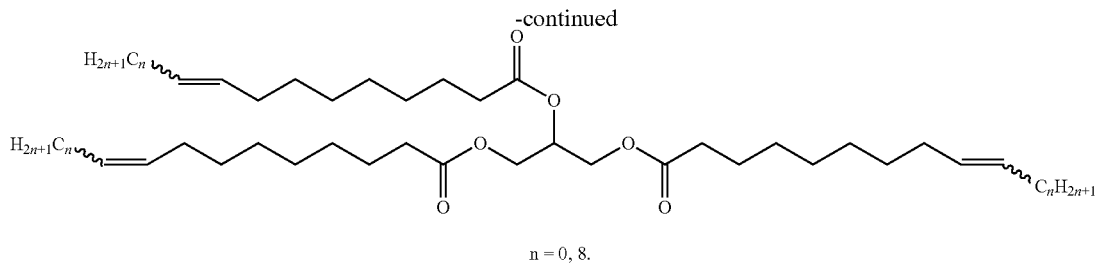

n = 0, 8.

n = 0, the fatty acid is 9-denenoic acid (D), and n = 8, the fatty acid is oleic acid (O).

As used herein, the term "lower weight olefin" may refer to any one or a combination of unsaturated straight, branched, or cyclic hydrocarbons in the $C_2$ to $C_{14}$ range. Lower weight olefins include "alpha-olefins" or "terminal olefins," wherein the unsaturated carbon-carbon bond is present at one end of the compound. Lower weight olefins may also include dienes or trienes. Examples of low weight olefins in the $C_2$ to $C_6$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Other possible low weight olefins include styrene and vinyl cyclohexane. In certain embodiments, a mixture of olefins may be used, the mixture including linear and branched low weight olefins in the $C_4$-$C_{10}$ range. In one embodiment, a mixture of linear and branched $C_4$ olefins may be used (e.g., combinations of: 1-butene, 2-butene, and/or isobutene). In other embodiments, a higher range of $C_{11}$-$C_{14}$ may be used.

As used herein, the term "natural oil" may refer to oil derived from plants or animal sources. The term "natural oil" includes natural oil derivatives, unless otherwise indicated. Examples of natural oils include, but are not limited to, vegetable oils, algal oils, animal fats, tall oils, derivatives of these oils, combinations of any of these oils, and the like. Representative non-limiting examples of vegetable oils include canola oil, rapeseed oil, coconut oil, corn oil, cottonseed oil, jojoba oil, olive oil, palm oil, peanut oil, safflower oil, sesame oil, soybean oil, sunflower oil, linseed oil, palm kernel oil, tung oil, jatropha oil, mustard oil, camelina oil, pennycress oil, hemp oil, algal oil, and castor oil. Representative non-limiting examples of animal fats include lard, tallow, poultry fat, yellow grease, and fish oil. Tall oils are by-products of wood pulp manufacture. In certain embodiments, the natural oil may be refined, bleached, and/or deodorized. In some embodiments, the natural oil may be partially or fully hydrogenated. In some embodiments, the natural oil is present individually or as mixtures thereof.

Natural oils may include triacylglycerols of saturated and unsaturated fatty acids. Suitable fatty acids may be saturated or unsaturated (monounsaturated or polyunsaturated) fatty acids, and may have carbon chain lengths of 3 to 36 carbon atoms. Such saturated or unsaturated fatty acids may be aliphatic, aromatic, saturated, unsaturated, straight chain or branched, substituted or unsubstituted and mono-, di-, tri-, and/or poly-acid variants, hydroxy-substituted variants, aliphatic, cyclic, alicyclic, aromatic, branched, aliphatic- and alicyclic-substituted aromatic, aromatic-substituted aliphatic and alicyclic groups, and heteroatom substituted variants thereof. Any unsaturation may be present at any suitable isomer position along the carbon chain as would be noted to a person skilled in the art.

Some non-limiting examples of saturated fatty acids include propionic, butyric, valeric, caproic, enanthic, caprylic, pelargonic, capric, undecylic, lauric, tridecylic, myristic, pentadecanoic, palmitic, margaric, stearic, nonadecyclic, arachidic, heneicosylic, behenic, tricosylic, lignoceric, pentacoyslic, cerotic, heptacosylic, carboceric, montanic, nonacosylic, melissic, lacceroic, psyllic, geddic, ceroplastic acids.

Some non-limiting examples of unsaturated fatty acids include butenoic, pentenoic, hexenoic, pentenoic, octenoic, nonenoic acid, decenoic acid, undecenoic acid, dodecenoic acid, tridecenoic, tetradecenoic, pentadecenoic, palmitoleic, palmitelaidic, oleic, ricinoleic, vaccenic, linoleic, linolenic, elaidic, eicosapentaenoic, behenic and erucic acids. Some unsaturated fatty acids may be monounsaturated, diunsaturated, triunsaturated, tetraunsaturated or otherwise polyunsaturated, including any omega unsaturated fatty acids.

In a triacylglycerol, each of the carbons in the triacylglycerol molecule may be numbered using the stereospecific numbering (sn) system. Thus one fatty acyl chain group is attached to the first carbon (the sn-1 position), another fatty acyl chain is attached to the second, or middle carbon (the sn-2 position), and the final fatty acyl chain is attached to the third carbon (the sn-3 position). The triacylglycerols described herein may include saturated and/or unsaturated fatty acids present at the sn-1, sn-2, and/or sn-3 position In some embodiments, the natural oil is palm oil. Palm oil may be a semi-solid at room temperature and includes approximately 50% saturated fatty acids and approximately 50% unsaturated fatty acids. Palm oil may include predominately fatty acid triacylglycerols, although monoacylglycerols and diacylglycerols may also be present in small amounts. The fatty acids may have chain lengths ranging from about C12 to about C20. Representative saturated fatty acids include, for example, C12:0, C14:0, C16:0, C18:0, and C20:0 saturated fatty acids. Representative unsaturated fatty acids include, for example, C16:1, C18:1, C18:2, and C18:3 unsaturated fatty acids. As used herein, metathesized triacylglycerols derived from palm oil may be referred to interchangeably as "palm oil MTAG" or "PMTAG" or "MTAG of/from palm oil."

Palm oil is constituted mainly of palmitic acid and oleic acid with ~43% and ~41%, respectively. The fatty acid and triglyceride (TAG) profiles of palm oil are listed in Table 1 and Table 2, respectively.

TABLE 1

Fatty acid profile of palm oil

| | \multicolumn{7}{c}{Fatty acid} |
|---|---|---|---|---|---|---|---|
| | C12:0 | C14:0 | C16:0 | C18:0 | C18:1 | C18:2 | Others |
| Content (%) | 0.2 | 1.0 | 42.9 | 4.4 | 40.8 | 10.2 | 0.5 |

TABLE 2

TAG profiles of palm oil. (M, myristic acid; O, oleic acid; P, palmitic acid; L, linoleic acid; S, stearic acid)

| | \multicolumn{10}{c}{Unsaturated TAGs} |
|---|---|---|---|---|---|---|---|---|---|---|
| | OLL | PLL | OLO | POL | PLP | OOO | POO | POP | SOO | POS |
| Content (%) | 0.4 | 1.2 | 1.5 | 8.9 | 9.2 | 3.9 | 23.2 | 30.2 | 2.9 | 6.7 |

| | Saturated TAGs | | | |
|---|---|---|---|---|
| | PPM | PPP | PPS | Others |
| Content (%) | 0.2 | 6.7 | 1.1 | 3.8 |

Analytical Methods for PMTAG

The PMTAG, as represented by the non-limiting synthesis procedure, was analyzed using different techniques. These techniques can be broken down into: (i) chemistry characterization techniques, including iodine value, acid value, nuclear magnetic resonance (NMR), gas chromatography (GC), and high pressure liquid chromatography (HPLC), including fast and slow methods of the HPLC; and (ii) physical characterization methods, including thermogravimetric analysis (TGA), differential scanning calorimetry (DSC), rheology, solid fat content (SFC), and polarized light microscopy (PLM).

Chemistry Characterization Techniques

Iodine and acid values of the PMTAG was determined according to ASTM D5554-95 and ASTM D4662-03, respectively.

$^1$H-NMR spectra were recorded on a Varian Unity-INOVA at 499.695 MHz. $^1$H chemical shifts are internally referenced to CDCl$_3$ (7.26 ppm) for spectra recorded in CDCl$_3$. All spectra were obtained using an 8.6 µs pulse with 4 transients collected in 16 202 points. Datasets were zero-filled to 64 000 points, and a line broadening of 0.4 Hz was applied prior to Fourier transforming the sets. The spectra were processed using ACD Labs NMR Processor, version 12.01.

HPLC analysis was performed on a Waters Alliance (Milford, Mass.) e2695 HPLC system fitted with a Waters ELSD 2424 evaporative light scattering detector. The HPLC system was equipped with an inline degasser, a pump, and an autosampler. The ELSD nitrogen flow was set at 25 psi with nebulization and drifting tube maintained at 12° C. and 55° C., respectively. Gain was set at 500. All solvents were HPLC grade and obtained from VWR International, Mississauga, ON. Waters Empower Version 2 software was used for data collection and data analysis. Purity of eluted samples was determined using the relative peak area. For a fast method of PMTAG analysis, the analysis was performed on a C18 column (150 mm×4.6 mm, 5.0 µm, X-Bridge column, Waters Corporation, MA) maintained at 30° C. by column oven (Waters Alliance). The mobile phase was chloroform:acetonitrile (40:60)v run for 10 min at a flow rate of 1 ml/min. 1 mg/ml (w/v) solution of crude sample in chloroform was filtered through single step filter vial (Thomson Instrument Company, 35540, CA) and 10 µL of sample was passed through the C18 column by reversed-phase in isocratic mode. For a slower method of PMTAG analysis, the analysis was performed using two columns (C18, 150 mm×4.6 mm, 5.0 µm, X-Bridge column, Waters Corporation, MA, and Superspher 100 RP-18, 250 mm×4.0 mm, Thermo Science) set up in series at 30° C. The mobile phase was 2-Propanol:acetonitrile:Heptane (38:57:5)v run for 120 min at a flow rate of 0.5 ml/min. 5 mg/ml (w/v) solution of crude sample in Heptane was filtered through single step filter vial (Thomson Instrument Company, CA) and 4 µL of sample was passed through the columns by reversed-phase in isocratic mode. This method achieved a better separation than the fast method.

Gas chromatography (GC) was performed on an Agilent 7890 Gas Chromatograph equipped with a split/splitless inlet. The column effluent was split using an Agilent splitter assembly with makeup gas. The splitter was connected the two detectors via deactivated guard columns. The length of the guard column was 0.5 m to the Flame Ionization Detector and 5.0 m to the Agilent 5975C Mass Selective detector. The column used for the analysis was a Restek Rtx-65TG capillary column (Crossbond 65% diphenyl/35% dimethyl polysiloxane; 30 m×0.25 mm×0.1 µm df). One microliter of the sample was injected using a LEAP Technologies Combi-PAL autosampler equipped with a 10 µL syringe.

| Instrument Parameters - Agilent GC/MS - FID | |
|---|---|
| Injection Volume | 1 µL |
| Syringe Size | 10 µL |
| Septum Purge Flow | 3 mL/minute |
| Split Ratio | 20:1 |
| Split Flow | 40 mL/minute |
| Column Flow (Helium) | 2 mL/minute (constant flow) |
| Initial Column Pressure | 16.0 psig |
| Inlet Temperature | 275° C. |
| MSD Transfer Line | 300° C. |
| Oven Parameters | |
| Equilibration Time | 0.5 minutes |
| Initial Temperature | 40° C. |
| Initial Time | 5 minutes |
| Temperature Ramp 1 | 10° C./minute |
| Final Temperature 1 | 200° C. |
| Time 1 | 0 minutes |
| Temperature Ramp 2 | 20° C./minute |
| Final Temperature 2 | 350° C. |
| Time 2 | 11.5 minutes |
| Total Run Time | 40 minutes |

-continued

| Instrument Parameters - Agilent GC/MS - FID | |
|---|---|
| MSD Parameters | |
| Solvent Delay | 2 minutes |
| EMV Mode | Relative |
| Relative Voltage | 0 |
| Resulting EM Voltage | 1765 |
| Low Mass | 35.0 amu |
| High Mass | 550 amu |
| MS Source Temperature | 230° C. |
| MS Quad Temperature | 150° C. |
| FID Parameters | |
| Detector Temperature | 375° C. |
| Hydrogen Flow | 30 mL/minute |
| Air Flow | 400 mL/minute |
| Makeup Flow (Nitrogen) | 25 mL/minute |

Physical Characterization Techniques

TGA was carried out on a TGA Q500 (TA Instruments, DE, USA) equipped with a TGA heat exchanger (P/N 953160.901). Approximately 8.0-15.0 mg of sample was loaded in the open TGA platinum pan. The sample was heated from 25 to 600° C. under dry nitrogen at a constant rate of 10° C./min.

DSC measurements were run on a Q200 model (TA Instruments, New Castle, Del.) under a nitrogen flow of 50 mL/min. TAG samples of 3.5 to 6.5 (±0.1) mg were run in hermetically sealed aluminum DSC pans. Crystallization and melting behavior of PMTAG was investigated using standard DSC. The samples were equilibrated at 90° C. for 10 min to erase thermal memory, and then cooled at a constant rate of 5.0, 1.0 or 0.1° C./min to −90° C. where they were held isothermally for 5 min, and subsequently reheated at a constant rate of 5.0° C./min to 90° C. The "TA Universal Analysis" software was used to analyze the DSC thermograms and extract the peak characteristics. Characteristics of non-resolved peaks were obtained using the first and second derivatives of the differential heat flow.

SFC measurements were performed on a Bruker Minispec mq 20 pNMR spectrometer (Milton, ON, Canada) equipped with a combined high and low temperature probe supplied with N2. The temperature was controlled with Bruker's BVT3000 temperature controller with an accuracy of ±0.1° C. The temperature was calibrated with commercial canola oil using a type K probe (TRP-K, Omega, Stamford, Conn.) immersed in the oil and an external data logger (Oakton, Eutech Instruments, Singapore). Approximately 0.57±0.05 ml of fully melted sample was quickly pipetted into the bottom portion of the NMR tube. The thermal protocol used in the DSC were also used in the NMR. Bruker's minispec V2.58 Rev. 12 and minispec plus V1.1 Rev. 05 software were used to collect SFC data as a function of time and temperature. The SFC values are reported as the ratio of the intensity of the NMR signal of the solid part to the total detected NMR signal in percent (labelled as SFC %).

A Leica DM2500P polarized light microscope (PLM) fitted with a Leica DFC420C digital camera (Leica Microsystems, Wetzlar, Germany) was used for image capture of the microstructure of the PMTAG. The samples were processed in a temperature-controlled stage (Linkam LTS 350) fitted to the PLM. The formation of the fat crystal network from the early crystallites through their growth and aggregation were observed in-situ under the PLM. The micrographs presented (100× and 500×) were captured at −90° C.

A temperature-controlled Rheometer (AR2000ex, TA Instruments, DE, USA) was used to measure the viscosity and flow property of PMTAG using a 40 mm 2° steel geometry. Temperature control was achieved by a Peltier attachment with an accuracy of 0.1° C. Shear Stress was measured at each temperature by varying the shear rate from 1 to 1200 $s^{-1}$. Measurements were taken at 10° C. intervals from high temperature (100° C.) to 10° C. below the DSC onset of crystallization temperature of each sample. Viscosities of samples were measured from each sample's melting point up to 110° C. at constant temperature rate (1.0 and 3.0° C./min) with constant shear rate (200 $s^{-1}$). Data points were collected at intervals of 1° C. The viscosity obtained in this manner was in very good agreement with the measured viscosity using the shear rate/share stress. The shear rate range was optimized for torque (lowest possible is 10 μNm) and velocity (maximum suggested of 40 rad/s).

The shear rate-shear stress curves were fitted with the Herschel-Bulkley equation (Eq 1), a model commonly used to describe the general behavior of materials characterized by a yield stress.

$$\tau = \tau_0 + K\dot{\gamma}^n \qquad \text{Eq. 1}$$

where $\dot{\gamma}$ denotes the shear stress, $\tau_0$ is the yield stress below which there is no flow, K the consistency index and n the power index. n depends on constitutive properties of the material. For Newtonian fluids n=1, shear thickening fluids, n>1 and for shear thinning fluids, n<1.

Palm Oil MTAG Compositional Analysis

The natural oil composition, and in particular, the palm oil composition, was described previously, and the TAG profiles of palm oil were also described previously The TAGs which can potentially compose MTAG based on palm oil composition and the possible products of cross-metathesis of palm oil are listed in Table 3a. The potential structures of TAGs in PMTAG are listed in Table 3b.

TABLE 3a

Potential TAG composition in PMTAG. D: 9-decenoic acid; Dd: 9-dodecenioc acid; M, myristic acid; O, oleic acid; P, palmitic acid; L, linoleic acid; S, stearic acid. There are both trans- and cis- double bonds in the TAG

| TAGs in Palm oil | Potential TAG composition of PMTAG |
|---|---|
| OLL, OLO, OOO | ODD, DDD, DDDd, DDdDd, OLL, OLO, OOO, OLD, OLDd, OOD, ODD, ODDd, ODdDd, LDD, LDDd, LDdDd, DdDdDd, and their isomers |
| PLL | PLL, PDD, PLD, PDDd, PLDd, PDdDd and their isomers |
| POL, POO | POL, POO, PDD, POD, PDDd, PODd, PDdDd and their isomers |
| SOO | SOO, SDD, SOD, SDDd, SODd, SDdDd and their isomers |
| PLP, | PLP, PDP, PDdP |
| POP | POP, PDP, PDdP |
| POS | POS, PDS, PDdS |
| PPM, PPP, PPS | PPM, PPP, PPS |

TABLE 3b

Structures of potential TAGs in PMTAG

| Compound | Structure |
|---|---|
| OLL | 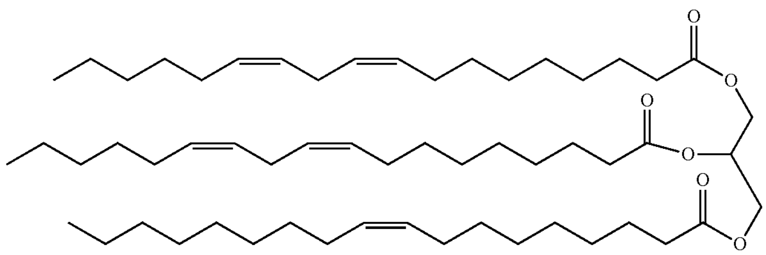 [SMILES: CCCCC/C=C\C/C=C\CCCCCCCC(=O)OCC(COC(=O)CCCCCCC/C=C\CCCCCCCC)OC(=O)CCCCCCC/C=C\C/C=C\CCCCC] |
| OLO | 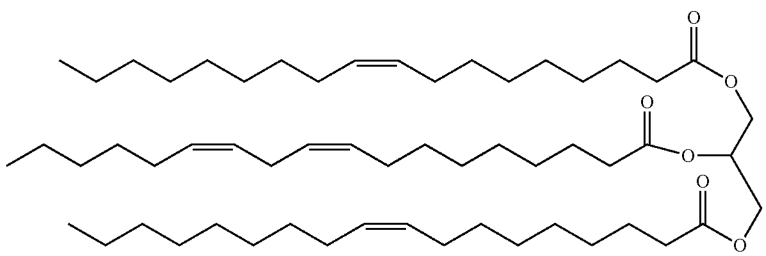 [SMILES: CCCCC/C=C\C/C=C\CCCCCCCC(=O)OC(COC(=O)CCCCCCC/C=C\CCCCCCCC)COC(=O)CCCCCCC/C=C\CCCCCCCC] |
| OOO | 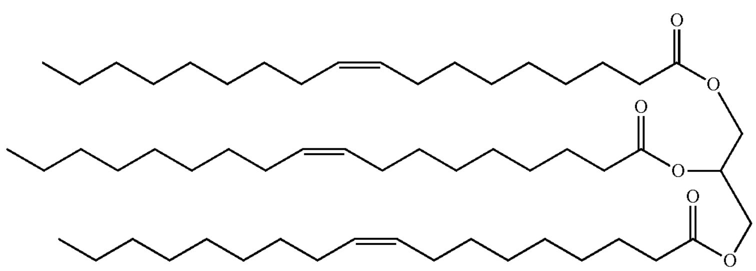 [SMILES: CCCCCCCC/C=C\CCCCCCCC(=O)OCC(COC(=O)CCCCCCC/C=C\CCCCCCCC)OC(=O)CCCCCCC/C=C\CCCCCCCC] |
| ODD | 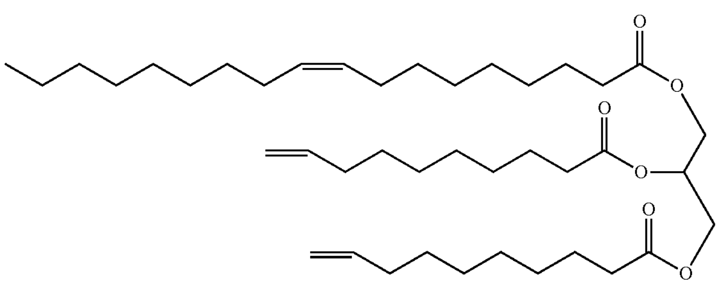 [SMILES: C=CCCCCCCCC(=O)OCC(COC(=O)CCCCCCC/C=C\CCCCCCCC)OC(=O)CCCCCCCC=C] |
| DDD | 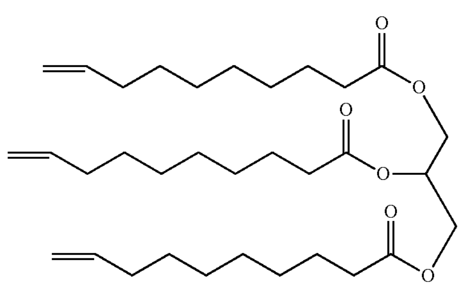 [SMILES: C=CCCCCCCCC(=O)OCC(COC(=O)CCCCCCCC=C)OC(=O)CCCCCCCC=C] |

TABLE 3b-continued
Structures of potential TAGs in PMTAG
| Compound | Structure |
|---|---|
| DDDd | 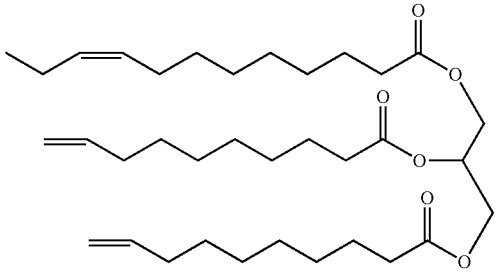 [SMILES: C=CCCCCCCCC(=O)OCC(COC(=O)CCCCCCC/C=C\CC)OC(=O)CCCCCCCC=C] |
| DDdDd | 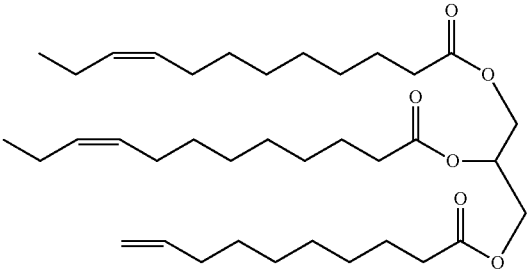 [SMILES: C=CCCCCCCCC(=O)OCC(COC(=O)CCCCCCC/C=C\CC)OC(=O)CCCCCCC/C=C\CC] |
| OLD | 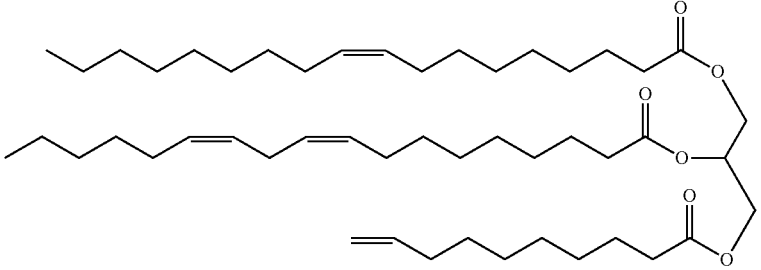 [SMILES: C=CCCCCCCCC(=O)OCC(COC(=O)CCCCCCC/C=C\CCCCCCCC)OC(=O)CCCCCCC/C=C\C/C=C\CCCCC] |
| OLDd | 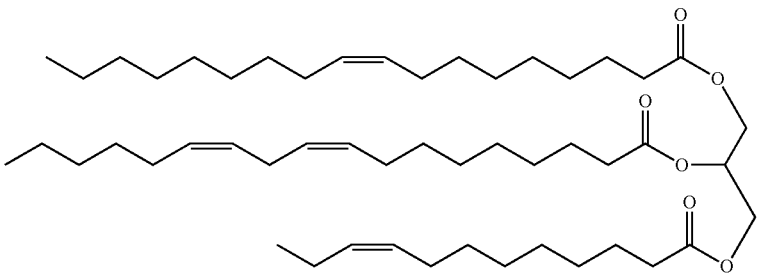 [SMILES: CC/C=C\CCCCCCCC(=O)OCC(COC(=O)CCCCCCC/C=C\CCCCCCCC)OC(=O)CCCCCCC/C=C\C/C=C\CCCCC] |
| OOD | 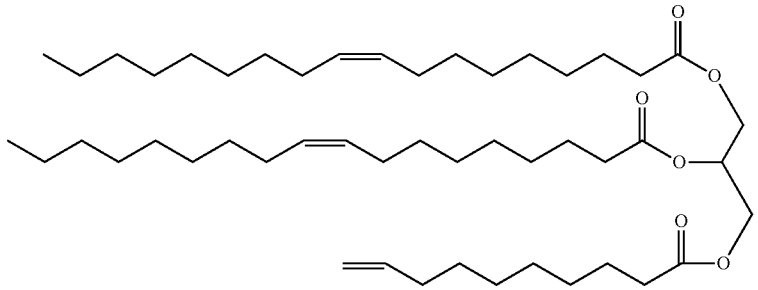 [SMILES: C=CCCCCCCCC(=O)OCC(COC(=O)CCCCCCC/C=C\CCCCCCCC)OC(=O)CCCCCCC/C=C\CCCCCCCC] |

TABLE 3b-continued
Structures of potential TAGs in PMTAG
| Compound | Structure |
|---|---|
| ODD | 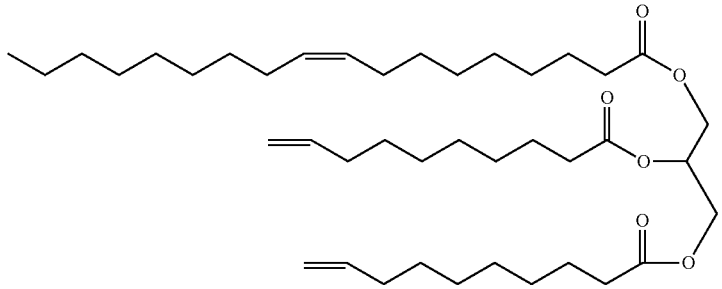 [SMILES: C=CCCCCCCCC(=O)OCC(COC(=O)CCCCCCC/C=C\CCCCCCCC)OC(=O)CCCCCCCC=C] |
| ODDd | 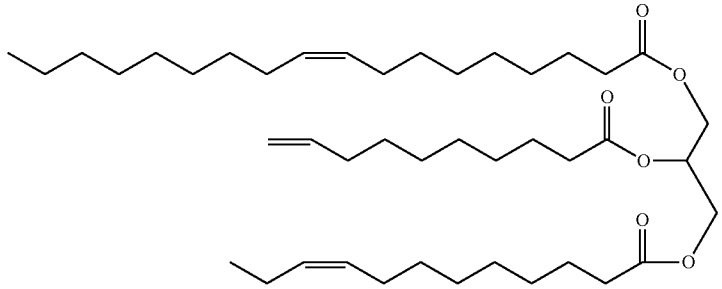 [SMILES: C=CCCCCCCCC(=O)OC(COC(=O)CCCCCCC/C=C\CC)COC(=O)CCCCCCC/C=C\CCCCCCCC] |
| ODdDd | 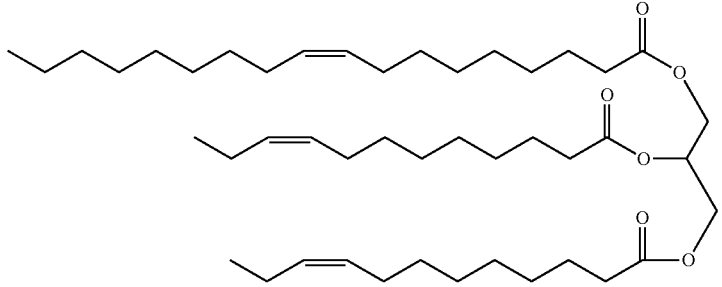 [SMILES: CC/C=C\CCCCCCCC(=O)OCC(COC(=O)CCCCCCC/C=C\CCCCCCCC)OC(=O)CCCCCCC/C=C\CC] |
| LDD | 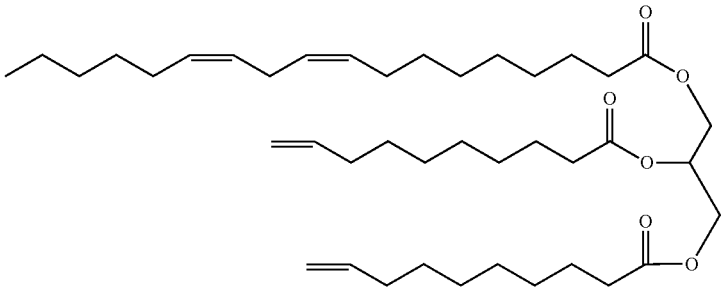 [SMILES: C=CCCCCCCCC(=O)OCC(COC(=O)CCCCCCC/C=C\C/C=C\CCCCC)OC(=O)CCCCCCCC=C] |
| LDDd | 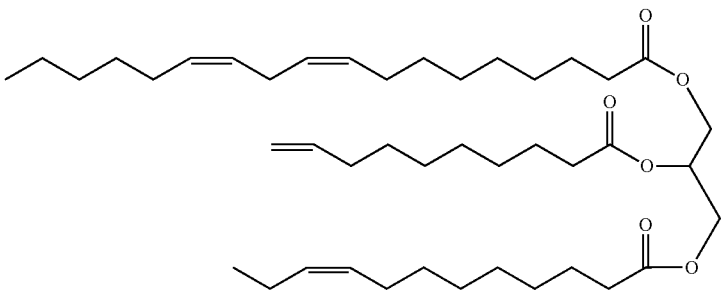 [SMILES: C=CCCCCCCCC(=O)OC(COC(=O)CCCCCCC/C=C\CC)COC(=O)CCCCCCC/C=C\C/C=C\CCCCC] |

TABLE 3b-continued
Structures of potential TAGs in PMTAG
| Compound | Structure |
|---|---|
| LDdDd | 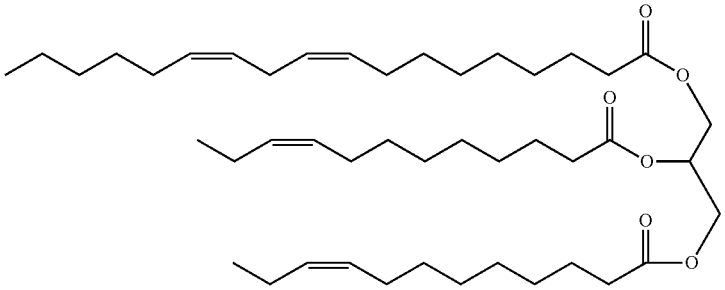 [SMILES: CC/C=C\CCCCCCCC(=O)OCC(COC(=O)CCCCCCC/C=C\C/C=C\CCCCC)OC(=O)CCCCCCC/C=C\CC] |
| DdDdDd | 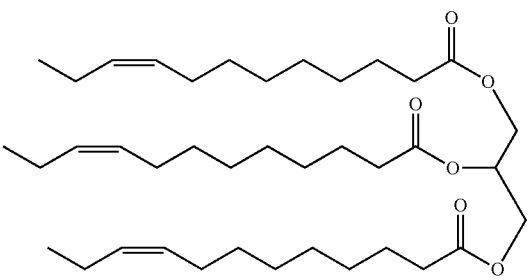 [SMILES: CC/C=C\CCCCCCCC(=O)OCC(COC(=O)CCCCCCC/C=C\CC)OC(=O)CCCCCCC/C=C\CC] |
| PLL | 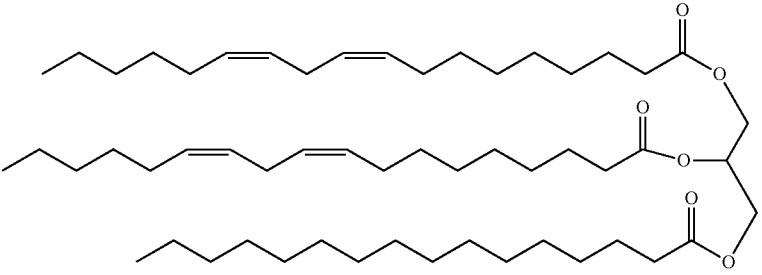 [SMILES: CCCCC/C=C\C/C=C\CCCCCCCC(=O)OCC(COC(=O)CCCCCCCCCCCCCCC)OC(=O)CCCCCCC/C=C\C/C=C\CCCCC] |
| PDD | 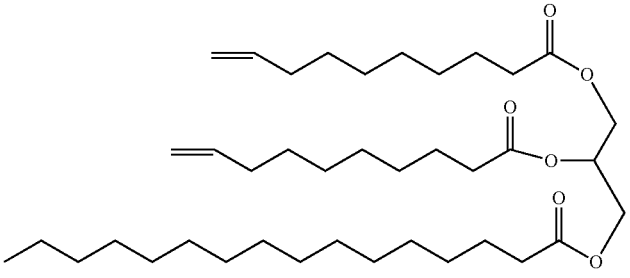 [SMILES: C=CCCCCCCCC(=O)OCC(COC(=O)CCCCCCCCCCCCCCC)OC(=O)CCCCCCCC=C] |
| PLD | 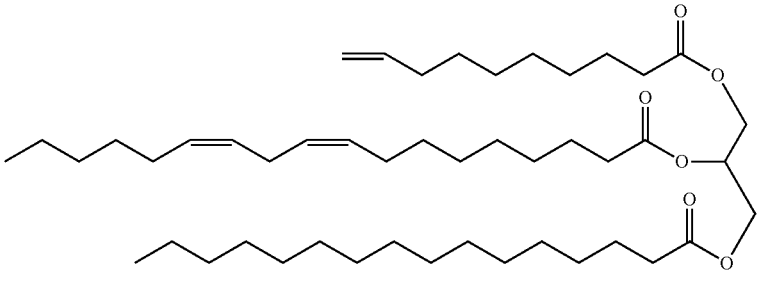 [SMILES: C=CCCCCCCCC(=O)OCC(COC(=O)CCCCCCCCCCCCCCC)OC(=O)CCCCCCC/C=C\C/C=C\CCCCC] |

TABLE 3b-continued
Structures of potential TAGs in PMTAG
| Compound | Structure |
|---|---|
| PDDd | 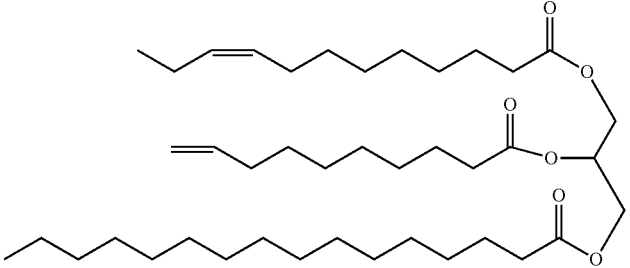 [SMILES: C=CCCCCCCCC(=O)OC(COC(=O)CCCCCCC/C=C\CC)COC(=O)CCCCCCCCCCCCCCC] |
| PLDd | 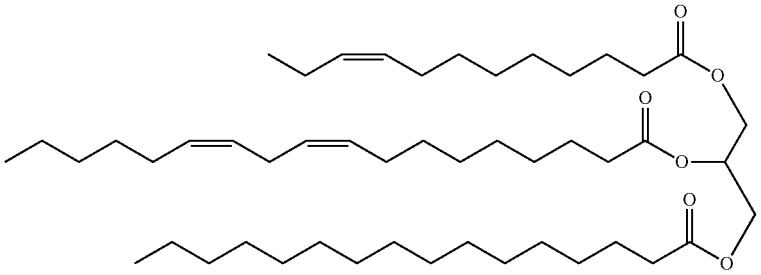 [SMILES: CC/C=C\CCCCCCCC(=O)OCC(COC(=O)CCCCCCCCCCCCCCC)OC(=O)CCCCCCC/C=C\C/C=C\CCCCC] |
| PDdDd | 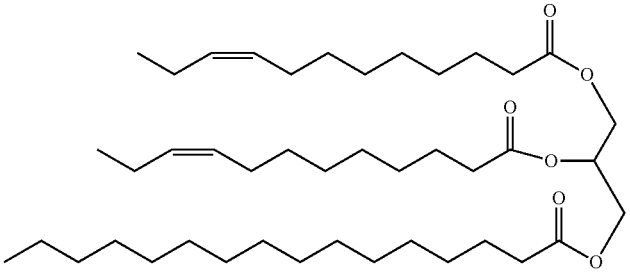 [SMILES: CC/C=C\CCCCCCCC(=O)OCC(COC(=O)CCCCCCCCCCCCCCC)OC(=O)CCCCCCC/C=C\CC] |
| POL | 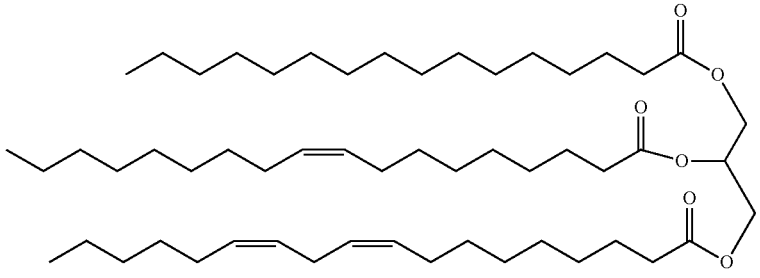 [SMILES: CCCCC/C=C\C/C=C\CCCCCCCC(=O)OCC(COC(=O)CCCCCCCCCCCCCCC)OC(=O)CCCCCCC/C=C\CCCCCCCC] |
| POO | 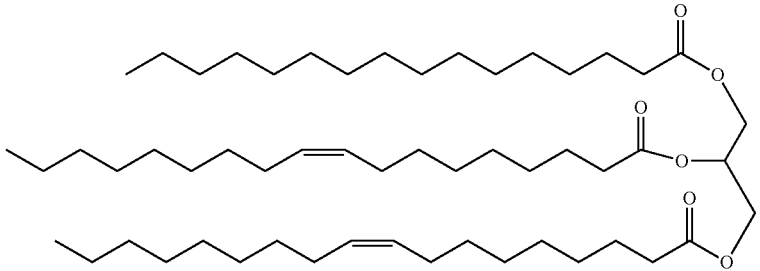 [SMILES: CCCCCCCC/C=C\CCCCCCCC(=O)OCC(COC(=O)CCCCCCCCCCCCCCC)OC(=O)CCCCCCC/C=C\CCCCCCCC] |

TABLE 3b-continued
Structures of potential TAGs in PMTAG
| Compound | Structure |
|---|---|
| POD | 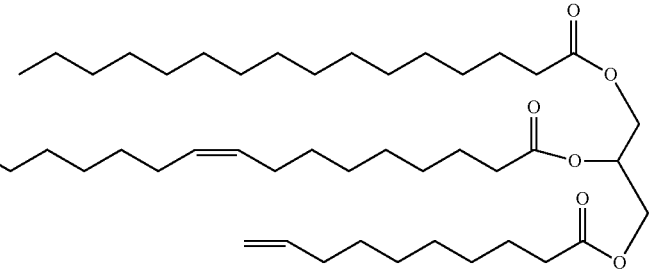 |
| PODd | 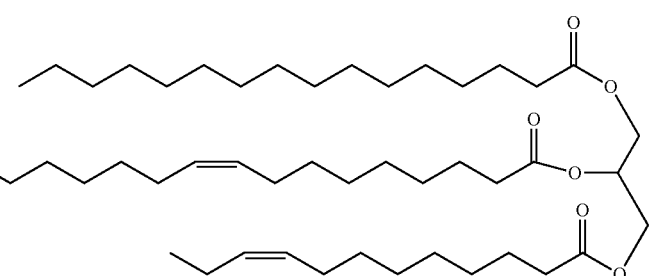 |
| SOO | 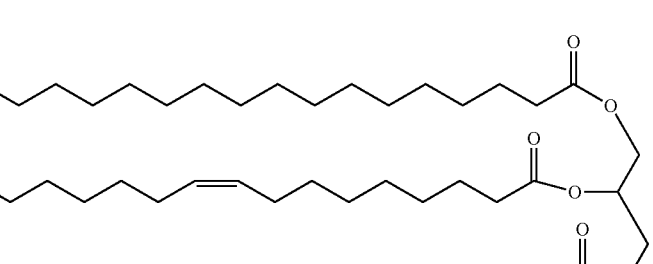 |
| SDD | 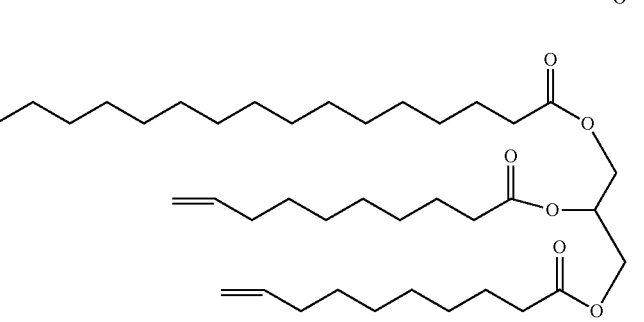 |
| SOD | 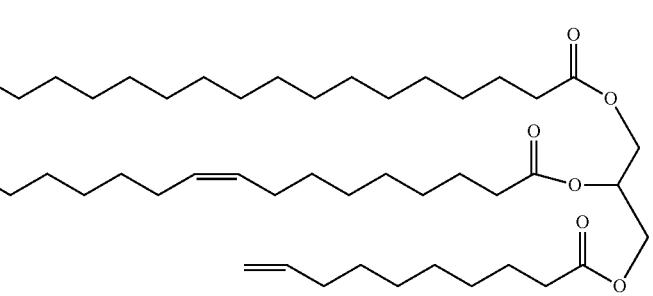 |

TABLE 3b-continued

Structures of potential TAGs in PMTAG

| Compound | Structure |
|---|---|
| SDDd | 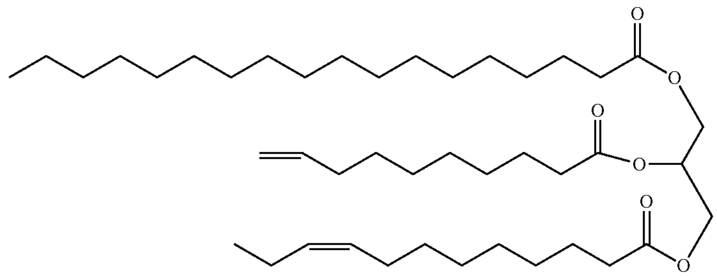 [SMILES: C=CCCCCCCCC(=O)OC(COC(=O)CCCCCCC/C=C\CC)COC(=O)CCCCCCCCCCCCCCCCC] |
| SODd | 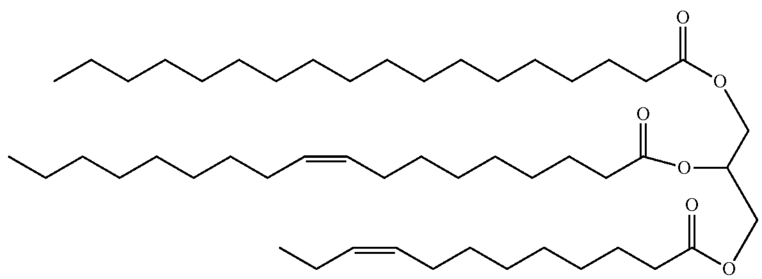 [SMILES: CC/C=C\CCCCCCCC(=O)OCC(COC(=O)CCCCCCCCCCCCCCCCC)OC(=O)CCCCCCC/C=C\CCCCCCCC] |
| SDdDd | 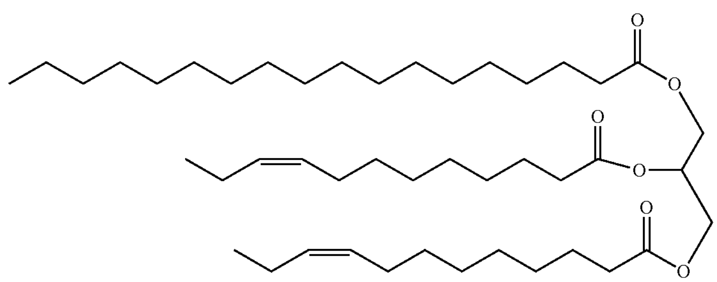 [SMILES: CC/C=C\CCCCCCCC(=O)OCC(COC(=O)CCCCCCCCCCCCCCCCC)OC(=O)CCCCCCC/C=C\CC] |
| PLP | 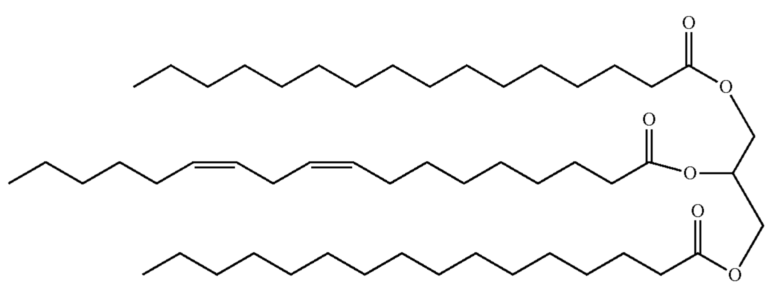 [SMILES: CCCCC/C=C\C/C=C\CCCCCCCC(=O)OC(COC(=O)CCCCCCCCCCCCCCC)COC(=O)CCCCCCCCCCCCCCC] |
| PDP | 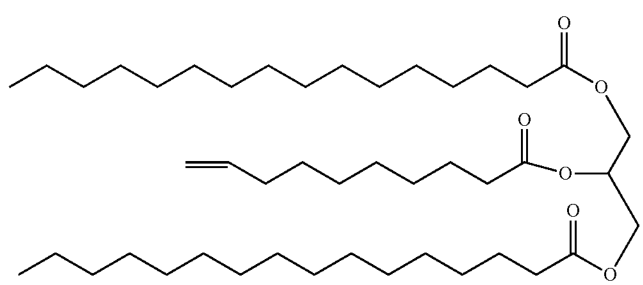 [SMILES: C=CCCCCCCCC(=O)OC(COC(=O)CCCCCCCCCCCCCCC)COC(=O)CCCCCCCCCCCCCCC] |

TABLE 3b-continued
Structures of potential TAGs in PMTAG
| Compound | Structure |
|---|---|
| PDdP | 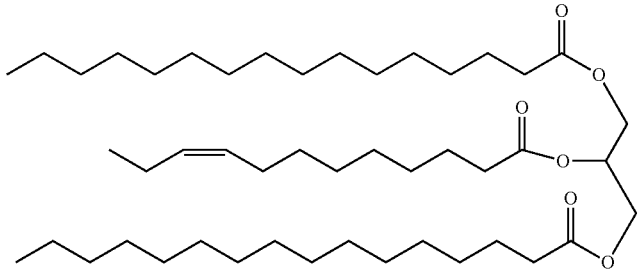 [SMILES: CC/C=C\CCCCCCCC(=O)OC(COC(=O)CCCCCCCCCCCCCCC)COC(=O)CCCCCCCCCCCCCCC] |
| POP | 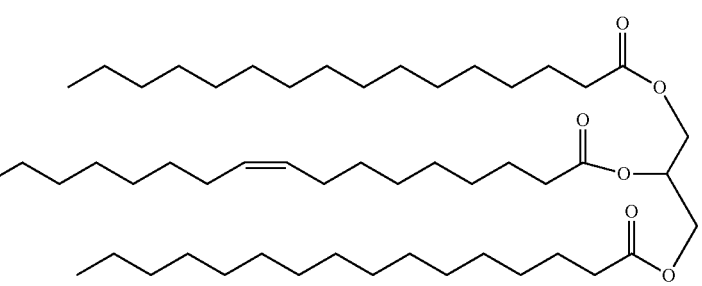 |
| POS | 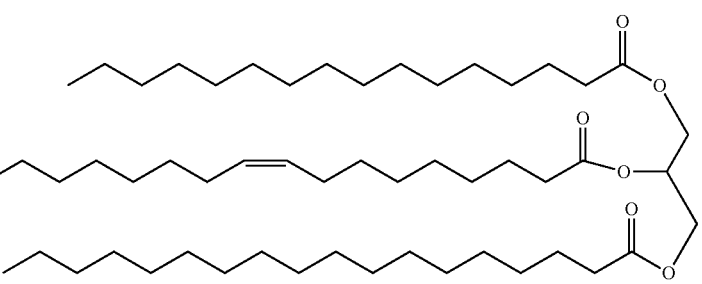 [SMILES: CC/C=C\CCCCCCCC(=O)OC(COC(=O)CCCCCCCCCCCCCCC)COC(=O)CCCCCCCCCCCCCCCCC] |
| PDS | 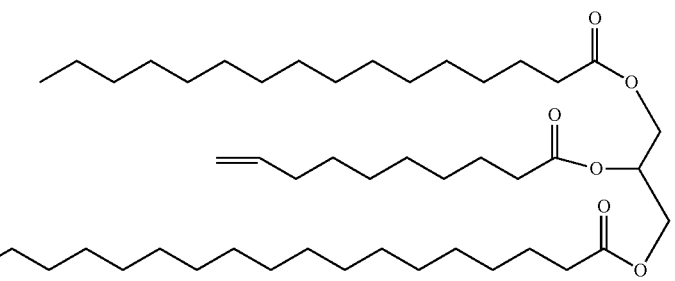 |
| PDdS | 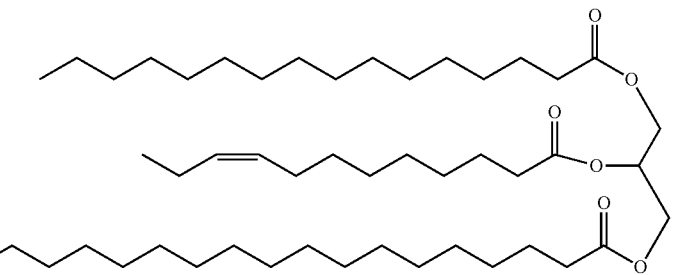 |

TABLE 3b-continued

Structures of potential TAGs in PMTAG

| Compound | Structure |
|---|---|
| PPM | (structure shown) |
| PPP | (structure shown) |
| PPS | (structure shown) |

Fatty Acid and TAG Profile of PMTAG

The fatty acid profile of the PMTAG was obtained by GC. Fatty acid profile was also determined using $^1$H-NMR data. TAG profile of PMTAG was investigated using HPLC. Three pure TAGs, namely 3-(stearoyloxy) propane-1,2-diyl bis(dec-9-enoate), or DSS, 3-(dec-9-enoyloxy) propane-1,2-diyldistearate or DDS, and 1,2,3-triyl tris(dec-9-enoate) or DDD were synthesized and used as standards to help in the determination of the TAG profile of the PMTAG.

GC of PMTAG Results

There are 36.9 wt. % unsaturated fatty acids, which includes the double bond of C10:1 in a terminal position (n=0 in Scheme 4). The double bond with n#0 contains trans- or/and cis-configurations. The GC detected less than 2 wt. % of polyunsaturated fatty acids and more than 60 wt. % saturated fatty acids. Note that the ratio of the trans-/cis-configuration depends on the reaction conditions, such as reaction temperature and catalyst.

HPLC of PMTAG Results

The HPLC curve recorded using the slow method described in the analytical methods section is shown in FIG. 1. As shown, an excellent separation was obtained. The

TABLE 4

GC results of methylated PMTAG. UFA: unsaturated fatty acids; SFA: saturated fatty acids

| UFA | | | | | | | | | | |
|---|---|---|---|---|---|---|---|---|---|---|
| C10:1 | C12:1 | C12:1 | C12:1 | C13:2 | C15:1 | C15:2 | C15:2 | C18:1 | C18:1 | C18:2 |
| Wt. % 17.52 | 0.28 | 9.13 | 2.04 | 0.91 | 0.58 | 0.22 | 0.29 | 2.97 | 2.80 | 0.17 |

| SFA | | | | | | |
|---|---|---|---|---|---|---|
| C12:0 | C14:0 | C16:0 | C18:0 | C20:0 | C21:0 | Others |
| Wt. % 0.31 | 1.24 | 50.35 | 9.28 | 0.35 | 0.12 | 1.28 | analysis of the HPLC of PMTAG was carried out with the help of pure synthesized TAGs (DDD, DSS and DDS) used as standards. The retention time of these standards were well matched with the related PMTAG fractions. The results of the analysis are reported in Table 5.

TABLE 5

HPLC analysis data of PMTAG

| Peak | Retention time (min) | Content (%) | Structure |
|---|---|---|---|
| 1 | 10.2 | 0.25 | DDD |
| 2 | 11.0 | 0.75 | — |
| 3 | 17.0 | 10.4 | — |
| 4 | 19.9 | 11.3 | DDS |
| 5 | 34.3 | 42.4 | — |
| 6 | 41.9 | 16.4 | — |
| 7 | 51.8 | <0.1 | DSS |
| 8 | 79.6 | 5.6% | — |

Figure 2A:
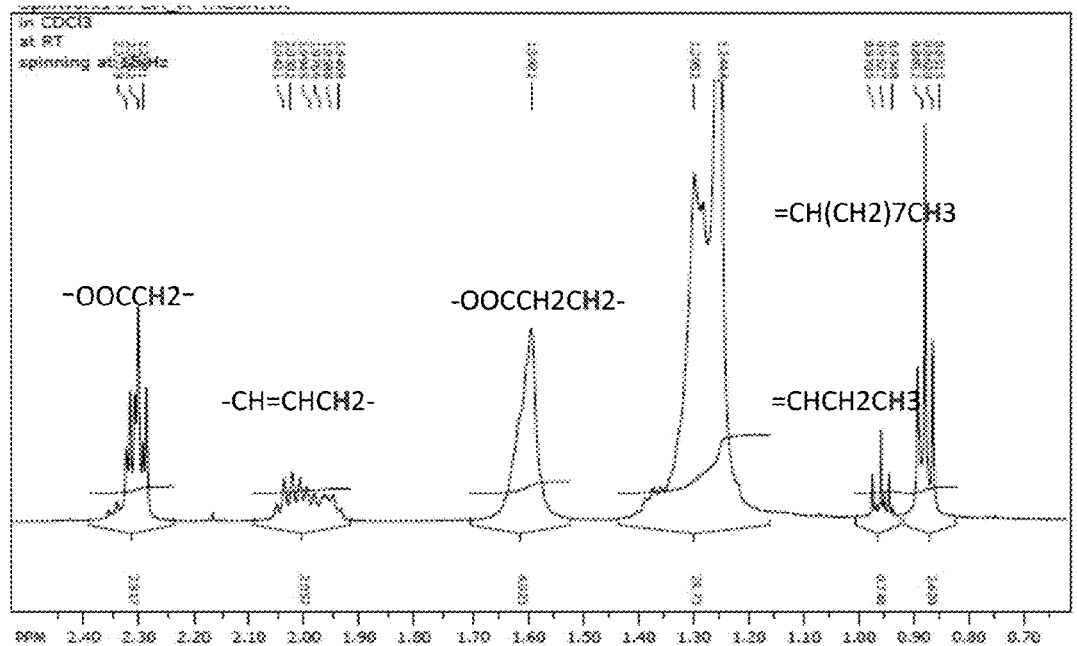
FIG. 2a depicts a $^1$H-NMR of PMTAG, with chemical shift range between δ 2.5 and 0.7 ppm.
Figure 2B:
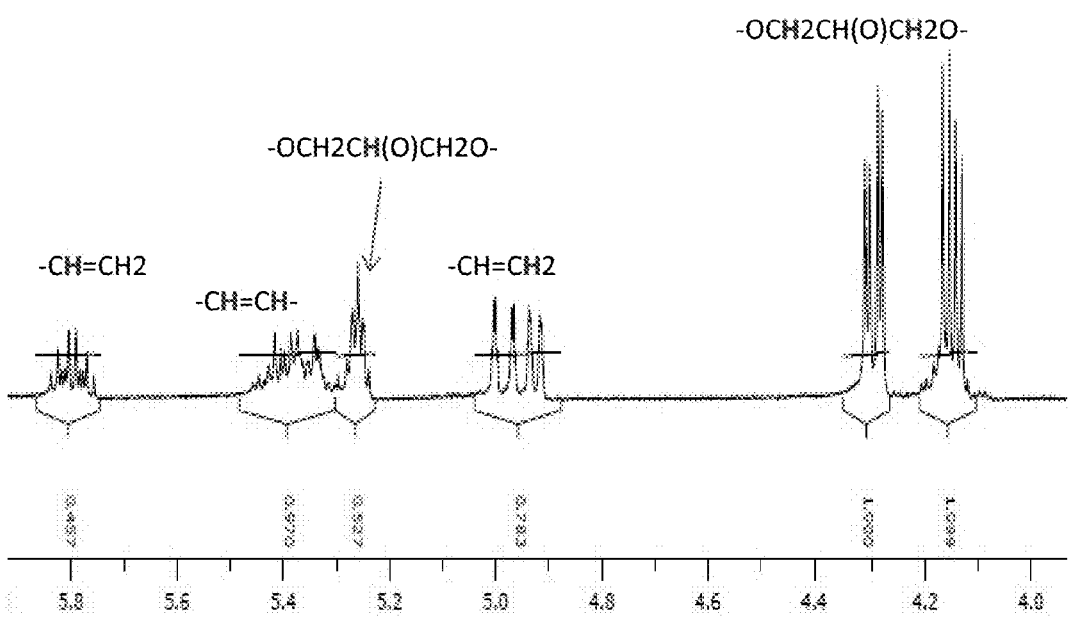
FIG. 2b depicts a $^1$H-NMR of PMTAG, with chemical shift range between δ 6.0 and 4.0 ppm.

$^1$H-NMR of PMTAG Results $^1$H-NMR spectra of PMTAG is shown in FIGS. 2a and 2b. The protons of the glycerol skeleton, —CH$_2$CH(O)CH$_2$— analysis was performed assuming that only TAG structures were present in the PMTAG. The fatty acid profile of PMTAG was calculated based on the relative area under the characteristic chemical shift peaks. The results are listed in Table 6.

TABLE 6

Fatty acid profile of PMTAG calculated based on the relative area under the characteristic NMR chemical shift peaks.

| Fatty Acids with: | Content (mol %) |
|---|---|
| —CH=CH2 | 24.9 |
| —CH=CHCH2CH3 | 15.8 |
| other non-terminal double bonds | 10.6-14.5 |
| Saturated fatty acid | 44.8-48.7 |

The possible structures of the PMTAG are presented in Scheme 4. These contain fatty acids with terminal double bonds, internal double bonds with n=2 or 8, as well as saturated fatty acids with m=11 to 20. PMTAG also contains saturated TAGs including PPP, PPM and PPS that exist in the starting natural oil.

Scheme 4. Possible structures composing PMTAG.

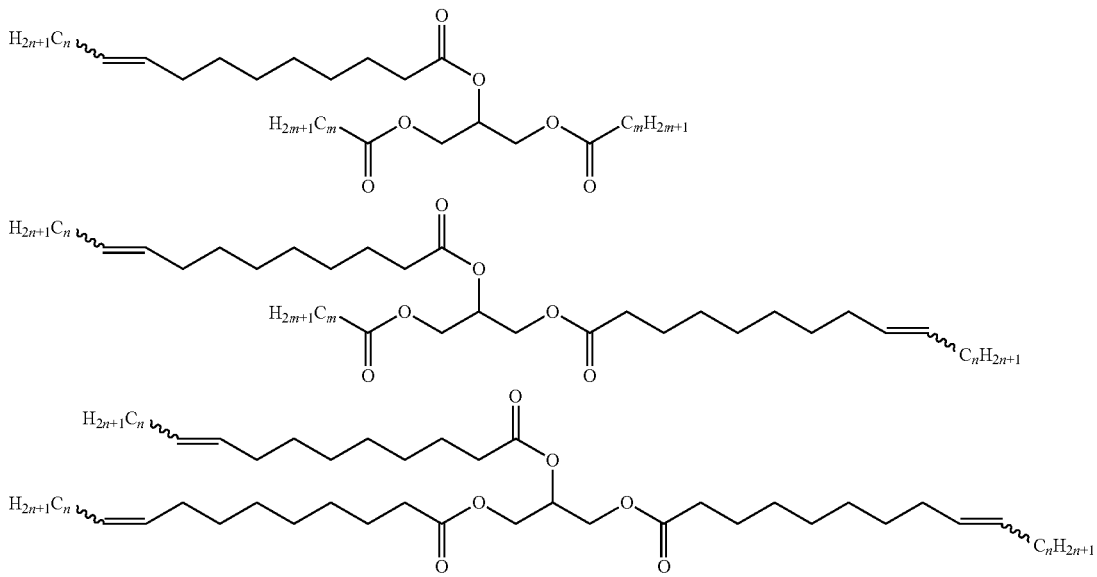

n = 0, 2, 8; m = 11 to 20.

and —OCH$_2$CHCH$_2$O— are clearly present at δ 5.3-5.2 ppm and 4.4-4.1 ppm, respectively. Two kinds of double bonds were detected: (1) terminal double bond (n=0), —CH=CH$_2$ and —CH=CH$_2$ present at δ 5.8 ppm and 5.0 to 4.9 ppm, respectively, and the internal double bond (n≠0), —CH=CH— at δ 5.5 ppm to δ 5.3 ppm. The ester group —C(=O)CH$_2$— was present at δ 2.33-2.28 ppm, α-H to —CH=CH— at δ 2.03-1.98 ppm, and —C(=O)CH$_2$CH$_2$— at δ 1.60 ppm. Two kind of —CH$_3$ were detected, one with n=2 at 1.0-0.9 ppm and another with n=8 at 0.9-0.8 ppm. Polyunsaturated fatty acids were not detected by NMR as the chemical shift at 2.6 to 2.8 ppm, the signature $^1$H-NMR of the proton between two double bonds in a polyunsaturated fatty acid was not presented.

Figure 3:
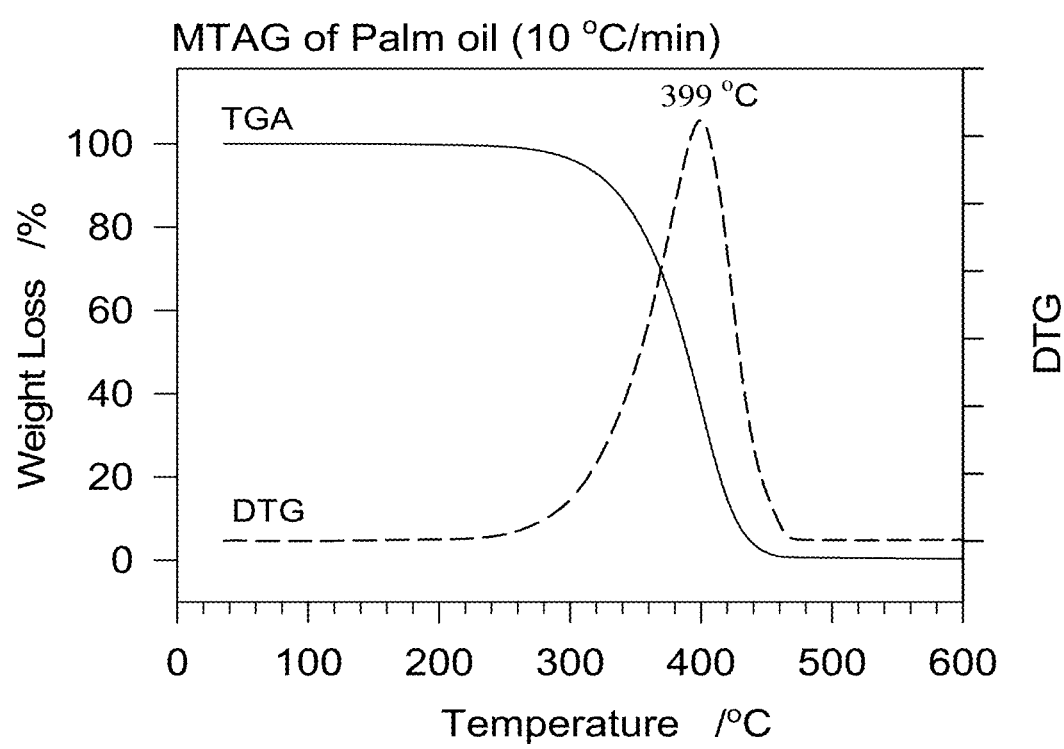
FIG. 3 depicts a TGA and DTG of PMTAG.

Due to the very low content of free fatty acid in the PMTAG material as indicated by the acid value (<1), the Physical Properties of PMTAG
Thermal Degradation of PMTAG The TGA and DTG profiles of the PMTAG are shown in the FIG. 3. TGA and DTG reveal one-step decomposition mechanisms for the PMTAG, associated with the breakage of the ester bonds. The onset of degradation of PMTAG as measured by the temperature at 1%, 5% and 10% decomposition was 260.3, 309.0 and 330.5° C., respectively. The extrapolated onset temperature is 333° C. As can be seen from the TGA curve and more precisely from the DTG curve, the decomposition ends at 470° C. The DTG peak occurs at 399.3° C. Nearly 60 wt % of the PMTAG decomposed at this temperature. The data indicates a thermal stability relatively higher than common commercial vegetable oils, such as olive, canola, sunflower and soybean oils, for which first DTG peaks as low as 325° C. have been detected.

Crystallization and Melting Behavior of PMTAG

Figure 4A:
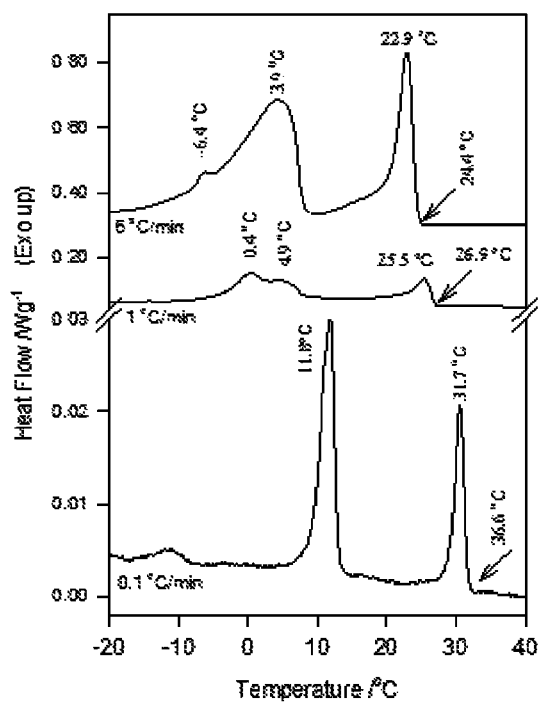
FIG. 4a depicts a DSC cooling (5.0, 1.0 and 0.1° C./min).
Figure 4B:
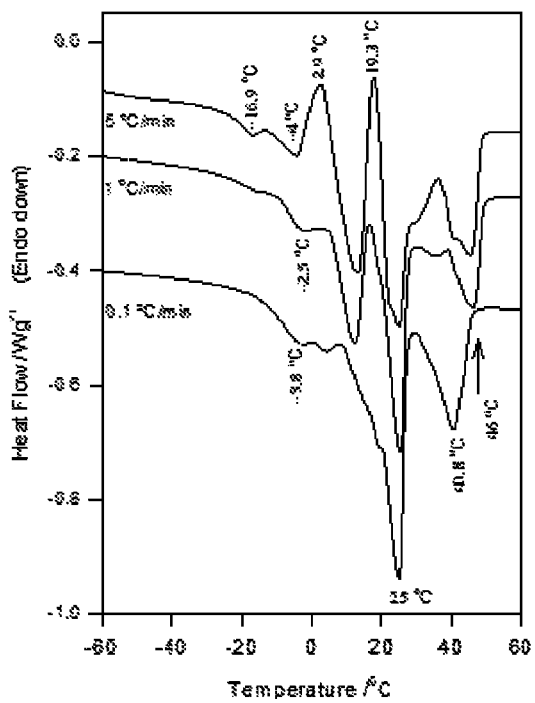
FIG. 4b depicts subsequent DSC heating (5° C./min) thermograms of PMTAG. Cooling rates for FIGS. 4a and 4b are reported at the left hand side above each curve and Peak temperatures are reported on the signal maximums.

The DSC thermograms obtained on cooling PMTAG at 5.0, 1.0 and 0.1° C./min and the thermograms obtained by subsequent heating at 5° C./min are presented in FIGS. 4a and 4b, respectively. The exothermic peaks presented in the cooling cycles became sharper and more defined as cooling rate was decreased. Three exotherms can be observed for the lowest cooling rate. The crystallization peak showing above room temperature (exotherm at ~32° C.) is associated with a high temperature fraction of the PMTAG, labelled PMTAG stearin, and the two crystallization peaks appearing below room temperature (exotherm at ~12° C.) and at sub-zero temperatures (exotherm at ~–11° C.) are associated with two lower temperature fractions of the PMTAG, labelled collectively PMTAG olein, similar to their palm oil counterparts. The first two fractions were dominantly present as indicated by their relative enthalpy of crystallization of 28.5 J/g and 60.1 J/g (15% and 32% of the total enthalpy, respectively).

At least six endotherm and two resolved exotherms were observed in the DSC heating thermograms of PMTAG outlining that the material is polymorphic. Although not apparent in the DSC heating thermogram obtained at 0.1° C./min, the last endotherm (at ~41° C., FIG. 4b) is indicative of a phase that was recrystallized during the heating process and subsequently melted. The recorded enthalpy of heating, calculated from the area of the endotherms (109.7 J/g), was much lower than the total enthalpy of crystallization (186.1 J/g), indicating a competition of exothermic and endothermic events during heating which is the result of recrystallization mediated by melt.

The endotherms observed below 30° C. are associated with the melting of PMTAG olein and the endotherms observed above are associated with the melting of PMTAG stearin. As shown in FIG. 4b, the melting of the PMTAG olein and PMTAG stearin were not fully resolved, indicating that a dry fractionation is only possible by using very slow cooling.

Solid Fat Content of PMTAG

Figure 5A:
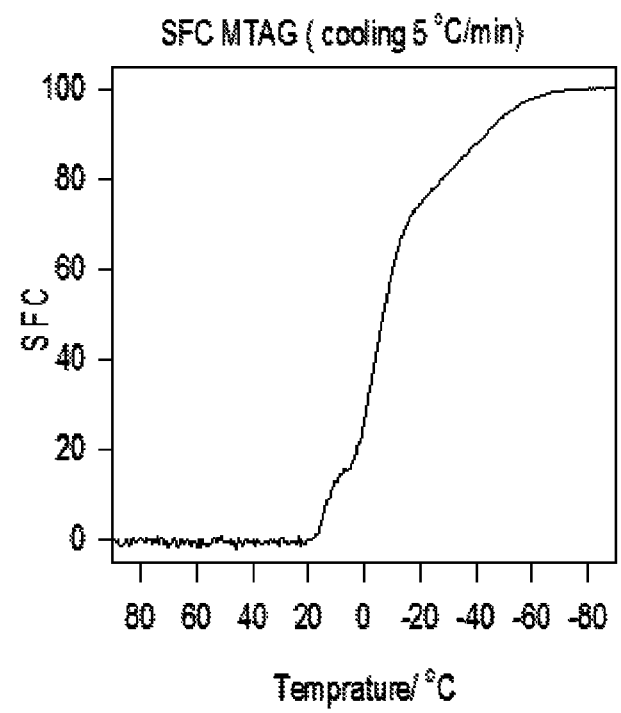
FIG. 5a depicts SFC versus temperature of PMTAG obtained during cooling at 5° C./min.
Figure 5B:
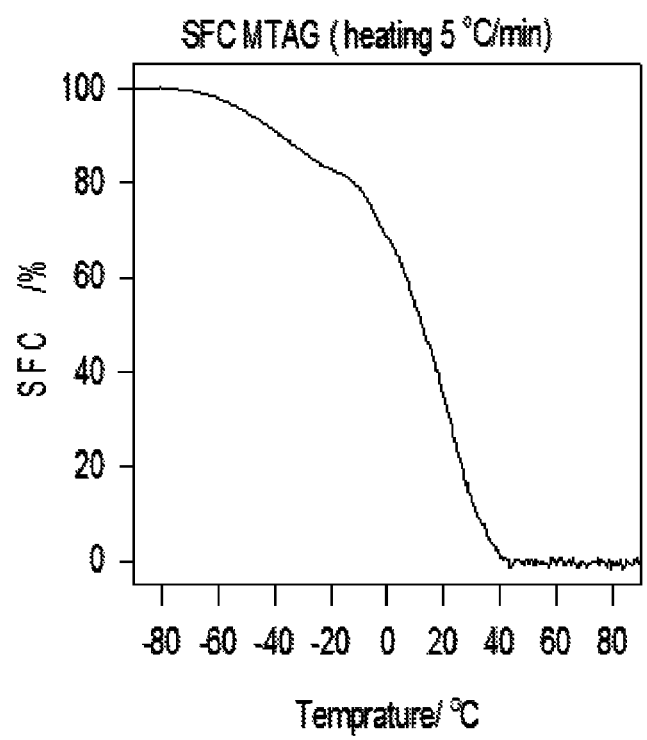
FIG. 5b depicts the subsequent heating at 5° C./min of PMTAG.

Solid Fat Content (SFC) versus temperature profiles of PMTAG during cooling (5° C./min) and heating (5° C./min) are shown in FIGS. 5a and 5b, respectively. As can be seen in FIG. 5a, the SFC cooling curve presented three segments indicative of a three-step solidification process. The first SFC segment can be associated with PMTAG stearin and the two others to PMTAG olein, similar to the exothermic events observed in the DSC.

Microstructure of PMTAG Evolution

The microstructural analysis was performed in order to determine the microstructure size, shape, development kinetics and final network formation. The development of the microstructure was followed while the sample was cooling at 5° C./min.

FIGS. 6a-6f highlight the development of the microstructure of the PMTAG during cooling at 5° C./min. Crystallization initiated at ~26.1±0.5° C. with very small crystals of average size 20±5 µm. The same type of crystals developed from 26° C. to 14° C. Crystal development was relatively fast. From 14 to 5° C. no development was observed. Secondary nucleation initiated at ~5.0±0.5° C. and several small fibril-like crystals developed at this temperature and continued to develop below 0° C. The different modes of crystallization indicated by both DSC and SFC are reflected in the microstructure development as different types of microstructure evolved following secondary nucleation.

The microstructure analysis also supports that the 5° C./min rate does not allow a microstructure suitable for fractionation to be developed. Higher cooling rates may lead to the formation of very small microstructures, a situation which is maintained by PMTAG, as evidenced by FIGS. 6e-6f.

Flow Behavior and Viscosity of PMTAG

Figure 7A:
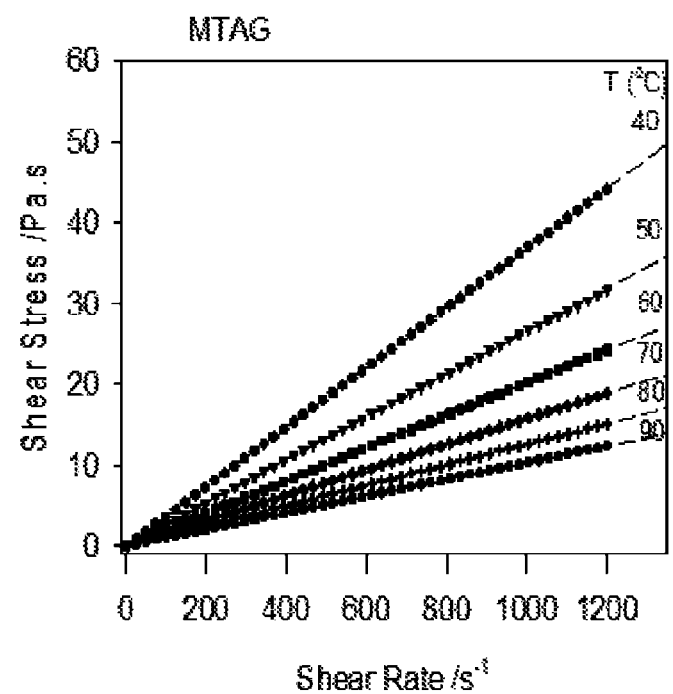
FIG. 7a depicts a heat rate versus shear stress curves of PMTAG showing Newtonian behavior.
Figure 7B:
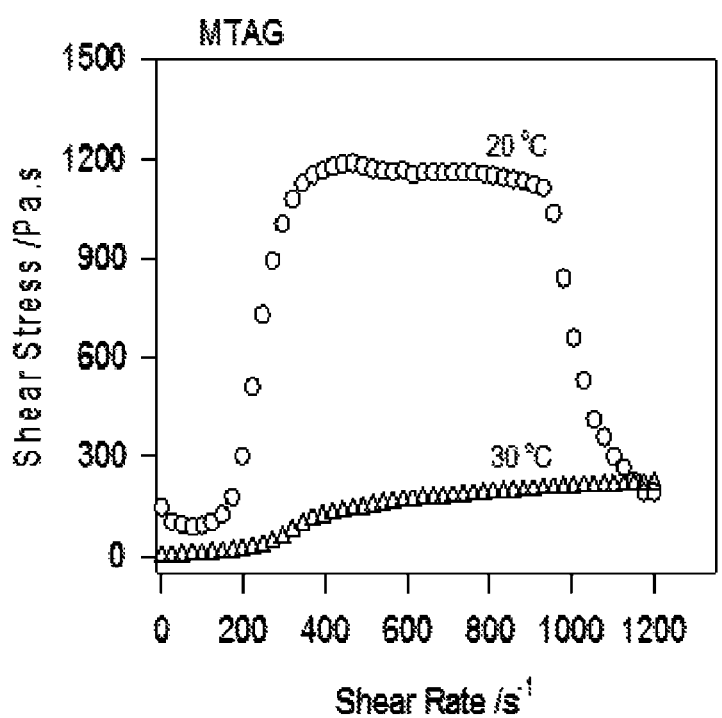
FIG. 7b depicts the heat rate versus shear stress curves of PMTAG showing non-Newtonian behavior.
Figure 8:
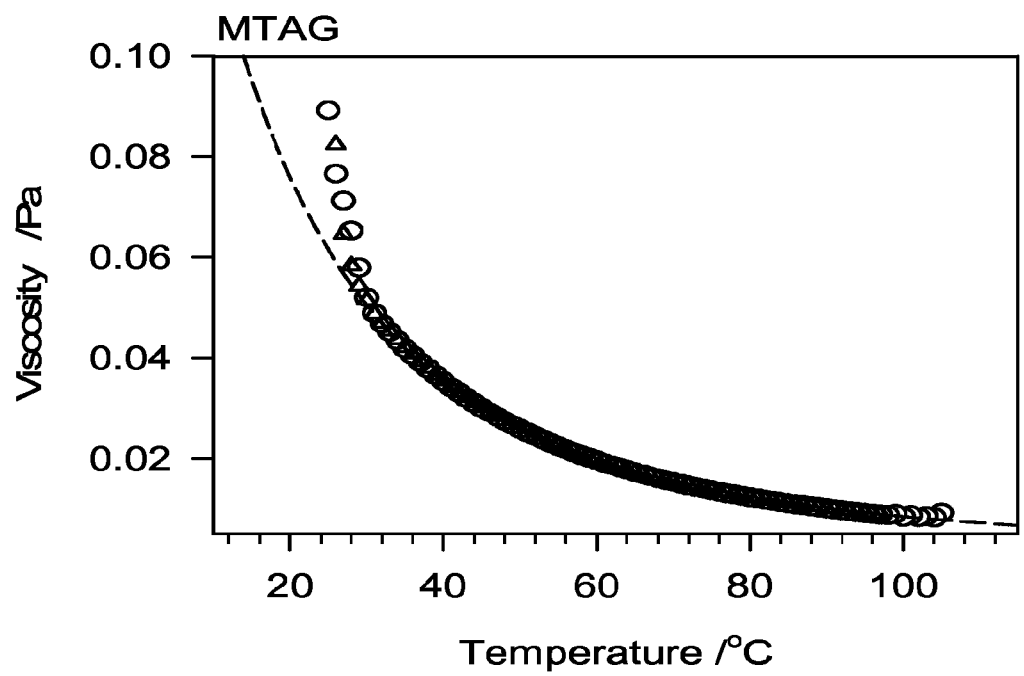
FIG. 8 depicts a viscosity versus temperature curve obtained during cooling of PMTAG at (○) 3° C./min and (Δ) 1° C./min. Dashed lines are a guide for the eye.

FIG. 7 shows the flow behavior of PMTAG. Shear rate-shear stress curves of PMTAG obtained at different temperatures are displayed in (FIGS. 7a and 7b). FIG. 8 show the viscosity versus temperature curves obtained during cooling of PMTAG at 3° C./min and 1° C./min. The application of the Herschel-Bulkley equation (Eq. 1) to share rate-shear stress data obtained for the PMTAG at temperatures between 40° C. and 90° C. ($R^2>0.9999$) generated power index values (n) all approximately equal to unity, indicating Newtonian behavior. Fits to the Herschel-Bulkley (eq. 1) model are included in FIG. 7a. The data collected at 30° C. and below (FIG. 7b), indicated that the sample started crystallizing at this temperature, in good correspondence with DSC. The flow behavior observed for PMTAG is very similar to that of vegetable oils.

The viscosity versus temperature of PMTAG obtained using the ramp procedure in the range of temperatures where it was in the liquid state presented the exponential behavior of liquid hydrocarbons.

B. Polyols from PMTAG

Synthesis of Polyols from PMTAG

The synthesis of the PMTAG polyol involves epoxidation and subsequent hydroxylation of a MTAG of a natural oil, e.g., palm oil. Any peroxyacid may be used in the epoxidation reaction, and this reaction will convert a portion of or all of the double bonds present in the PMTAG to epoxide groups. Peroxyacids (peracids) are acyl hydroperoxides and are most commonly produced by the acid-catalyzed esterification of hydrogen peroxide. Any suitable peroxyacid may be used in the epoxidation reaction. Examples of hydroperoxides that may be used include, but are not limited to, hydrogen peroxide, tert-butylhydroperoxide, triphenylsilylhydroperoxide, cumylhydroperoxide, trifluoroperoxyacetic acid, benzyloxyperoxyformic acid, 3,5-dinitroperoxybenzoic acid, and m-chloroperoxybenzoic acid. The peroxyacids may be formed in-situ by reacting a hydroperoxide with the corresponding acid, such as formic or acetic acid. Other organic peracids may also be used, such as benzoyl peroxide, and potassium persulfate. The epoxidation reaction can be carried out with or without solvent. Commonly used solvents in the epoxidation may be chosen from the group including but not limited to aliphatic hydrocarbons (e.g., hexane and cyclohexane), organic esters (e.g., ethyl acetate), aromatic hydrocarbons (e.g., benzene and toluene), ethers (e.g., dioxane, tetrahydrofuran, ethyl ether, tert-butyl methyl ether) and halogenated hydrocarbons (e.g., dichloromethane and chloroform).

Subsequent to the epoxidation reaction, the reaction product may be neutralized. A neutralizing agent may be added to neutralize any remaining acidic components in the reaction product. Suitable neutralizing agents include weak bases, metal bicarbonates, or ion-exchange resins. Non-limiting examples of neutralizing agents that may be used include ammonia, calcium carbonate, sodium bicarbonate, magnesium carbonate, amines, and resin, as well as aqueous solutions of neutralizing agents. Subsequent to the neutralization, commonly used drying agents may be utilized. Such drying agents include inorganic salts (e.g. calcium chloride, calcium sulfate, magnesium sulfate, sodium sulfate, and potassium carbonate).

After the preparation of the epoxidized PMTAG, the next step is to ring-open at least a portion of the epoxide groups via a hydroxylation step. In the present effort, all of the epoxide groups were opened. The hydroxylation step includes reacting the oxirane ring of the epoxide in an aqueous or organic solvent in the presence of an acid catalyst in order to hydrolyze the oxirane ring to a dihydroxy intermediate. In some aspects, the solvent may be water, aliphatic hydrocarbons (e.g., hexane and cyclohexane), organic esters (e.g., ethyl acetate), aromatic hydrocarbons Synthesis of PMTAG Polyol PMTAG Polyol was prepared in a two-step reaction: epoxidation by formic acid (or acetic acid) and $H_2O_2$, followed by a hydroxylation using $HClO_4$ as a catalyst, as described in Scheme 5. The reaction conditions were optimized for both of the epoxidation and hydroxylation steps with respect to the amount of catalyst, the type of solvent and the reaction temperature. The detailed information is presented in Table 7.

Scheme 5. Synthesis of PMTAG Polyol

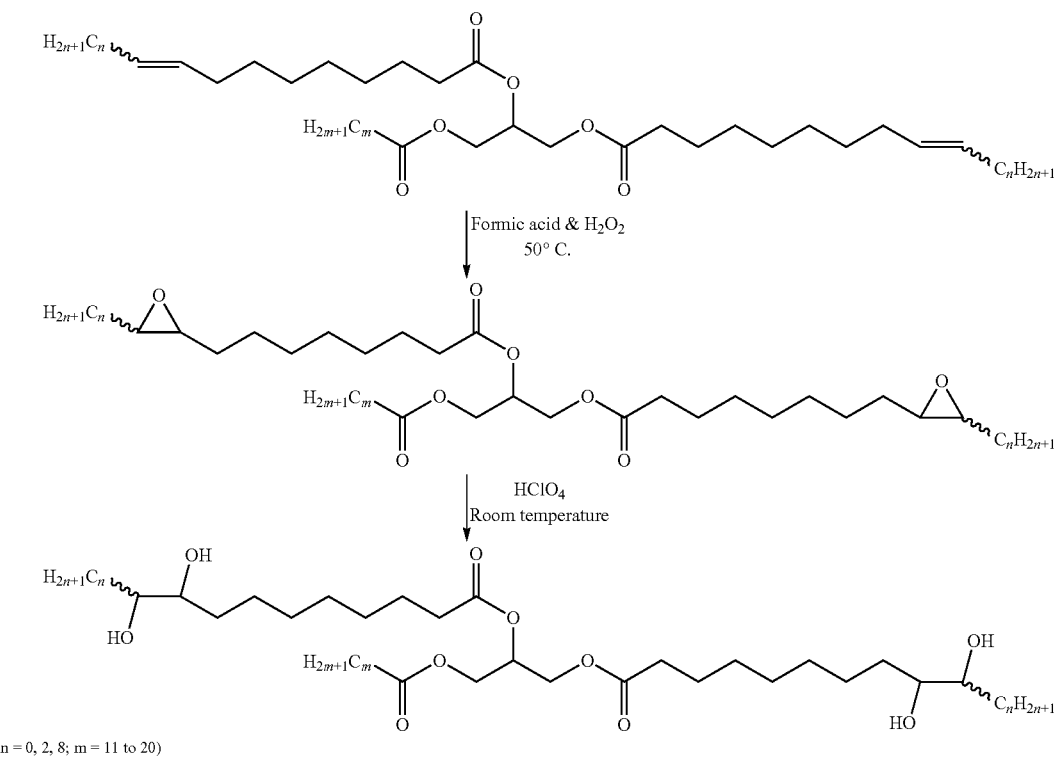

(n = 0, 2, 8; m = 11 to 20)

(e.g., benzene and toluene), ethers (e.g., dioxane, tetrahydrofuran, ethyl ether, tert-butyl methyl ether) and halogenated hydrocarbons (e.g., dichloromethane and chloroform), and combinations thereof (e.g., water and tetrahydrofuran). In some aspects, the hydroxylation step can be carried out without solvent. The acid catalyst may be an acid such as sulfuric, pyrosulfuric, perchloric, nitric, halosulfonic acids such as fluorosulfonic, chlorosulfonic or trifluoromethane sulfonic, methane sulfonic acid, ethane sulfonic acid, ethane disulfonic acid, benzene sulfonic acid, or the benzene disulfonic, toluene sulfonic, naphthalene sulfonic or naphthalene disulfonic acids. As needed, subsequent washing steps may be utilized, and suitable drying agents (e.g., inorganic salts) may be used.

Materials for PMTAG Polyol Synthesis

Formic acid (88 wt %) and hydrogen peroxide solution (30 wt %) were purchased from Sigma-Aldrich and perchloride acid (70%) from Fisher Scientific. Hexane, dichloromethane, ethyl acetate and tetrahydrofuran were purchased from ACP chemical Int. (Montreal, Quebec, Canada) and were used without further treatment.

Epoxidation Procedure

Formic acid (88%; 200 g) was added to a solution of PMTAG (200 g) in dichloromethane (240 mL). This mixture was cooled to 0° C. Hydrogen peroxide (30% 280 g) was added dropwise. The resulting mixture was stirred at 50° C., and the progress of the reaction was monitored by a combination of TLC and $^1$H-NMR. The reaction was completed after 48 to 50 hours.

Upon completion, the reaction mixture was diluted with 250 mL dichloromethane, washed with water (200 mL×2), and then with saturated sodium hydrogen carbonate (200 mL×2), and water again (200 mL×2), then dried over anhydrous sodium sulfate. After removing the drying agent by filtration, solvent was removed by roto-evaporation. The crude epoxide was used for the hydroxylation.

$^1$H-NMR Results of Epoxidized PMTAG

Figure 9:
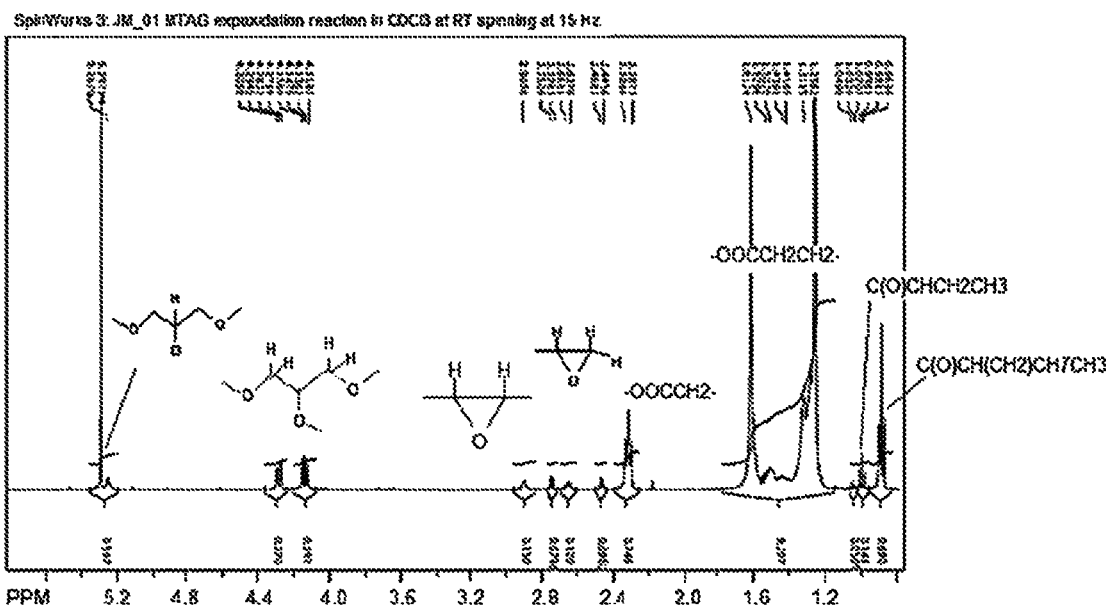
FIG. 9 depicts a $^1$H-NMR spectrum of epoxidized PMTAG.

The $^1$H-NMR of epoxidized PMTAG is shown in FIG. 9. The protons of the glycerol skeleton, —$CH_2CH(O)CH_2$— and —$OCH_2CHCH_2O$— are present at δ 5.3-5.2 ppm and 4.4-4.1 ppm, respectively; —C(=O)$CH_2$— at δ 2.33-2.28 ppm; α-H to —CH=CH— at δ 2.03-1.98 ppm; and —C(=O)$CH_2CH_2$— at δ 1.60 ppm. There are two types of —CH$_3$, one with n=2 and another with n=8. The first presented a proton at δ=1.0-0.9 ppm, and the second a proton at 0.9-0.8 ppm. The chemical shift at 5.8, 5.4 and 5.0 ppm, characteristic of double bonds, disappeared, whereas, the chemical shift at 2.85 ppm, related to non-terminal epoxy ring, and the chemical shift at 2.7 to 2.4 ppm, related to terminal epoxy ring, appeared, indicating that the epoxidation reaction was successful and complete.

Hydroxylation Procedure

Approximately 200 g crude epoxy PMTAG was dissolved into a 500 mL solvent mixture of THF/H$_2$O (3:2) containing 14.5 g perchloric acid. The reaction mixture was stirred at room temperature and the progress of the reaction was monitored by a combination of TLC and $^1$H-NMR. The reaction was completed after 36 h. The reaction mixture was poured into 240 mL water and extracted with CH$_2$Cl$_2$ (2×240 mL). The organic phase was washed by water (2×240 mL), followed by 5% aqueous NaHCO$_3$ (2×200 mL) and then water (2×240 mL) again. The organic phase was then dried over Na$_2$SO$_4$. After removing the drying agent by filtration, the solvent was removed with a rotary evaporator and further dried by vacuum overnight, giving a light yellow grease-like solid.

Optional Hydroxylation Procedure 50 g epoxidized PMTAG was suspended in 250 mL water. 6 g HClO$_4$ (70%) was added into reaction mixture. The reaction mixture was heated to reflux for 6 h. The mixture was then poured into 1 L water. The mixture was kept at room temperature overnight to solidify the product. The solid polyol was collected by filtration and then dried under vacuum at 60° C.

Optimization of Synthesis of PMTAG Polyol

To reduce the cost and to achieve a greener chemical route the synthesis of PMTAG Polyol was optimized. The optimization was mainly focused on reducing the amount of formic acid, hydrogen peroxide, perchloric acid and using greener solvents in both epoxidation and hydroxylation reaction. The reaction progress was monitored by TLC and $^1$H-NMR. The achieved products were analyzed using HPLC and $^1$H-NMR. The detailed information is listed in Table 7. As seen in Table 7, the epoxidation of PMTAG was effective and complete when DCM (dichloromethane) was used as solvent, but not when THF, Ethyl Acetate and H$_2$O were used as solvent, especially for terminal double bonds. Furthermore, a by-product having a formic acid unit attached on the fatty acid backbone was detected when ethyl acetate and water were used as solvent. Any of these other methods may be used satisfactorily in an industrial process to produce PMTAG Polyol, depending on the requirements of the end polyurethane product.

Figure 10:
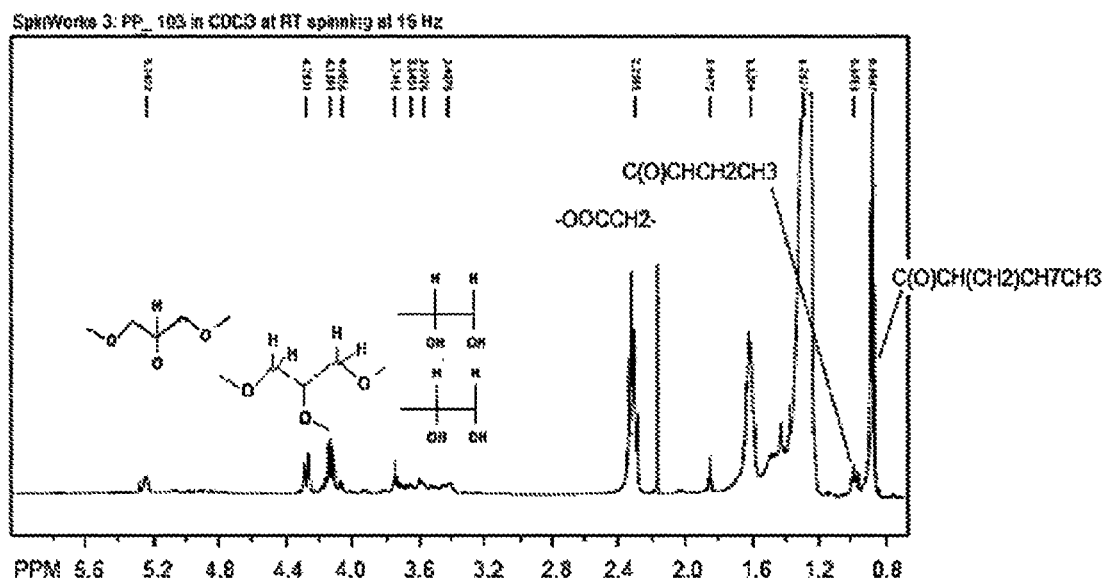
FIG. 10 depicts a $^1$H-NMR of PMTAG Polyol 100%.

The hydroxylation of the epoxidized PMTAG was carried out either in a mixture of THF and water or water only. When a mixture of THF and water was used as solvent, the hydroxylation was carried out at room temperature and 50° C. The reaction performed at 50° C. produced polyols with higher acid values. The weight ratio of perchloric acid/PMTAG was optimized in the hydroxylation reaction performed with THF and water as solvent (see Table 7). For a ratio of 1:1, the polyol (so-called polyol 100%) displayed a higher acid value and lower OH number (Table 7). Its NMR spectrum (FIG. 10) indicated that the TAG-like glycerol backbone was lost, a sign that the hydrolysis of the ester link in TAG occurred.

When the ratio was reduced to 0.1:1 and 0.05:1, the polyols (so called polyol 10% or polyol 5%, respectively) displayed much lower acid value and higher OH number (Table 7). A TAG-like glycerol backbone was shown in the NMR spectra of PMTAG Polyol 10% and 5% (FIG. 11), indicating that the hydrolysis of the ester link in TAG was avoided.

The hydroxylation of epoxidized PMTAG in H$_2$O was also carried out. The reaction time was found to be highly dependent on the acid/PMTAG ratio. When the acid/PMTAG ratio increased from 0.012 to 0.18, the reaction time decreased from 32 hours to 2 hours. When compared with the PMTAG Polyol prepared using THF and H$_2$O as solvent, the polyol prepared using H$_2$O as solvent presented a lower OH number but the same acid value, indicating that polyol oligomers were formed during the hydroxylation reaction.

TABLE 7

Optimization parameters of synthesis of PMTAG Polyol and results achieved. Concentration of H$_2$O$_2$ was 30%; concentration of formic acid was 88%; the ratio listed for the starting materials is based on the 30% H$_2$O$_2$ solution and 88% formic acid solution.

| Step | Ratio of starting materials (w/w) | Solvent | T (° C.) | Time (hrs) | Note |
|---|---|---|---|---|---|
| Epoxidation | PMTAG/Formic acid/H$_2$O$_2$ = 1/1/1.4 | DCM | 50 | 48 | Good and completed |
| | | THF | 50 | 72 | Not completed, more than 60% terminal double bonds remained |
| | | Ethyl acetate | 50 | 72 | Not completed and there were by-products |
| | | No solvent | 50, 70, 100 | 72 | Not completed, more than 50% terminal double bonds remained; there were by products at 100° C. |
| | | No solvent | 60; exothermic; self-heated to 100° C. | 24 | No double bond detected; Formic ester polyol was formed |
| | PMTAG/Formic acid/H$_2$O$_2$ = 1/0.3/1 | DCM | 50 | 72 | Not completed for both terminal and internal double bonds |

TABLE 7-continued

Optimization parameters of synthesis of PMTAG Polyol and results achieved. Concentration of $H_2O_2$ was 30%; concentration of formic acid was 88%; the ratio listed for the starting materials is based on the 30% $H_2O_2$ solution and 88% formic acid solution.

| Step | Ratio of starting materials (w/w) | Solvent | T (° C.) | Time (hrs) | Note |
|---|---|---|---|---|---|
| | PMTAG/Formic acid/$H_2O_2$ = 1/0.2/1 | DCM | 50 | Over 1 week | Not completed for both terminal and internal double bonds |
| Hydroxylation | PMTAG/HClO$_4$ = 1/1 (Polyol 100%) | THF + $H_2O$ | RT | 20 | High acid value(>50) OH value ~120 |
| | PMTAG/HClO$_4$ = 1/0.1 (Polyol 10%) | THF + $H_2O$ | RT | 48 | Low acid value (~6) OH value ~150 |
| | PMTAG/HClO$_4$ = 1/0.05 (Polyol 5%) | THF + $H_2O$ | RT | 48 | Low acid value (~6) OH value ~150 NMR is same as polyol 10% |
| | PMTAG/HClO$_4$ = 1/0.08 | $H_2O$ | Reflux | 5 to 6 | Low acid value (~7) OH value ~130 NMR and HPLC is same as polyol 5% |
| | PMTAG/HClO$_4$ = 1/0.18 | $H_2O$ | Reflux | 2 | NMR and HPLC are similar to polyol 5% |
| | PMTAG/HClO$_4$ = 1/0.012 | $H_2O$ | Reflux | 32 | NMR and HPLC similar to 5% polyol |

Figure 11:
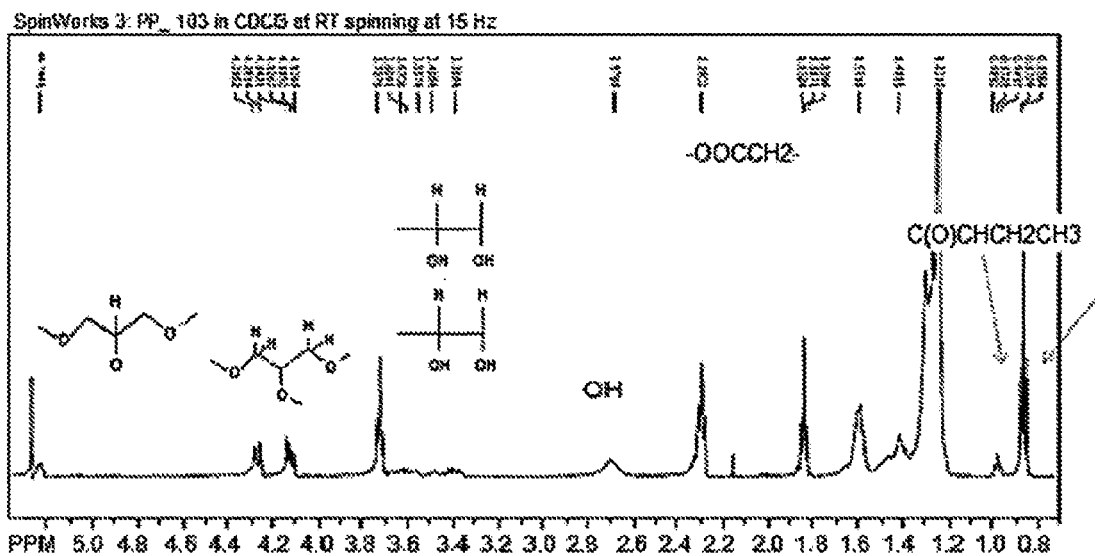
FIG. 11 depicts a $^1$H-NMR spectrum of PMTAG Polyol 5% and 10%.
Figure 12:
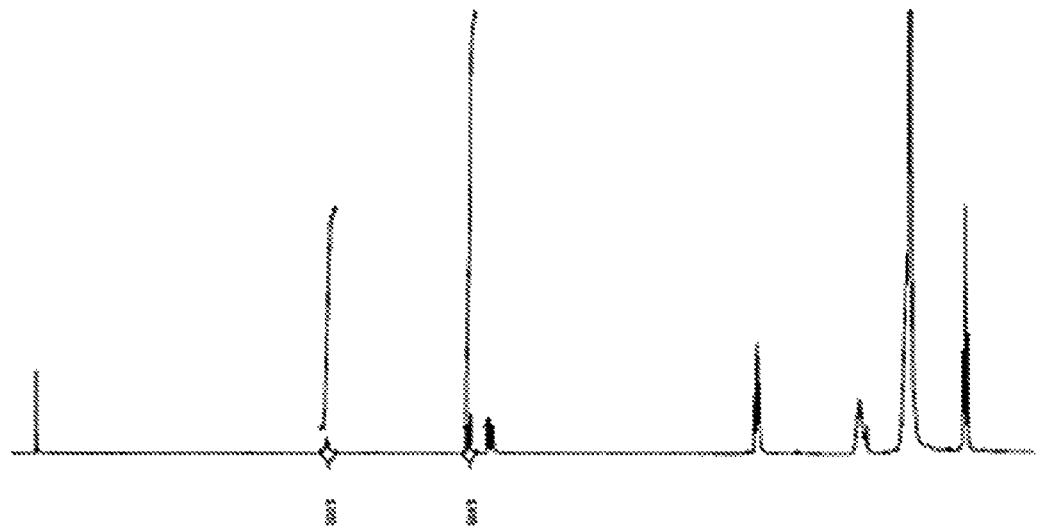
FIG. 12 depicts a $^1$H-NMR of Fraction 1.
Figure 13:
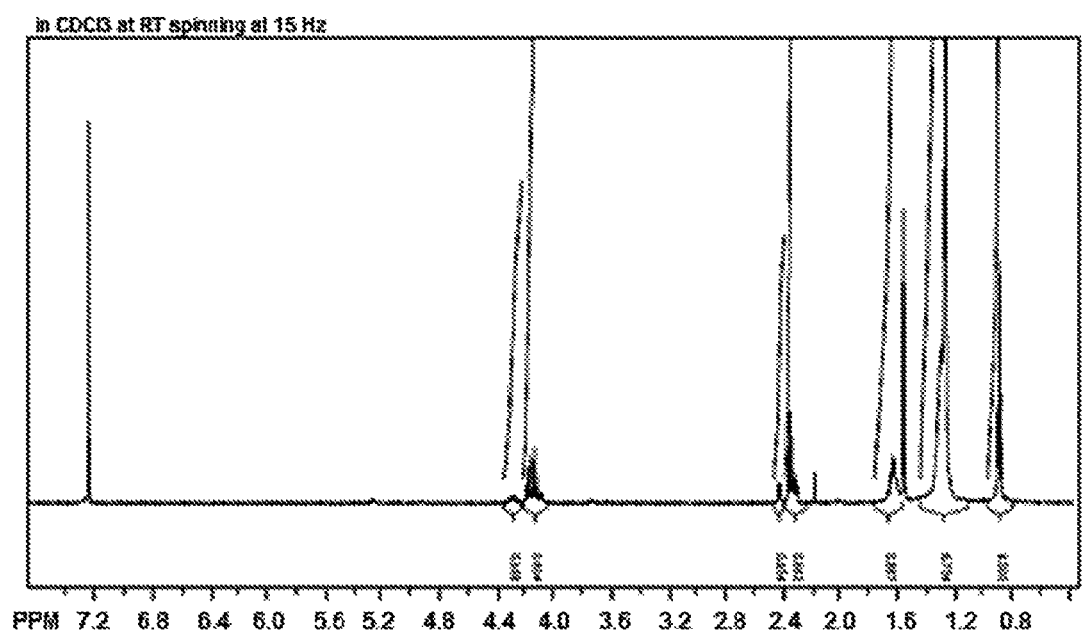
FIG. 13 depicts a $^1$H-NMR of Fraction 2.
Figure 14:
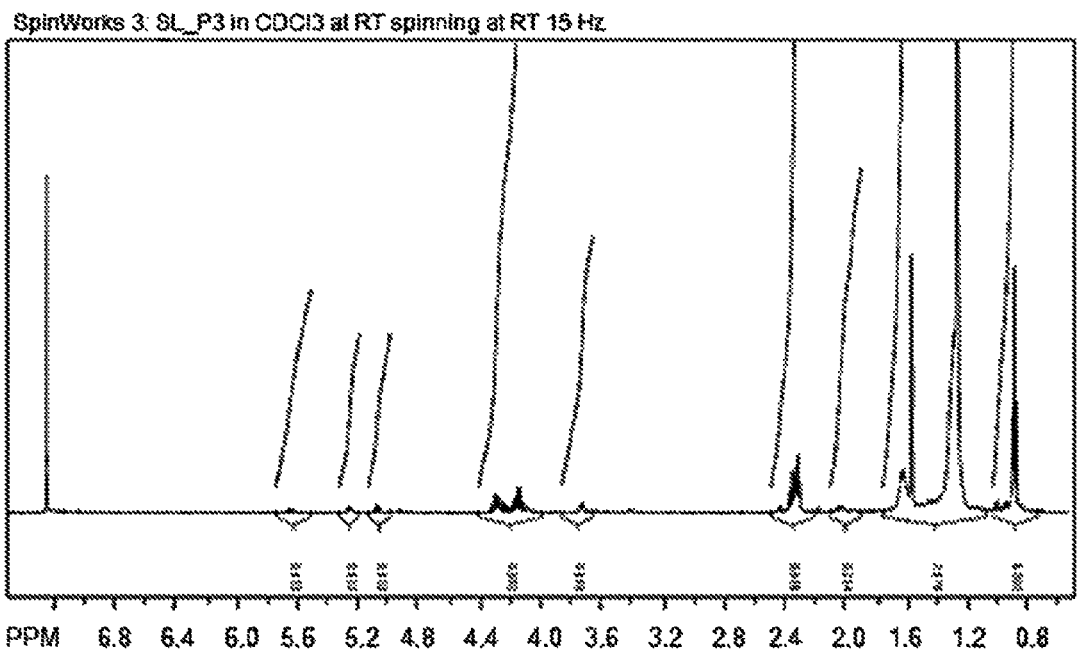
FIG. 14 depicts a $^1$H-NMR of Fraction 3.
Figure 15:
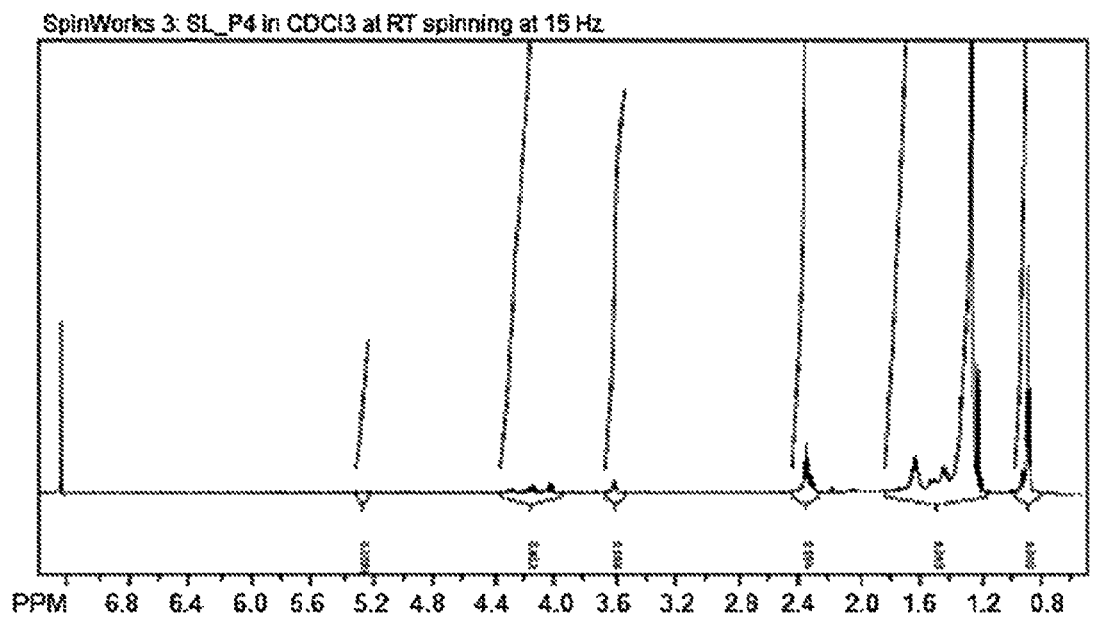
FIG. 15 depicts a $^1$H-NMR of Fraction 4.
Figure 16:
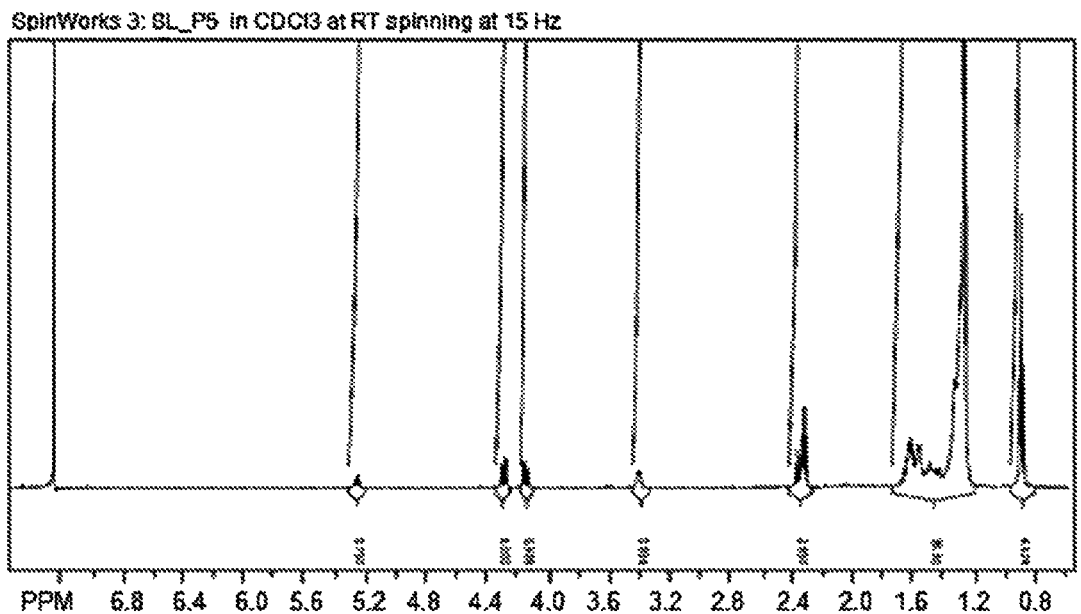
FIG. 16 depicts a $^1$H-NMR of Fraction 5.
Figure 17:
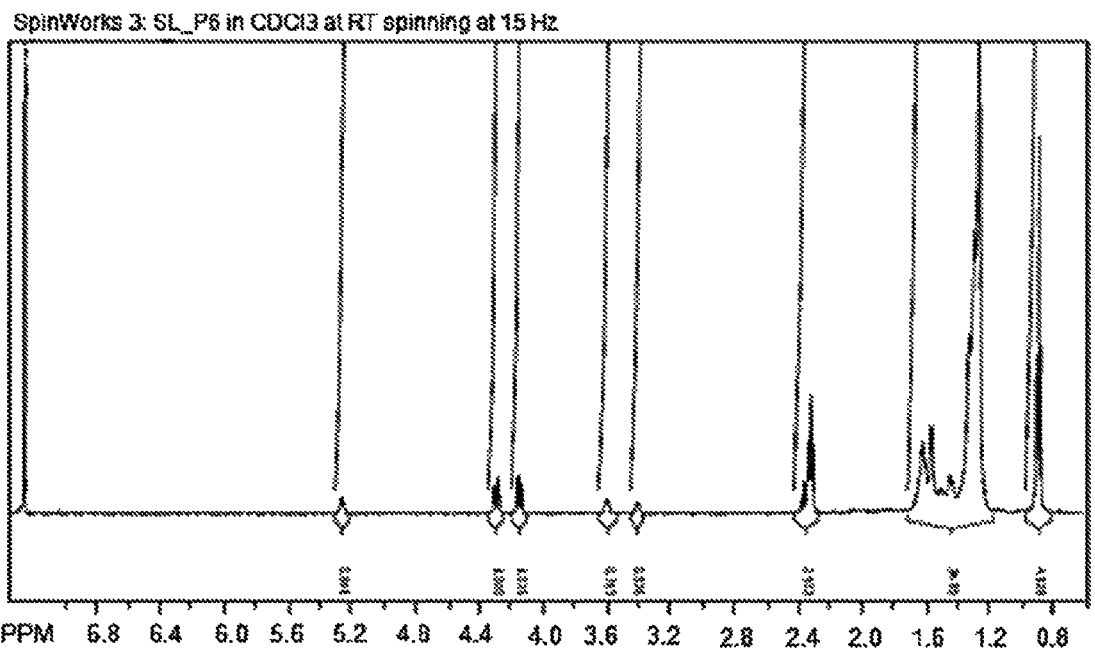
FIG. 17 depicts a $^1$H-NMR of Fraction 6.
Figure 18:
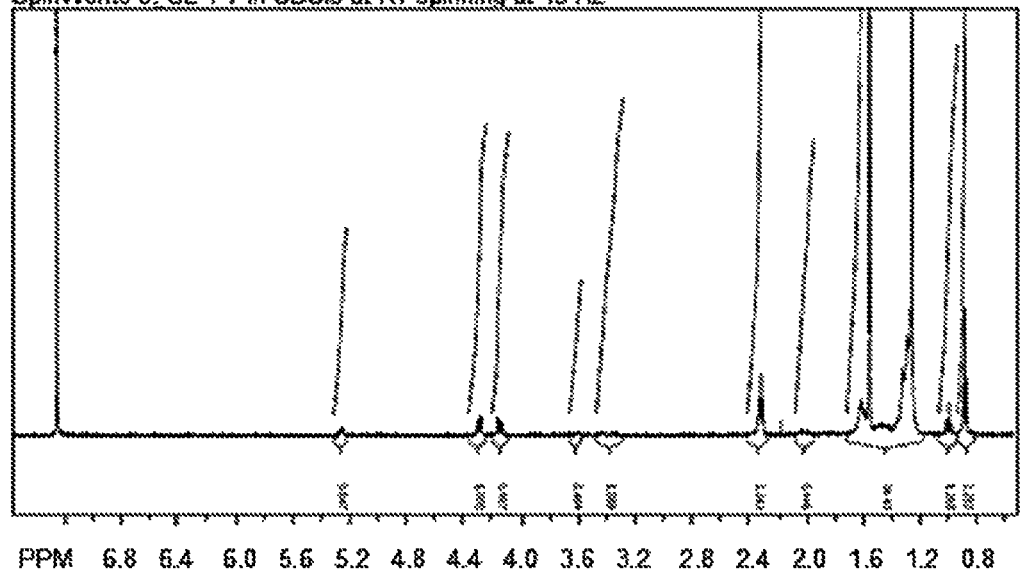
FIG. 18 depicts a $^1$H-NMR of Fraction 7.
Figure 19:
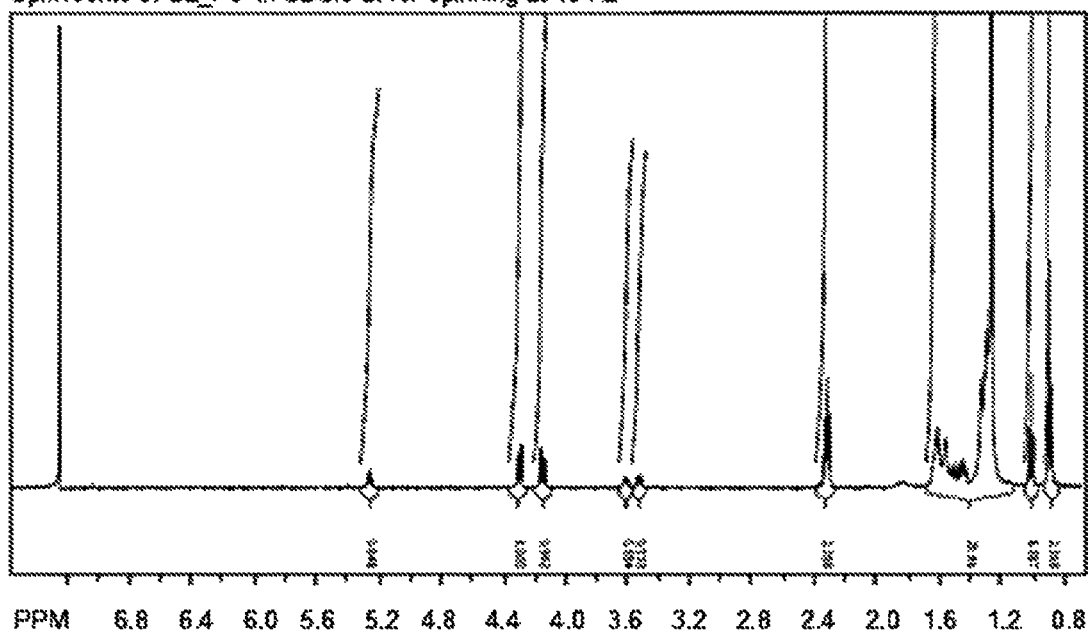
FIG. 19 depicts a $^1$H-NMR of Fraction 8.
Figure 20:
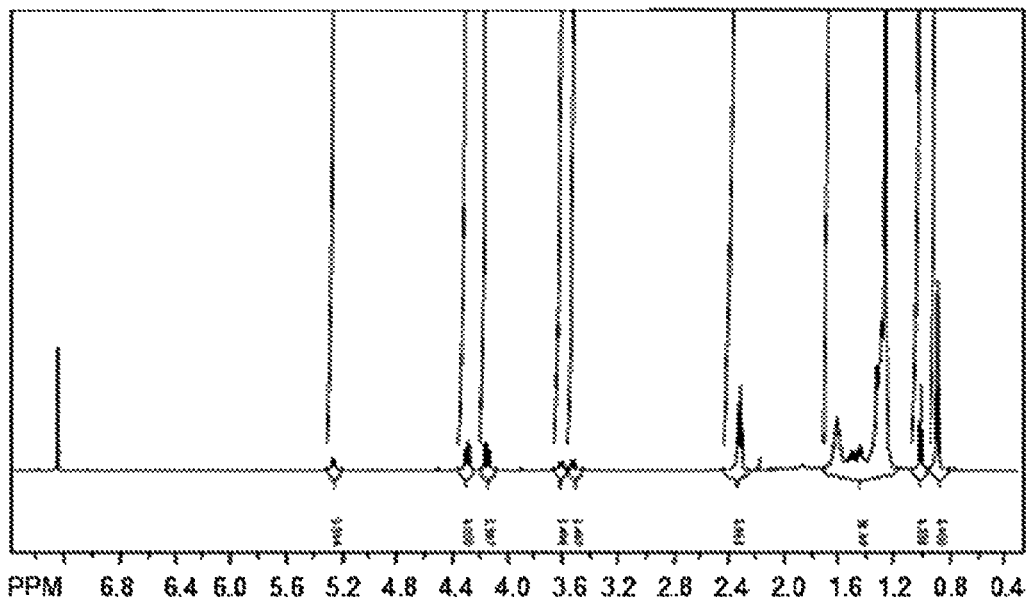
FIG. 20 depicts a $^1$H-NMR of Fraction 9.
Figure 21:
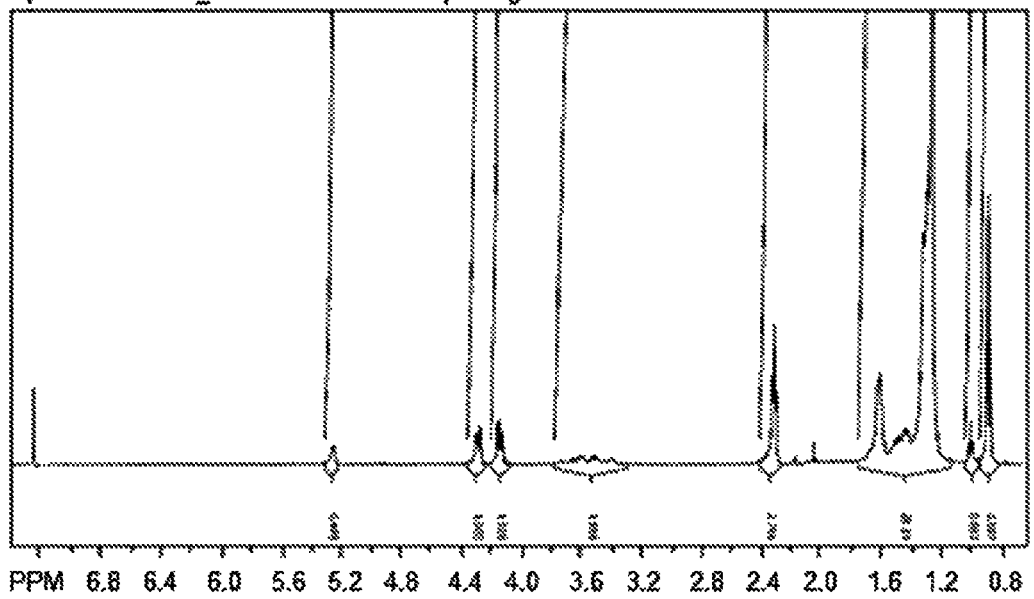
FIG. 21 depicts a $^1$H-NMR of Fraction 10.
Figure 22:
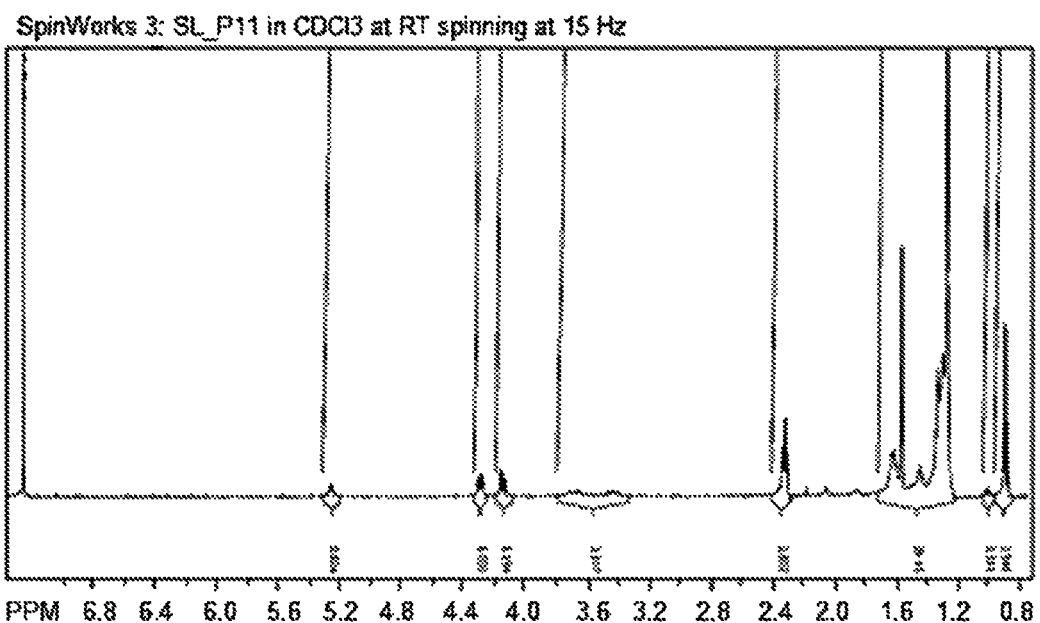
FIG. 22 depicts a $^1$H-NMR of Fraction 11.
Figure 23:
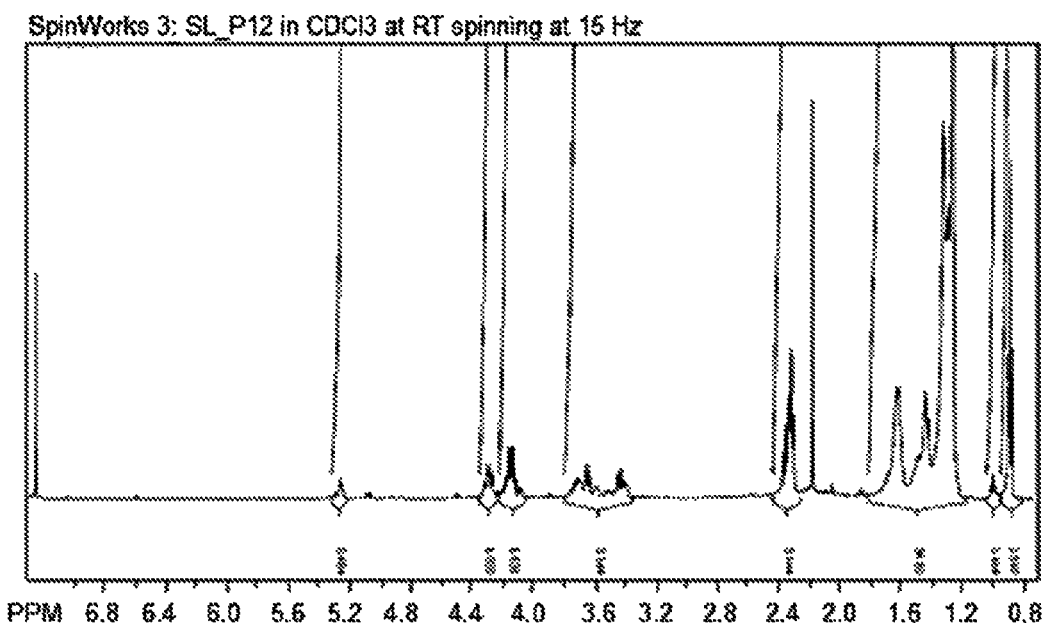
FIG. 23 depicts a $^1$H-NMR of Fraction 12.

A standardized PMTAG Polyol was therefore synthesized using the procedure outlined for PMTAG Polyol 5%. It will be heretofore referred to simply as PMTAG Polyol; however, the various other examples of process and solvent summarized in Table 7 used to produce various classes of PMTAG-derived polyol are by inclusion valued as capable of producing various other useful classes of polyols. As shown in FIG. 11, for the standardized PMTAG Polyol, the chemical shifts at 2.8-2.4 ppm related to the epoxy ring disappeared from the $^1$H-NMR of the PMTAG Polyol, and the chemical shifts at 3.8-3.4 ppm related to proton neighbored by —OH appeared, indicating that the hydroxylation of epoxy ring was complete.

Analytical Methods for PMTAG Polyol

The PMTAG Polyol was analyzed using different techniques. These techniques can be broken down into: (i) chemistry characterization techniques, including OH value, acid value, nuclear magnetic resonance (NMR), electrospray ionization mass spectrometry (ESI-MS), and high pressure liquid chromatography (HPLC); and (ii) physical characterization methods, including thermogravimetric analysis (TGA), differential scanning calorimetry (DSC), and rheology.

Chemistry Characterization Techniques for PMTAG Polyol

OH and acid values of the PMTAG Polyol was determined according to ASTM D1957-86 and ASTM D4662-03, respectively.

$^1$H-NMR spectra were recorded in CDCl$_3$ on a Varian Unity-INOVA at 499.695 MHz. $^1$H chemical shifts are internally referenced to CDCl$_3$ (7.26 ppm). All spectra were obtained using an 8.6 µs pulse with 4 transients collected in 16 202 points. Datasets were zero-filled to 64 000 points, and a line broadening of 0.4 Hz was applied prior to Fourier transforming the sets. The spectra were processed using ACD Labs NMR Processor, version 12.01.

ESI-MS, analysis was performed using a QStar XL quadrupole time-of-flight mass spectrometer (AB Sciex, Concord, ON) equipped with an ionspray source and modified hot source-induced desolvation (HSID) interface (Ionics, Bolton, ON). The ion source and interface conditions were adjusted as follows: ionspray voltage (IS)=4500 V, nebulising gas (GS1)=45, curtain gas (GS2)=45, declustering potential (DP)=60 V and HSID temperature (T)=200° C. Multiply-charged ion signals were reconstructed using the BioTools 1.1.5 software package (AB Sciex, Concord, ON).

HPLC analysis was performed on a Waters Alliance (Milford, Mass.) e2695 HPLC system fitted with a Waters ELSD 2424 evaporative light scattering detector. The HPLC system was equipped with an inline degasser, a pump, and an autosampler. The ELSD nitrogen flow was set at 25 psi with nebulization and drifting tube maintained at 12° C. and 55° C., respectively. Gain was set at 500. All solvents were HPLC grade and obtained from VWR International, Mississauga, ON. The analysis was performed on a Betasil Diol column (250 mm×4.0 mm, 5.0 µm). The temperature of the column was maintained at 50° C. The mobile phase was started with Heptane:Ethyl acetate (90:10)v run for 1 min at a flow rate of 1 mL/min and in a Gradient mode, then was changed to Heptane:Ethyl acetate (67:33) in 55 min and then the ratio of Ethyl acetate was increased to 100% in 20 min and held for 10 min. 5 mg/ml (w/v) solution of crude sample in chloroform was filtered through single step filter vial, and 4 µL of sample was passed through the diol column by normal phase in Gradient mode. Waters Empower Version 2 software was used for data collection and data analysis. Purity of eluted samples was determined using the relative peak area.

Physical Characterization Techniques for PMTAG Polyol

TGA was carried out on a TGA Q500 (TA Instruments, DE, USA) equipped with a TGA heat exchanger (P/N 953160.901). Approximately 8.0-15.0 mg of sample was loaded in the open TGA platinum pan. The sample was heated from 25 to 600° C. under dry nitrogen at a constant rate of 10° C./min.

DSC measurements of the PMTAG Polyol were run on a Q200 model (TA Instruments, New Castle, Del.) under a nitrogen flow of 50 mL/min. PMTAG Polyol samples between 3.5 and 6.5 (±0.1) mg were run in standard mode in hermetically sealed aluminum DSC pans. The sample was equilibrated at 90° C. for 10 min to erase thermal memory, and then cooled at 5.0° C./min to −90° C. where it was held isothermally for 5 min, and subsequently reheated at a constant rate of 5.0° C./min to 90° C. The "TA Universal Analysis" software was used to analyze the DSC thermograms and extract the peak characteristics. Characteristics of non-resolved peaks were obtained using the first and second derivatives of the differential heat flow.

A temperature-controlled Rheometer (AR2000ex, TA Instruments, DE, USA) was used to measure the viscosity and flow property of the PMTAG Polyol using a 40 mm 2° steel geometry. Temperature control was achieved by a Peltier attachment with an accuracy of 0.1° C. Shear Stress was measured at each temperature by varying the shear rate from 1 to 1200 s$^{-1}$. Measurements were taken at 10° C. intervals from high temperature (100° C.) to 10° C. below the DSC onset of crystallization temperature of each sample. Viscosities of samples were measured from each sample's melting point up to 110° C. at constant temperature rate (1.0 and 3.0° C./min) with constant shear rate (200 s$^{-1}$). Data points were collected at intervals of 1° C. The viscosity obtained in this manner was in very good agreement with the measured viscosity using the shear rate/share stress. The shear rate range was optimized for torque (lowest possible is 10 μNm) and velocity (maximum suggested of 40 rad/s).

Compositional Analysis of PMTAG Polyol

To establish the composition of the PMTAG Polyol, the crude polyol was separated into molecularly similar fractions by flash chromatography using a mixture of ethyl acetate and hexane as eluent. Twelve (12) fractions were collected. The fractions were characterized by HPLC, $^1$H-NMR and MS. The NMR spectra of Fractions 1 to 12 are shown in FIG. 12 to FIG. 23 and related $^1$H-NMR chemical shifts, δ, in CDCl$_3$ are listed in Table 8.

HPLC retention times and MS data related to the various fractions are listed in Table 9. The results of the analyses are summarized in Table 9. Related structures are shown in Scheme 5. The polyol molecules are bounded to water so that the molecular weights determined by MS did not exactly match the structures suggested, but were deduced from the mass fraction values, taking this into consideration. These structures are all supported by $^1$H-NMR.

TABLE 8

$^1$H-NMR chemical shifts, δ, of PMTAG Polyol fractions

| Fraction | $^1$H-NMR Chemical shifts, δ, in CDCl$_3$ (ppm) |
|---|---|
| 1 | 5.2 (1, m), 4.4-4.2 (2, dd)), 4.2-40 (2, dd), 2.4-2.2 (6, t), 1.6-1.5 (6, m), 1.2 (69, m), 0.8 (9, t) |
| 2 | 4.4-4.0 (5, m), 2.4-2.2 (4, m), 1.6 (4, m), 1.2 (40, m), 0.8 (6, t) |
| 3 | 5.6 (0.7, m), 5.2 (0.6, m), 5.0 (0.6, m), 4.4-4.0 (3, m), 3.8 (1, t), 2.4-2.2 (4, m), 2.2-2.0 (1, m), 1.8-1.2 (42, m), 0.8 (6, t) |
| 4 | 5.2 (0.1, m), 4.4-4.0 (2.4, m), 3.6 (1, t), 2.4-2.2 (3, t), 1.8-1.2 (48, m), 0.8 (6, t). |

TABLE 8-continued $^1$H-NMR chemical shifts, δ, of PMTAG Polyol fractions

| Fraction | $^1$H-NMR Chemical shifts, δ, in CDCl$_3$ (ppm) |
|---|---|
| 5 | 5.2 (1, m), 4.4-4.2 (2, dd), 4.2-4.0 (2, dd), 3.4 (2, m), 2.4-2.2 (6, m), 1.6-1.2 (78, m), 0.8 (9, t) |
| 6 | 5.2 (1, m), 4.4-4.2 (2, dd), 4.2-4.0 (2, dd), 3.6 (1.5, br), 3.4 (1, m), 2.4-2.2 (6, m), 1.6-1.2 (77, m), 0.8 (9, t) |
| 7 | 5.2 (1, m), 4.4-4.2 (2, dd), 4.2-4.0 (2, dd), 3.4 (2, m), 2.4-2.2 (6, m), 1.6-1.2 (64, m), 1.0 (3, t), 0.8 (6, t) |
| 8 | 5.2 (1, m), 4.4-4.2 (2, dd), 4.2-4.0 (2, dd), 3.6 (1, m), 3.5 (1, m), 2.4-2.2 (6, m), 1.6-1.2 (66, m), 1.0 (2.6, t), 0.8 (6, t) |
| 9 | : 5.2 (1, m), 4.4-4.2 (2, dd), 4.2-4.0 (2, dd), 3.6 (1, m), 3.5 (1, m), 2.4-2.2 (6, m), 1.6-1.2 (64, m), 1.0 (2.7, t), 0.8 (6, t) |
| 10 | 5.2 (1, m), 4.4-4.2 (2, dd), 4.2-4.0 (2, dd), 3.6-3.2 (3.3, m), 2.4-2.2 (5.8, m), 1.6-1.2 (58, m), 1.0 (1.3, t), 0.8 (5.2, t) |
| 11 | 5.2 (1, m), 4.4-4.2 (2, dd), 4.2-4.0 (2, dd), 3.6-3.2 (6.2, m), 2.4-2.2 (5.6, m), 1.6-1.2 (58, m), 1.0 (1.0, t), 0.8 (5.1, t) |

$^1$H-NMR spectra of Fractions 1 and 5-11 confirmed that these fractions contained molecules with a TAG glycerol backbone structure; Fractions 2-4 contained molecules with a hydrolyzed TAG structure (no glycerol backbone), indicating that these fractions contained hydrolyzed by-product formed during the hydroxylation reaction. Additionally, unreacted terminal double bonds were detected in Fraction 4. No double bonds or OH related chemical shifts (at 3.6-3.2 ppm) were detected in the $^1$H-NMR of Fraction 1, suggesting that this fraction only contained saturated TAGs.

The OH related chemical shift (at 3.6-3.2 ppm) appeared in Fractions 5,-11, indicating that the molecules in these fractions contained both hydroxyl groups as well as the glycerol backbone structure of TAGs. The PMTAG Polyol structure is discussed in detail further below. In the $^1$H-NMR of PMTAG Polyol (FIG. 11), the protons of the glycerol skeleton, —CH$_2$CH(O)CH$_2$— and —OCH$_2$CHCH$_2$O— are present at δ 5.3-5.2 ppm and 4.4-4.1 ppm, respectively; —C(=O)CH$_2$— at δ 2.33-2.28 ppm; —C(=O)CH$_2$CH$_2$— at δ 1.60 ppm; and proton neighbored by —OH appeared at 3.8-3.4 ppm. There are two types of —CH$_3$, one with n=2 present at δ=1.0-0.9 ppm and another with n=8 at 0.9-0.8 ppm.

The terminal structure of the fractions was easily identified based on the chemical shifts related to —CH$_3$. The chemical shift at 1.0-0.9 ppm was not presented in Fractions 5 and 6, and only one chemical shift appeared at δ 3.8-3.4 ppm, indicating that Fraction 5 and 6 do not have terminal butyl structures with (n=2, Scheme 5). This chemical shift was displayed in Fractions 7-11 indicating terminal structures with n=2. As well, based on the chemical shifts at 3.8 to 3.4 ppm related to protons neighbored by OH groups, terminal OH groups can be identified. Terminal OH groups were detected in Fractions 10 and 11 but not in Fractions 5-9.

TABLE 9

Characterization of PMTAG Polyol fractions

| Fraction | HPLC Retention Time (min) | Content (%) | MS and possible formula | Structure suggested based on $^1$H-NMR and MS (Scheme 6) |
|---|---|---|---|---|
| 1 | 2.801 | 42.17 | 947.8(C$_{61}$H$_{118}$O$_6$) 849.8 (C$_{54}$H$_{104}$O$_6$) | Saturated TAGs |
| 2 | 7.196 | 0.67 | 667.5 (C$_{42}$H$_{82}$O$_5$) | Not a TAG structure; Contains hydrolyzed by-products |
| 3 | 9.827 | 0.18 | — | Mixture of fraction 1, fraction 2, and unreacted terminal double bond structures |

TABLE 9-continued

Characterization of PMTAG Polyol fractions

| Fraction | HPLC Retention Time (min) | Content (%) | MS and possible formula | Structure suggested based on $^1$H-NMR and MS (Scheme 6) |
|---|---|---|---|---|
| 4 | 10.531 | 0.08 | 825.29 ($C_{50}H_{96}O_8$) | Not a TAG structure; Contain hydrolyzed by-products with oleic acid derived diols |
| 5 | 15.660 | 5.07 | 884.6 ($C_{53}H_{102}O_8 \cdot H_2O$) | TAG-like diols containing one |
| 6 | 16.577 | 1.66 | 889.5 ($C_{52}H_{100}O_8 \cdot 2H_2O$) | oleic acid-like derived diol |
| 7 | 19.415 | 0.94 | 889.7($C_{55}H_{106}O_8$) 805.2 ($C_{48}H_{92}O_8 \cdot H_2O$) 833.4 ($C_{48}H_{92}O_8 \cdot 2H_2O$) | TAG-like diols containing one oleic acid-like derived or/and one 9-dodecenoic acid-like derived diol |
| 8 | 20.854 | 14.04 | 872.8 ($C_{51}H_{98}O_{10}$) 833.4($C_{47}H_{90}O_{10} \cdot H_2O$, $C_{45}H_{86}O_{10} \cdot 2H_2O$, $C_{48}H_{92}O_8 \cdot 2H_2O$) 805.4 ($C_{45}H_{86}O_{10} \cdot H_2O$, $C_{48}H_{92}O_8 \cdot H_2O$) | TAG-like diols containing one 9-dodecenoic acid-like derived diol; TAG-like tetrols containing one or two oleic acid-like derived diols or/and one 9-dodecenoic acid-like derived diol |
| 9 | 20.601 21.945 | 0.95 | 805.4 ($C_{45}H_{86}O_{10} \cdot H_2O$) 817.8 ($C_{47}H_{90}O_{10}$) 844.8 ($C_{49}H_{94}O_{10}$) | |
| 10 | 22.296 | 0.95 | 719.5 ($C_{39}H_{74}O_{10} \cdot H_2O$) 805.6 ($C_{45}H_{86}O_{10} \cdot H_2O$) 847.6 ($C_{48}H_{92}O_{10} \cdot H_2O$) | TAGs-like diols containing one 9-decenoic acid-like derived diol; TAGs-like tetrols containing one or two oleic acid-like, one or two 9-dodenonic acid-like or/and one 9-decenoic acid-like derived diols |
| 11 | 30.751, 31.374 | 25.58% + 3.05% | 777.3 ($C_{42}H_{80}O_{12}$) 805.3 ($C_{44}H_{84}O_{12}$, $C_{45}H_{86}O_{10} \cdot H_2O$, $C_{48}H_{92}O_8 \cdot H_2O$) 877.7 ($C_{49}H_{94}O_{12}$) 651.4 ($C_{33}H_{62}O_{12}$) | TAG-like hexols containing one or two oleic acid-like and one or two 9-dodecenoic acid-like derived diol; TAG-like tetrols containing one 9-decenoic acid-like derivatives and one oleic acid-like or 9-dodecenoic acid-like derived diol; TAG-like diols containing one 9-decenoic acid-like derived diol. |

Scheme 6. Structure suggested based on $^1$H—NMR and MS a) Oleic acid-like derived diol:

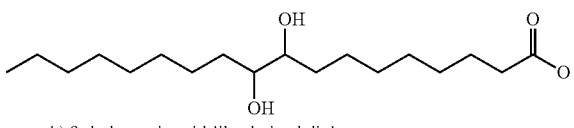

b) 9-dodecenoic acid-like derived diol:

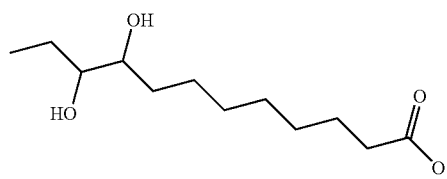

c) 9-decenoic acid-like derived diol:

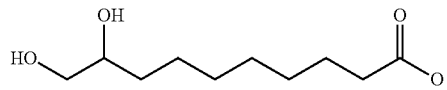

HPLC of PMTAG Polyol Results

Figure 24:
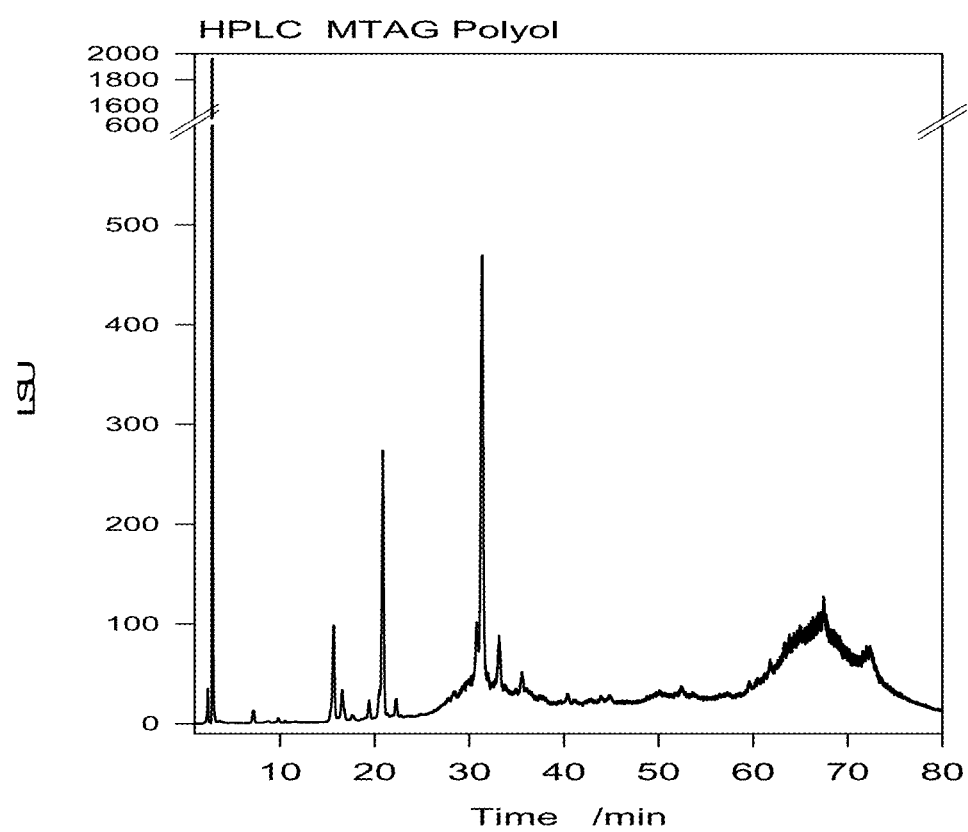
FIG. 24 depicts a HPLC of PMTAG Polyol.

The HPLC curve of the PMTAG Polyol is shown in FIG. 24. The analysis of the HPLC of PMTAG Polyol was carried out with the help of fractions separated using flash chromatography (described above) used as standards. The saturated TAG composition appeared at 2.80 min; the hydrolyzed by-products at 7 to 12 min; PMTAG diols with long fatty acid chain at 15 to 19 min; PMTAG diols with short fatty acid chain, or PMTAG tetrols with long fatty acid chain at 19 to 21 min; PMTAG tetrols with short fatty acid and PMTAG diols with terminal OH group at 21 to 23 min; PMTAG tetrols with terminal OH group and PMTAG hexols appeared at 30 min and up.

Structures of PMTAG Polyol

The theoretical structures of PMTAG Polyol based on the TAG analysis of palm oil are given below in Scheme 7. These structures can be directly related to the structures of PMTAG determined by GC and $^1$H-NMR.

Scheme 7. Possible structures in PMTAG Polyol

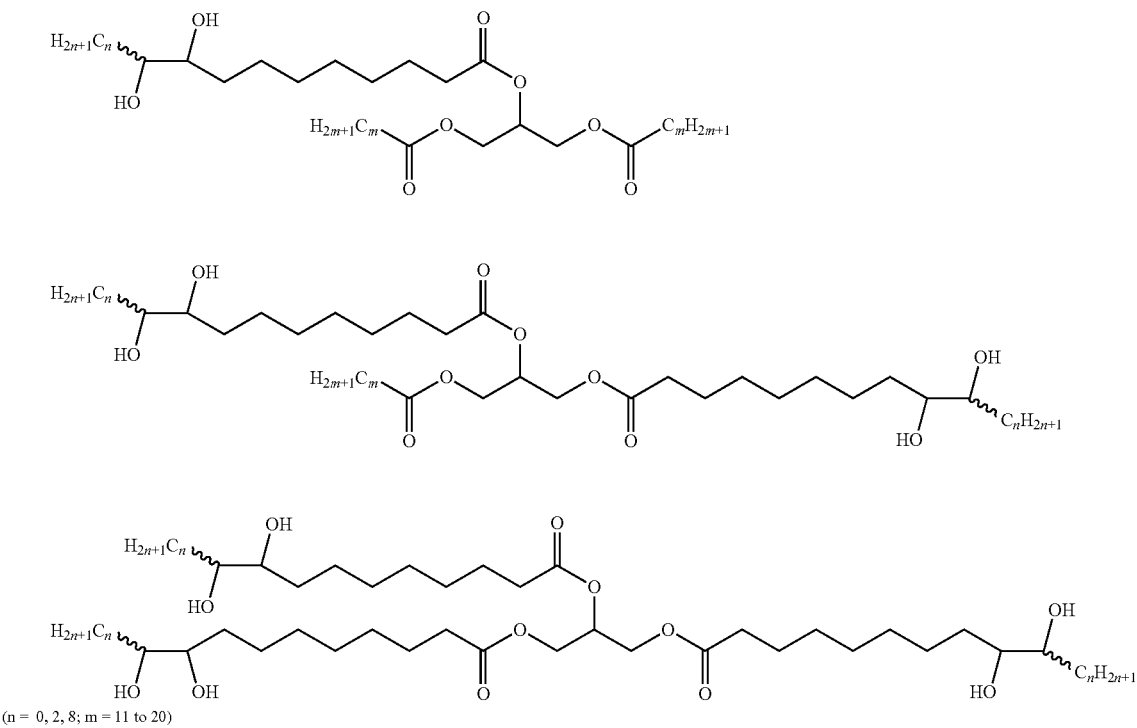

(n = 0, 2, 8; m = 11 to 20)

The structures of PMTAG Polyol suggested by MS and $^1$H-NMR of its fractions are presented in Scheme 8.

Scheme 8. Structures of PMTAG Polyol suggested by MS and $^1$H—NMR

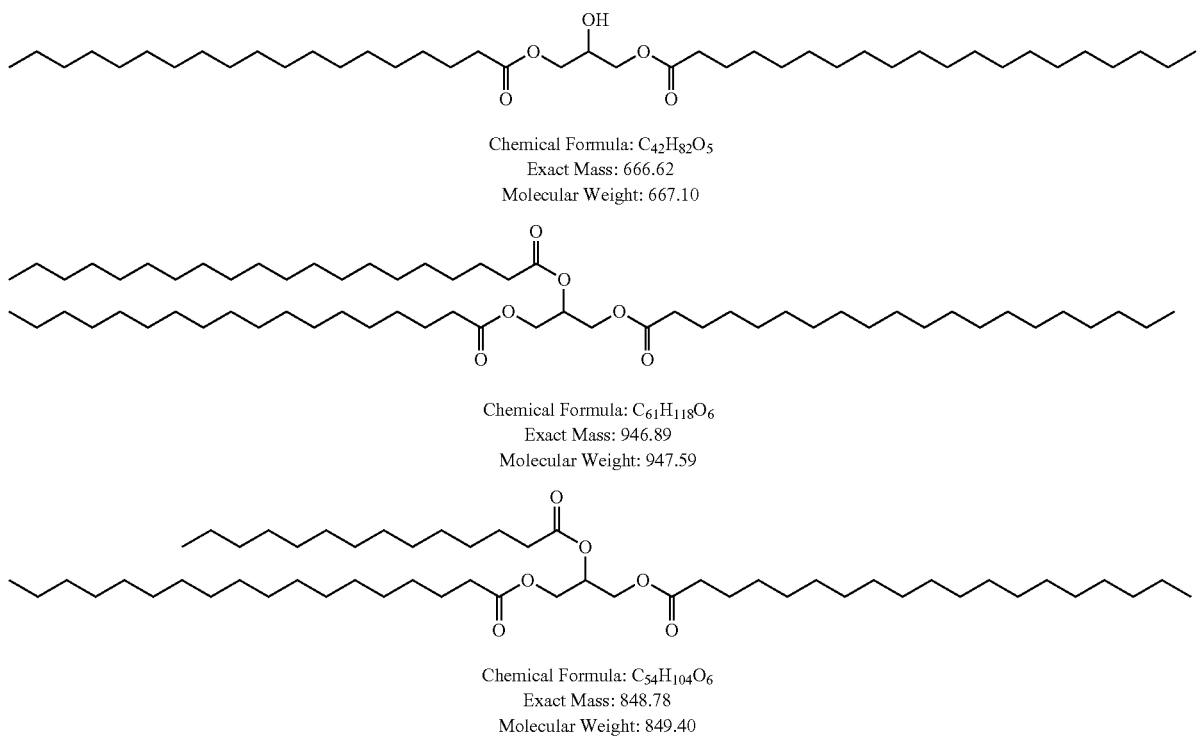

Chemical Formula: $C_{42}H_{82}O_5$
Exact Mass: 666.62
Molecular Weight: 667.10

Chemical Formula: $C_{61}H_{118}O_6$
Exact Mass: 946.89
Molecular Weight: 947.59

Chemical Formula: $C_{54}H_{104}O_6$
Exact Mass: 848.78
Molecular Weight: 849.40

-continued
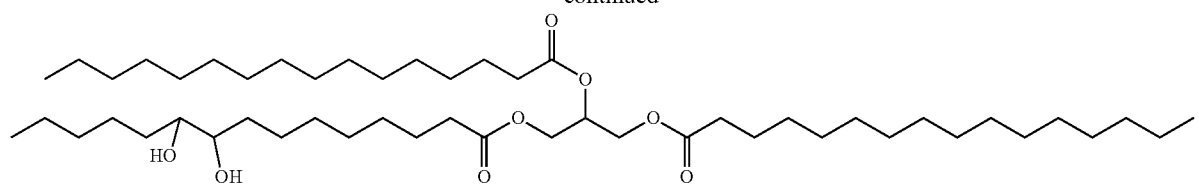
Chemical Formula: $C_{50}H_{96}O_8$
Exact Mass: 824.71
Molecular Weight: 825.29
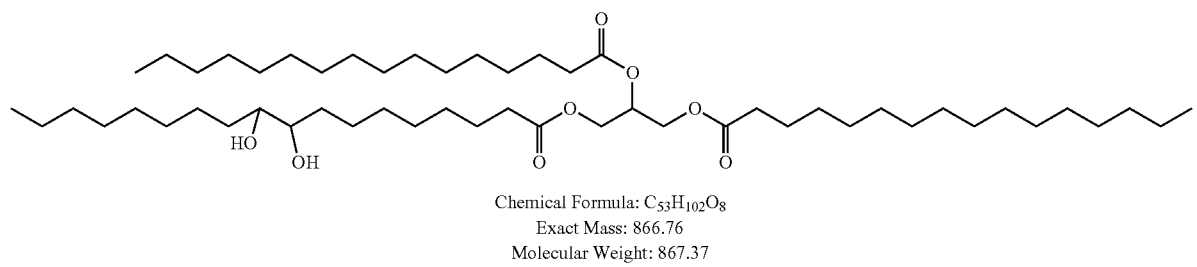
Chemical Formula: $C_{53}H_{102}O_8$
Exact Mass: 866.76
Molecular Weight: 867.37
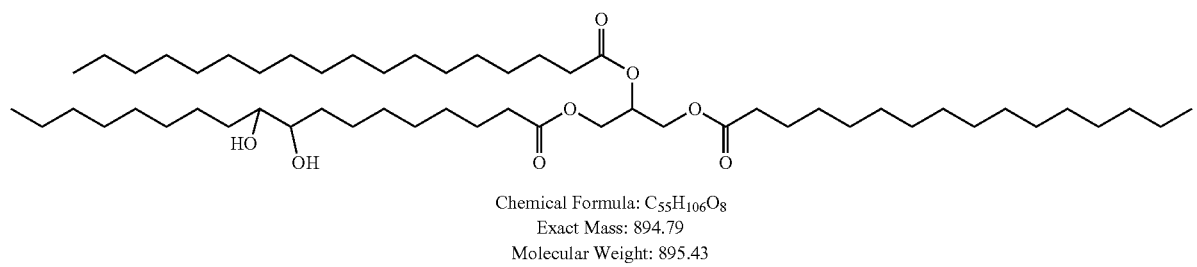
Chemical Formula: $C_{55}H_{106}O_8$
Exact Mass: 894.79
Molecular Weight: 895.43
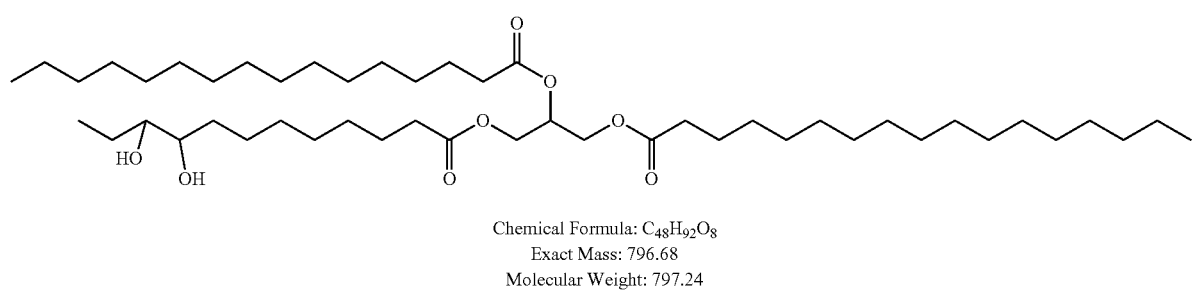
Chemical Formula: $C_{48}H_{92}O_8$
Exact Mass: 796.68
Molecular Weight: 797.24
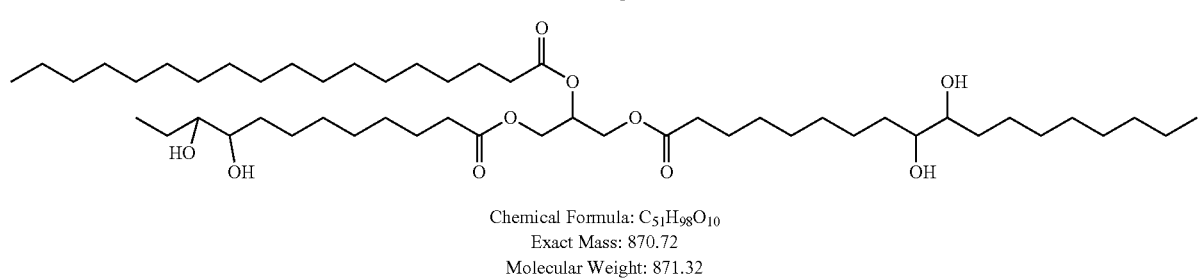
Chemical Formula: $C_{51}H_{98}O_{10}$
Exact Mass: 870.72
Molecular Weight: 871.32
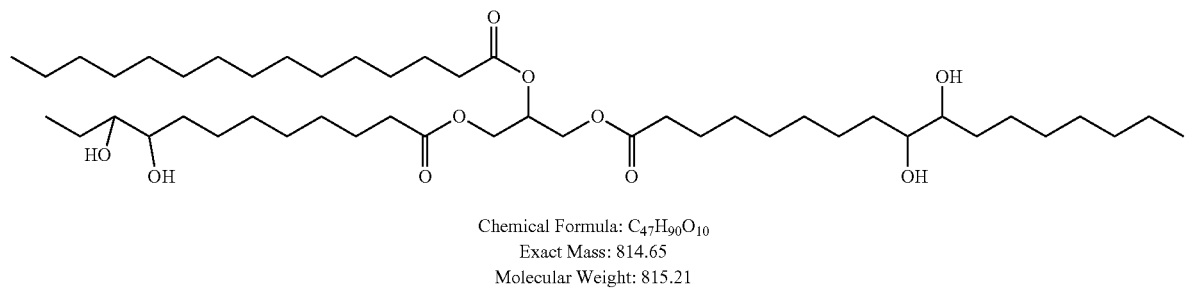
Chemical Formula: $C_{47}H_{90}O_{10}$
Exact Mass: 814.65
Molecular Weight: 815.21

-continued
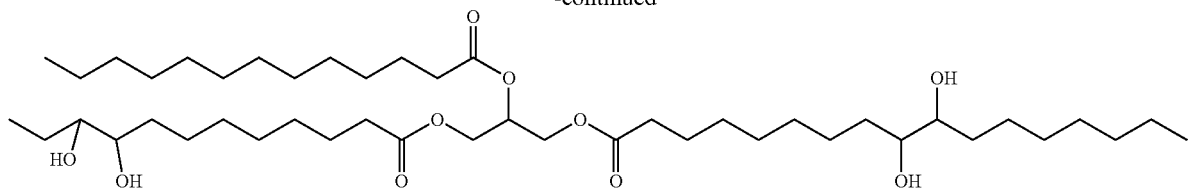
Chemical Formula: $C_{45}H_{86}O_{10}$
Exact Mass: 786.62
Molecular Weight: 787.16
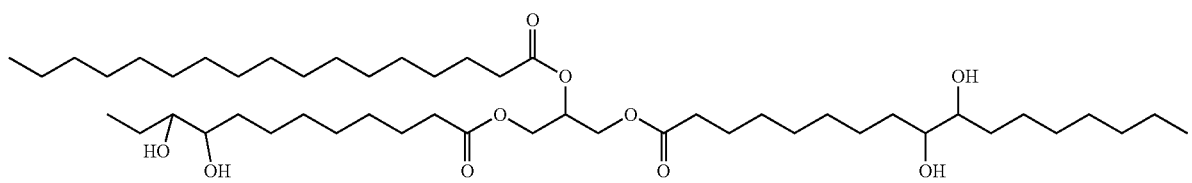
Chemical Formula: $C_{49}H_{94}O_{10}$
Exact Mass: 842.68
Molecular Weight: 843.26
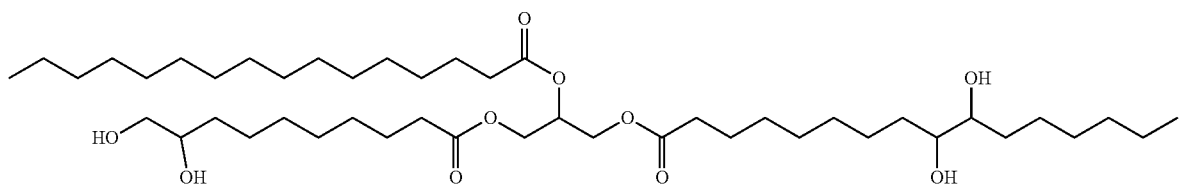
Chemical Formula: $C_{45}H_{86}O_{10}$
Exact Mass: 786.62
Molecular Weight: 787.16
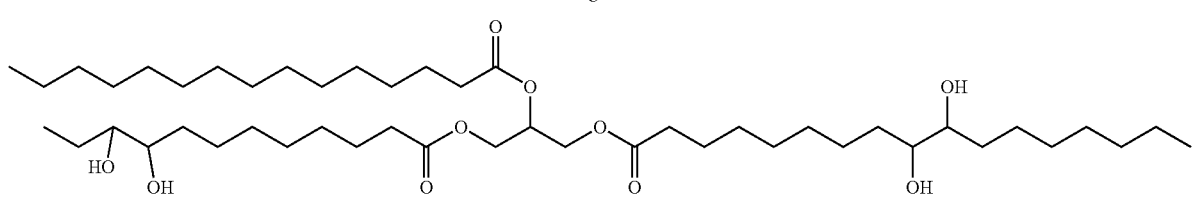
Chemical Formula: $C_{47}H_{90}O_{10}$
Exact Mass: 814.65
Molecular Weight: 815.21
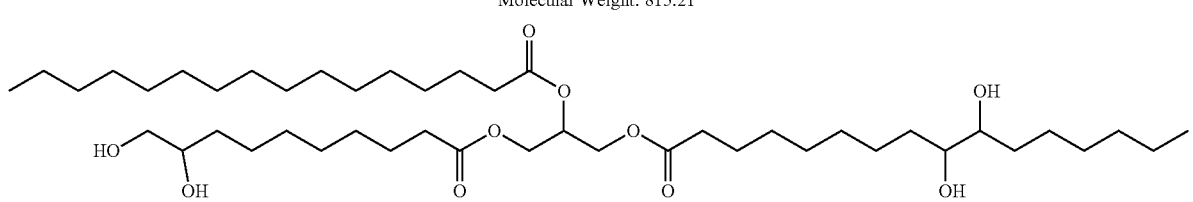
Chemical Formula: $C_{45}H_{86}O_{10}$
Exact Mass: 786.62
Molecular Weight: 787.16
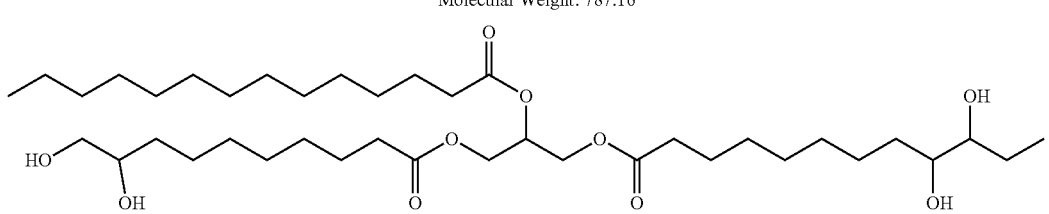
Chemical Formula: $C_{39}H_{74}O_{10}$
Exact Mass: 702.53
Molecular Weight: 703.00

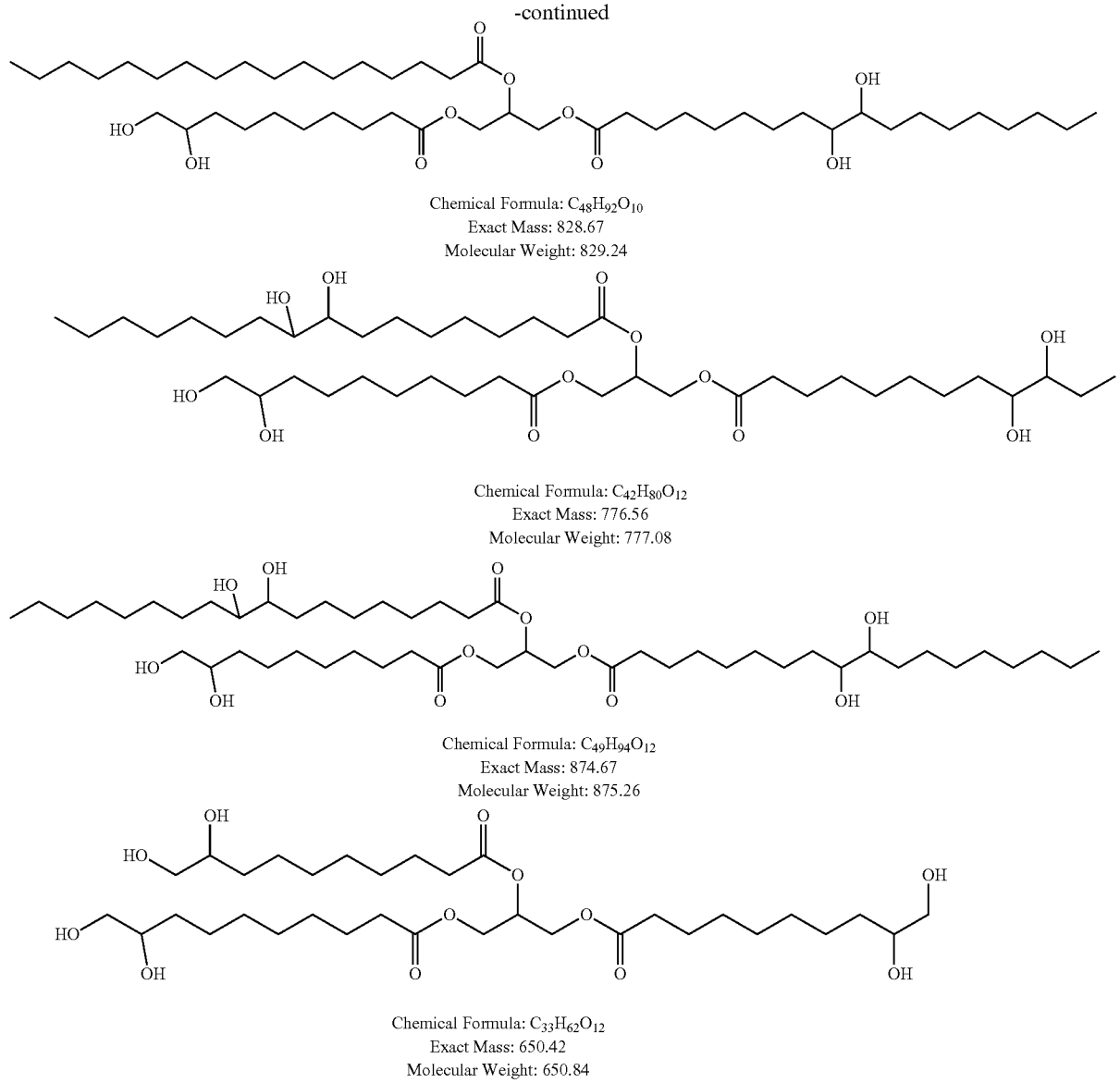

Chemical Formula: C₄₈H₉₂O₁₀
Exact Mass: 828.67
Molecular Weight: 829.24

Chemical Formula: C₄₂H₈₀O₁₂
Exact Mass: 776.56
Molecular Weight: 777.08

Chemical Formula: C₄₉H₉₄O₁₂
Exact Mass: 874.67
Molecular Weight: 875.26

Chemical Formula: C₃₃H₆₂O₁₂
Exact Mass: 650.42
Molecular Weight: 650.84

Physical Properties of PMTAG Polyol
Thermogravimetric Analysis of PMTAG Polyol

Figure 25A:
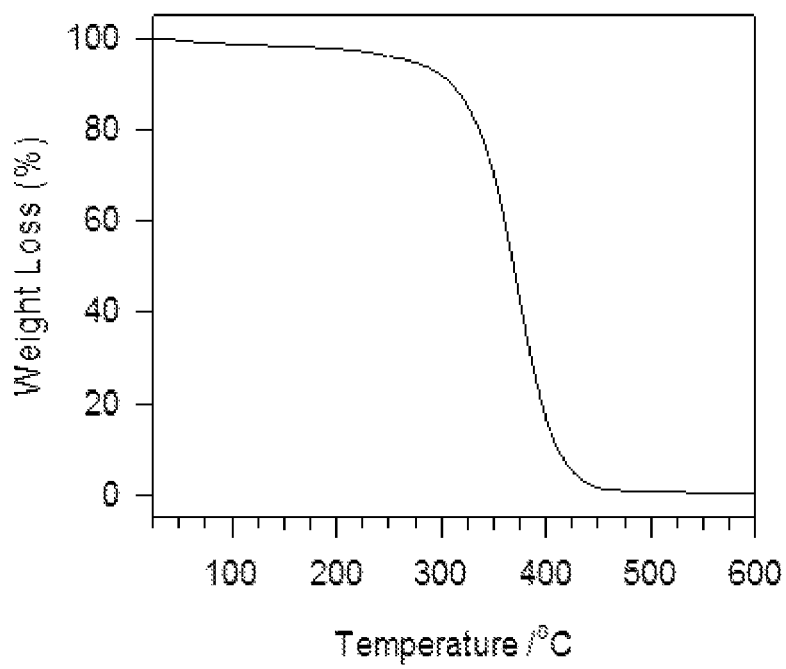
FIG. 25a depicts a TGA of PMTAG Polyol.
Figure 25B:
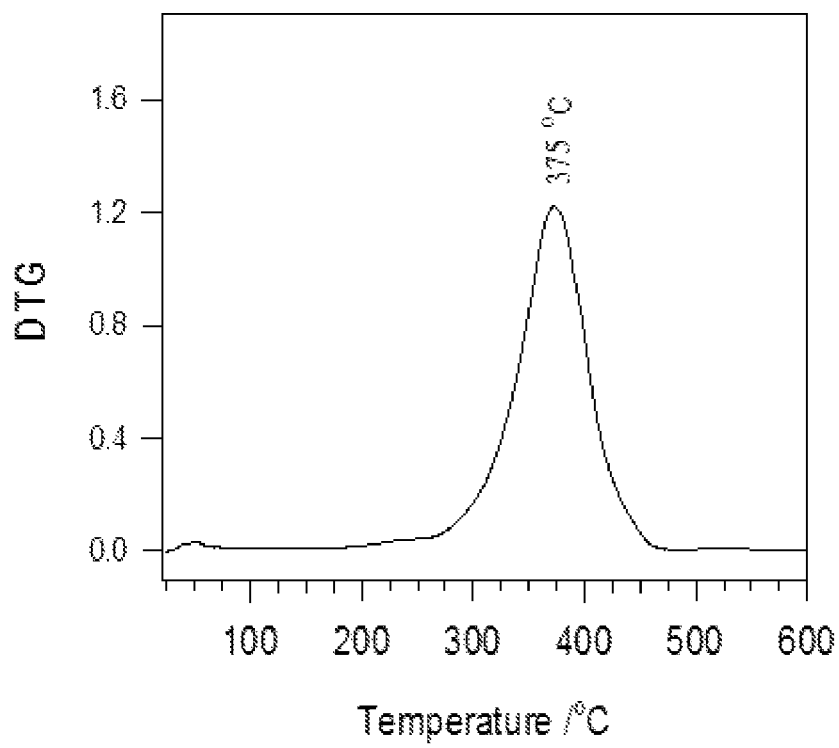
FIG. 25b depicts a DTG profile of PMTAG polyol.

The TGA and corresponding DTG profiles of the PMTAG Polyol are shown in FIGS. 25a and 25b, respectively. The onset temperature of degradation of PMTAG measured at 5% and 10% decomposition and the DTG peak temperatures are provided in Table 10.

TGA revealed a decomposition spanning from ~260° C. to 470° C. As can be seen from the TGA and DTG curves, the PMTAG Polyol degradation profile was dominated by one main step, represented by a DTG peak at 390° C., due to the breakage of the ester bonds.

TABLE 10

Onset temperature of degradation as determined at 5% ($T_{5\%}$) and 10% ($T_{10\%}$), and peak DTG temperature ($T_{d1}$) of PMTAG Polyol

| PMTAG Polyol | $T_{5\%}$ | $T_{10\%}$ | $T_{d1}$ |
|---|---|---|---|
| Temperature (° C.) | 309 | 330 | 390 |

Thermal Behavior of PMTAG Polyol

Figure 26A:
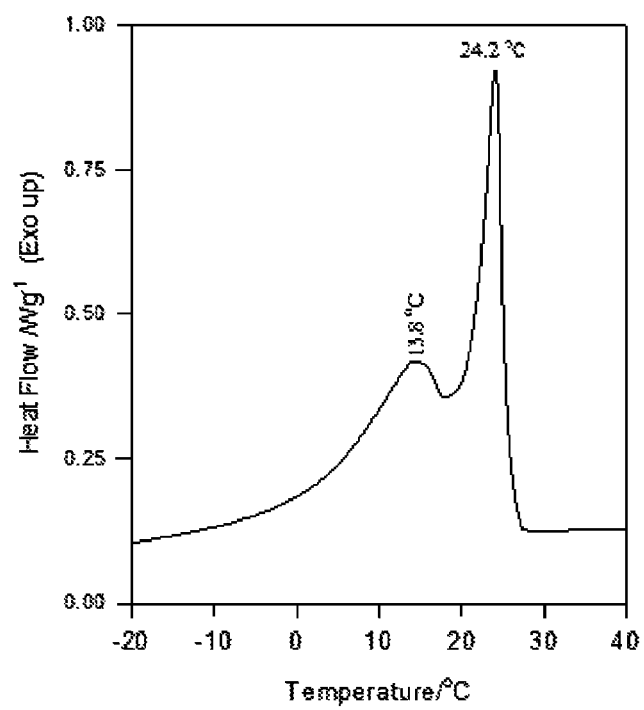
FIG. 26a depicts a crystallization profile of PMTAG polyol.
Figure 26B:
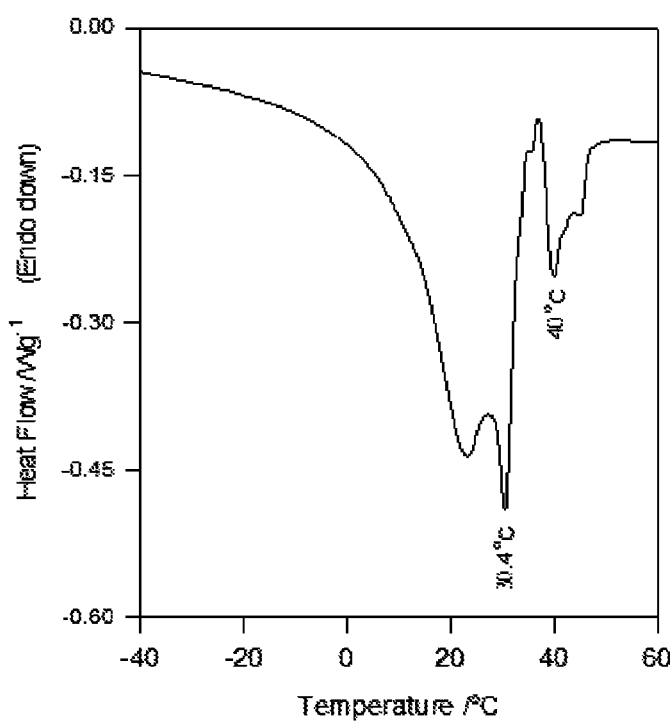
FIG. 26b depicts a heating profile of PMTAG polyol.

The crystallization and heating profiles (both at 5° C./min) of PMTAG Polyol are shown in FIGS. 26a and 26b, respectively. Two main exotherms, which can be related to a high and low melting fraction in the polyols were observed for the PMTAG Polyol. Similar to the PMTAG itself, the low temperature exothermic event centered at ~14° C. is associated with an "olein" fraction of the polyols, and the high temperature exotherm to a "stearin" fraction of the polyols. The heating thermograms of the polyols displayed several endothermic events but no exotherms, indicating that polymorphic transformation mediated by melt does not occur with the polyols. PMTAG Polyol presented an enthalpy of melting ($\Delta H_M$) of 96.2 J/g and an enthalpy of crystallization ($\Delta H_C$) of 94.1 J/g.

Flow Behavior and Viscosity of PMTAG Polyol

Figure 27:
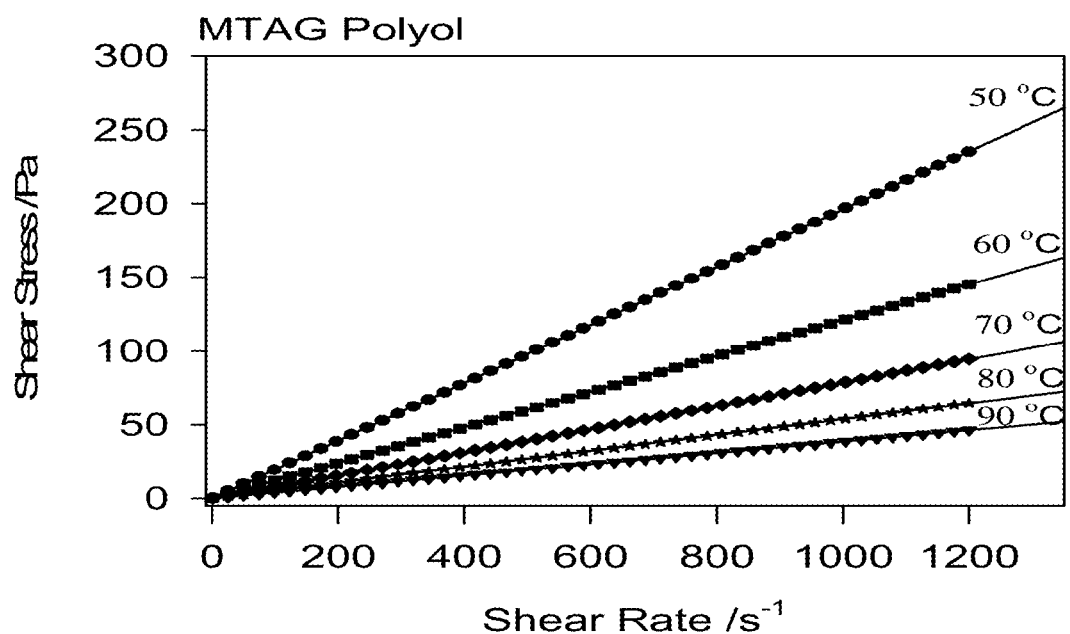
FIG. 27 depicts a shear rate-shear stress in the in the liquid state of PMTAG polyol.
Figure 28:
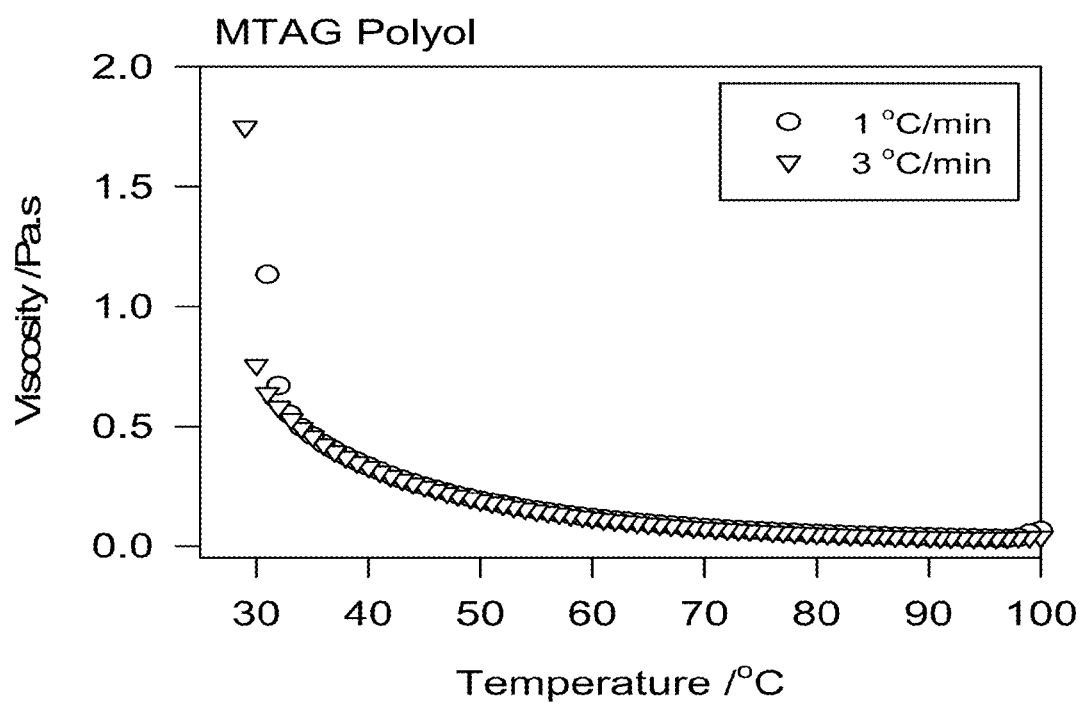
FIG. 28 depicts a viscosity versus temperature curve obtained during cooling of PMTAG polyol at 3° C./min and 1° C./min.

FIG. 27 shows shear rate-shear stress curves of the PMTAG Polyol obtained at different temperatures. FIG. 28 shows the viscosity versus temperature curves obtained during cooling at 3° C./min and 1° C./min. The power index values (n) were all approximately equal to 1, indicating a Newtonian behavior. Fits to the Herschel-Bulkley (eq. 1) model are included in FIG. 27. The data collected at 40° C. and below indicated that the sample has started crystallizing at this temperature. The flow behavior observed for PMTAG Polyol is very similar to that of PMTAG.

Note that the shear rate-shear stress data collected at 100° C. and above cannot be discussed because the viscosity of the PMTAG polyol was too low to be measured by the geometry used in these experiments.

The viscosity versus temperature of liquid PMTAG polyols obtained using the ramp procedure presented the exponential behavior of liquid hydrocarbons.

Comparison of Viscosity of PMTAG and PMTAG Polyol

Figure 29:
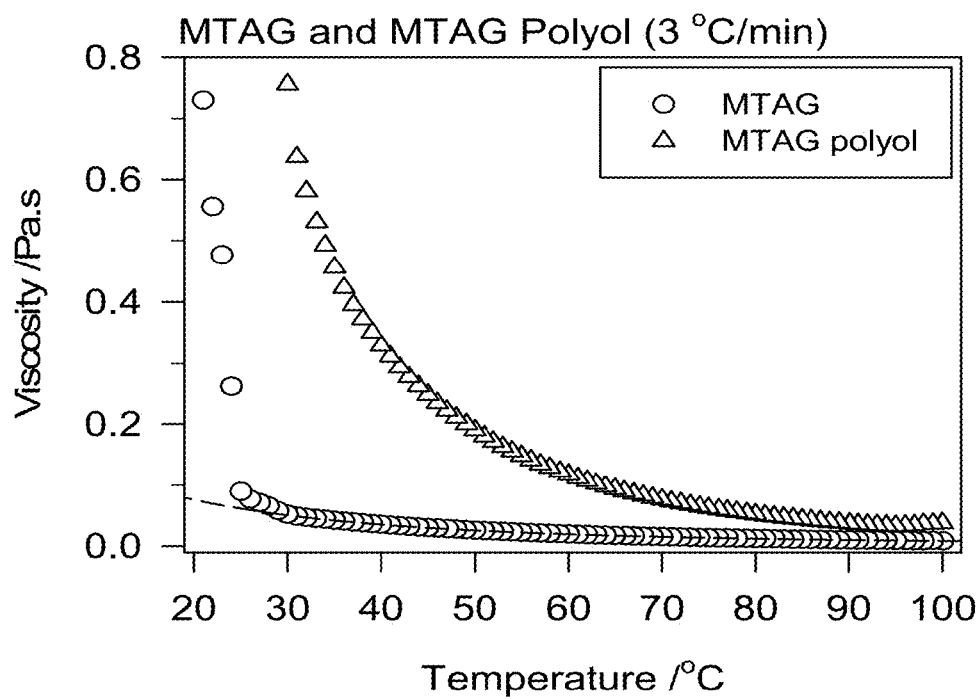
FIG. 29 depicts a comparison between the viscosity of PMTAG and PMTAG polyol.

Viscosity versus temperature graphs of PMTAG and PMTAG Polyol using 3° C./min are shown in FIG. 29. PMTAG Polyol displayed higher viscosity than PMTAG due to presence of the OH groups.

C. Polyurethane Foams from PMTAG Polyols

Polyurethane Foam Polymerization

Polyurethanes are one of the most versatile polymeric materials with regards to both processing methods and mechanical properties. The proper selection of reactants enables a wide range of polyurethanes (PU) elastomers, sheets, foams etc. Polyurethane foams are cross linked structures that may be prepared based on a polymerization addition reaction between organic isocyanates and polyols, as shown in Scheme 9 below. Such a reaction may also be commonly referred to as a gelation reaction.

Scheme 9. General formation of urethane linkage between isocyanate group and OH group.

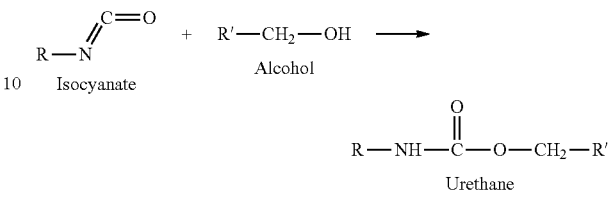

A polyurethane is a polymer composed of a chain of organic units joined by the carbamate or urethane link. Polyurethane polymers may be formed by reacting one or more monomers having at least two isocyanate functional groups with at least one other monomer having at least two isocyanate-reactive groups, i.e., functional groups which are reactive towards the isocyanate function. The isocyanate ("NCO") functional group is highly reactive and is able to react with many other chemical functional groups. In order for a functional group to be reactive to an isocyanate functional group, the group may have at least one hydrogen atom which is reactive to an isocyanate functional group. A polymerization reaction is presented in Scheme 10, using a hexol structure as an example.

Scheme 10. Preparation of cross linked polyurethane from MDI and PMTAG Polyols. Hexol structure is used as an example.

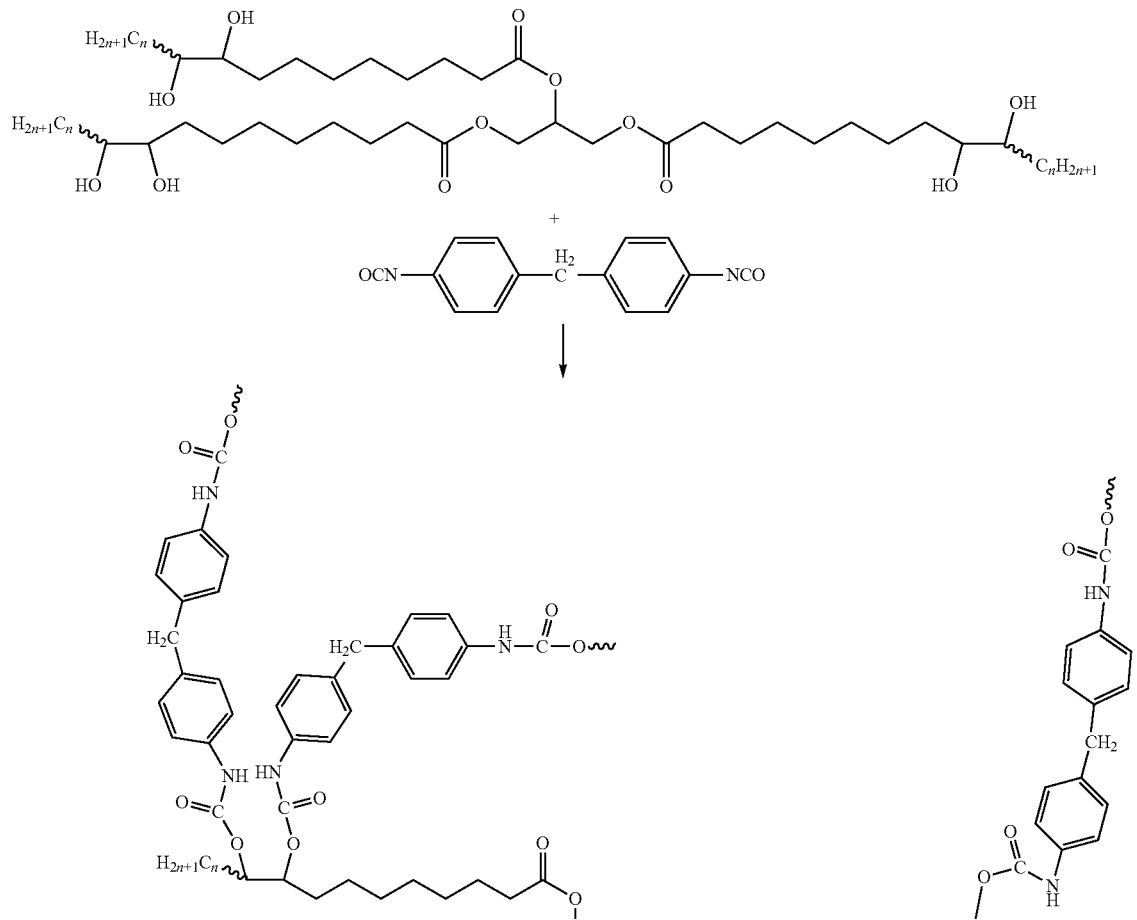

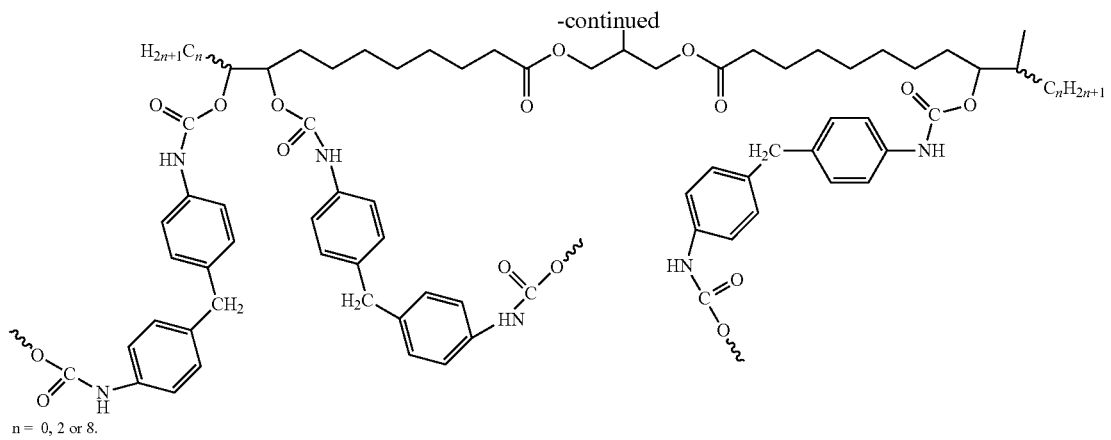

n = 0, 2 or 8.

In addition to organic isocyanates and polyols, foam formulations often include one or more of the following non-limiting components: cross-linking agents, blowing agents, cell stabilizer components, and catalysts. In some embodiments, the polyurethane foam may be a flexible foam or a rigid foam.

Organic Isocyanates

The polyurethane foams are derived from an organic isocyanate compound. In order to form large linear polyurethane chains, di-functional or polyfunctional isocyanates are utilized. Suitable polyisocyanates are commercially available from companies such as, but not limited to, Sigma Aldrich Chemical Company, Bayer Materials Science, BASF Corporation, The Dow Chemical Company, and Huntsman Chemical Company. The polyisocyanates may have a formula $R(NCO)_n$, where n is 1 to 10, and wherein R is 2 and 40 carbon atoms, and wherein R contains at least one aliphatic, cyclic, alicyclic, aromatic, branched, aliphatic- and alicyclic-substituted aromatic, aromatic-substituted aliphatic and alicyclic group. Examples of polyisocyanates include, but are not limited to, diphenylmethane-4,4'-diisocyanate (MDI), which may either be crude or distilled; toluene-2,4-diisocyanate (TDI); toluene-2,6-diisocyanate (TDI); methylene bis(4-cyclohexylisocyanate ($H_{12}$MDI); 3-isocyanatomethyl-3,5,5-trimethyl-cyclohexyl isocyanate (IPDI); 1,6-hexane diisocyanate (HDI); naphthalene-1,5-diisocyanate (NDI); 1,3- and 1,4-phenylenediisocyanate; triphenylmethane-4,4',4"-triisocyanate; polyphenylpolymethylenepolyisocyanate (PMDI); m-xylene diisocyanate (XDI); 1,4-cyclohexyl diisocyanate (CHDI); isophorone diisocyanate; isomers and mixtures or combinations thereof.

Polyols

The polyols used in the foams described herein are metathesized triacylglycerol (MTAG) based polyols derived from natural oils, including palm oil. The synthesis of the PMTAG Polyol was described earlier, and involves epoxidation and subsequent hydroxylation of a PMTAG derived from a natural oil, e.g., palm oil.

Cross-Linking Agents and Chain Extenders

Cross-linking agents or chain extenders may be used if needed in preparation of polyurethane foams. Suitable cross-linking agents include, but are not limited to, low-molecular weight compounds containing at least two moieties selected from hydroxyl groups, primary amino groups, secondary amino groups, and other active hydrogen-containing groups which are reactive with an isocyanate group. Crosslinking agents include, for example, polyhydric alcohols (especially trihydric alcohols, such as glycerol and trimethylolpropane), polyamines, and combinations thereof. Non-limiting examples of polyamine crosslinking agents include diethyltoluenediamine, chlorodiaminobenzene, diethanolamine, diisopropanolamine, triethanolamine, tripropanolamine, 1,6-hexanediamine, and combinations thereof. Diamine crosslinking agents may include twelve carbon atoms or fewer, more commonly seven or fewer. Other cross-linking agents include various tetrols, such as erythritol and pentaerythritol, pentols, hexols, such as dipentaerythritol and sorbitol, as well as alkyl glucosides, carbohydrates, polyhydroxy fatty acid esters such as castor oil and polyoxy alkylated derivatives of poly-functional compounds having three or more reactive hydrogen atoms, such as, for example, the reaction product of trimethylolpropane, glycerol, 1,2,6-hexanetriol, sorbitol and other polyols with ethylene oxide, propylene oxide, or other alkylene epoxides or mixtures thereof, e.g., mixtures of ethylene and propylene oxides.

Non-limiting examples of chain extenders include, but are not limited to, compounds having hydroxyl or amino functional group, such as glycols, amines, diols, and water. Specific non-limiting examples of chain extenders include ethylene glycol, diethylene glycol, propylene glycol, dipropylene glycol, 1,4-butanediol, 1,3-butanediol, 1,5-pentanediol, neopentyl glycol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclohexanol, 1,2-diaminoethane, 2,4-toluenediamine, or any mixture thereof.

Catalyst

The catalyst component can affect the reaction rate and can exert influence on the open celled structures and the physical properties of the foam. The proper selection of catalyst (or catalysts) appropriately balance the competing interests of the blowing and polymerization reactions. A correct balance is needed due to the possibility of foam collapse if the blow reaction proceeds relatively fast. On the other hand, if the gelation reaction overtakes the blow reaction, foams with closed cells might result and this might lead to foam shrinkage or "pruning." Catalyzing a polyurethane foam, therefore, involves choosing a catalyst package in such a way that the gas produced becomes sufficiently entrapped in the polymer. The reacting polymer, in turn, has sufficient strength throughout the foaming process to maintain its structural integrity without collapse, shrinkage, or splitting.

The catalyst component is selected from the group consisting of tertiary amines, organometallic derivatives or salts of, bismuth, tin, iron, antimony, cobalt, thorium, aluminum, zinc, nickel, cerium, molybdenum, vanadium, copper, manganese and zirconium, metal hydroxides and metal carboxylates. Tertiary amines may include, but are not limited to, triethylamine, triethylenediamine, N,N,N',N'-tetramethylethylenediamine, N,N,N',N'-tetramethylethylenediamine, N-methylmorpholine, N-ethylmorpholine, N,N,N',N'-tetramethylguanidine, N,N,N',N'-tetramethyl-1,3-butanediamine, N,N-dimethylethanolamine, N,N-diethylethanolamine. Suitable organometallic derivatives include di-n-butyl tin bis(mercaptoacetic acid isooctyl ester), dimethyl tin dilaurate, dibutyl tin dilaurate, dibutyl tin sulfide, stannous octoate, lead octoate, and ferric acetylacetonate. Metal hydroxides may include sodium hydroxide and metal carboxylates may include potassium acetate, sodium acetate or potassium 2-ethylhexanoate.

Blowing Agents

Polyurethane foam production may be aided by the inclusion of a blowing agent to produce voids in the polyurethane matrix during polymerization. The blowing agent promotes the release of a blowing gas which forms cell voids in the polyurethane foam. The blowing agent may be a physical blowing agent or a chemical blowing agent. The physical blowing agent can be a gas or liquid, and does not chemically react with the polyisocyanate composition. The liquid physical blowing agent may evaporate into a gas when heated, and may return to a liquid when cooled. The physical blowing agent may reduce the thermal conductivity of the polyurethane foam. Suitable physical blowing agents may include liquid carbon dioxide, acetone, and combinations thereof. Physical blowing agents may have a zero ozone depletion potential. Chemical blowing agents refers to blowing agents which chemically react with the polyisocyanate composition.

Suitable blowing agents may also include compounds with low boiling points which are vaporized during the exothermic polymerization reaction. Such blowing agents may be inert or they have low reactivity and therefore it is likely that they will not decompose or react during the polymerization reaction. Examples of blowing agents include, but are not limited to, water, carbon dioxide, nitrogen gas, acetone, and low-boiling hydrocarbons such as cyclopentane, isopentane, n-pentane, and their mixtures. Previously, blowing agents such as chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), and hydrochlorfluoroolefins (HCFOs), were used, though such agents are not as environmentally friendly. Other suitable blowing agents include water that reacts with isocyanate to produce a gas, carbamic acid, and amine, as shown below in Scheme 11.

Scheme 11. Blowing reaction during the polymerization process

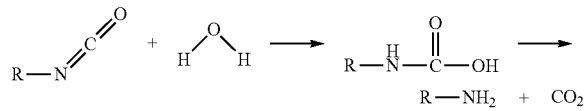

Cell Stabilizers

Cell stabilizers may include, for example, silicone surfactants or anionic surfactants. Examples of suitable silicone surfactants include, but are not limited to, polyalkylsiloxanes, polyoxyalkylene polyol-modified dimethylpolysiloxanes, alkylene glycol-modified dimethylpolysiloxanes, or any combination thereof. Suitable anionic surfactants include, but are not limited to, salts of fatty acids, salts of sulfuric acid esters, salts of phosphoric acid esters, salts of sulfonic acids, and combinations of any of these. Such surfactants provide a variety of functions, reducing surface tension, emulsifying incompatible ingredients, promoting bubble nucleation during mixing, stabilization of the cell walls during foam expansion, and reducing the defoaming effect of any solids added. Of these functions, a key function is the stabilization of the cell walls, without which the foam would behave like a viscous boiling liquid.

Additional Additives

If desired, the polyurethane foams can have incorporated, at an appropriate stage of preparation, additives such as pigments, fillers, lubricants, antioxidants, fire retardants, mold release agents, synthetic rubbers and the like which are commonly used in conjunction with polyurethane foams.

Flexible and Rigid Foam Embodiments

In some embodiments, the polyurethane foam may be a flexible foam, where such composition includes: (i) at least one polyol composition derived from a natural oil (palm oil) based metathesized triacylglycerols component; (ii) at least one polyisocyanate component, wherein the ratio of hydroxy groups in the at least one polyol to isocyanate groups in the at least one polyisocyanate component is less than 1; (iii) at least one blowing agent; (iv) at least one cell stabilizer component; and (v) at least one catalyst component; wherein the composition has a wide density range, which can be 85 kgm$^{-3}$ to 260 kgm$^{-3}$, but can in some instances be much wider. The flexible foam can have a wide density range, and in some embodiments, the range can be 85 kgm$^{-3}$ to 260 kgm$^{-3}$. In some embodiments, the range may be broader than this range.

In other embodiments, the polyurethane foam may be a rigid foam, where the composition includes: (i) at least one polyol derived from a natural oil (palm oil) based metathesized triacylglycerols component; (ii) at least one polyisocyanate component, wherein the ratio of hydroxy groups in the at least one polyol to isocyanate groups in the at least one polyisocyanate component is less than 1; (iii) at least one cross-linking agent; (iv) at least one blowing agent; (v) at least one cell stabilizer component; and (vi) at least one catalyst component; wherein the composition has a wide density range, which can be 85 kgm$^{-3}$ to 260 kgm$^{-3}$, but can in some instances be much wider. The rigid foam can have a wide density range, and in some embodiments, the range can be 85 kgm$^{-3}$ to 260 kgm$^{-3}$ In some embodiments, the range may be broader than this range.

Analytical Methods for PMTAG Polyol Foam Analysis

The PMTAG Polyol foam was analyzed using different techniques. These techniques can be broken down into: (i) chemistry characterization techniques, including NCO value and Fourier Transform infrared spectroscopy (FTIR); and (ii) physical characterization methods, including thermogravimetric analysis (TGA), differential scanning calorimetry (DSC), scanning electron microscopy (SEM) and compressive test.

Chemistry Characterization Techniques of PMTAG Polyol Foam

The amount of reactive NCO (% NCO) for distilled and non-distilled diisocyanates was determined by titration with dibutylamine (DBA). MDI (2±0.3 g) was weighed into 250 ml conical flasks. 2N DBA solution (20 ml) was pipetted to dissolve MDI. The mixture is allowed to boil at 150° C. until the vapor condensate is at an inch above the fluid line. The flasks were cooled to RT and rinsed with methanol to collect all the products. 1 ml of 0.04% bromophenol blue indicator is then added and titrated against 1N HCl until the color changes from blue to yellow. A blank titration using DBA is also done.

The equivalent weight (EW) of the MDI is given by Eq. 2

$$EW = \frac{W \times 1000}{(V_1 - V_2) \times N} \quad \text{Eq. 2}$$

where W is the weight of MDI in g, $V_1$ and $V_2$ are the volume of HCl for the blank and MDI samples, respectively. N is the concentration of HCl. The NCO content (%) is given by Eq. 3:

$$\% \text{ NCO content} = \frac{42}{EW} \times 100 \quad \text{Eq. 3}$$

FTIR spectra were obtained using a Thermo Scientific Nicolet 380 FT-IR spectrometer (Thermo Electron Scientific Instruments, LLC, USA) equipped with a PIKE MIRacle™ attenuated total reflectance (ATR) system (PIKE Technologies, Madison, Wis., USA.). Foam samples were loaded onto the ATR crystal area and held in place by a pressure arm, and sample spectra were acquired over a scanning range of 400-4000 $cm^{-1}$ for 32 repeated scans at a spectral resolution of 4 $cm^{-1}$.

Physical Characterization Techniques of PMTAG Polyol Foam

TGA was carried out on a TGA Q500 (TA Instruments, DE, USA) equipped with a TGA heat exchanger (P/N 953160.901). Approximately 8.0-15.0 mg of sample was loaded in the open TGA platinum pan. The sample was heated from 25 to 600° C. under dry nitrogen at a constant rate of 10° C./min.

DSC measurements were run on a Q200 model (TA Instruments, New Castle, Del.) under a nitrogen flow of 50 mL/min. PMTAG Polyol Foam samples between 3.0 and 6.0 (±0.1) mg were run in hermetically sealed aluminum DSC pans. In order to obtain a better resolution of the glass transition, PMTAG Polyol foams were investigated using modulated DSC following ASTM E1356-03 standard. The sample was first equilibrated at −90° C. and heated to 150° C. at a constant rate of 5.0° C./min (first heating cycle), held at 150° C. for 1 min and then cooled down to −90° C. with a cooling rate of 5° C./min, and subsequently reheated to 150° C. at the same rate (second heating cycle). Modulation amplitude and period were 1° C. and 60 s, respectively. The "TA Universal Analysis" software was used to analyze the DSC thermograms.

SEM was performed on a Tescan Vega II scanning electron microscope. The scanning electron microscopy was performed on model Tescan Vega II, was used under standard operating conditions (10 keV beam) to examine the pore structure of the foams. A sub-sample of approximately 2 cm×2 cm and 0.5 cm thick was cut from the center of each sample. The sample was coated with a thin layer of carbon (~30 nm thick) using an Emitech K950X turbo evaporator to provide electrical conductivity in the SEM chamber and prevent the buildup of electrons on the surface of the sample. All images were acquired using a secondary electron detector to show the surface features of the samples.

The compressive strength of the foams was measured at room temperature using a texture analyzer (Texture Technologies Corp, NJ, USA). Samples were prepared in cylindrical Teflon molds of 60-mm diameter and 36-mm long. The cross head speed was 3.54 mm/min with a load cell of 500 kgf or 750 kgf. The load for the rigid foams was applied until the foam was compressed to approximately 15% of its original thickness, and compressive strengths were calculated based on the 10% deformation and 6% deformation. The load for the flexible foams was applied until the foam was compressed to approximately 65% of its original thickness, and compressive strengths were calculated based on 5, 10 and 25% deformation.

Polymerization Conditions

Materials

The materials used to produce the foams are listed in Table 11. The PMTAG Polyols were obtained from MTAG of palm oil as described above. The hydroxyl value (OH value) and acid value of the PMTAG Polyol, measured using ASTM D1957-86 and ASTM D4662-03, respectively, are listed in Table 12. There were no free fatty acids detected by $^1$H-NMR. There was also no signal that can be associated with the loss of free fatty acids in the TGA of the PMTAG Polyol. The acid value reported in Table 12 was probably due to the hydrolysis of PMTAG Polyol during the actual titration, which uses strong base as the titrant, with the result that the actual titration causes hydrolysis.

TABLE 11

Materials used in the polymerization reaction.

| Polyol | Isocyanate | Catalyst | Cross linker | Surfactant | Blowing agent |
|---|---|---|---|---|---|
| PMTAG Polyol | Distilled and Non-distilled MDI[a] | DBTDL[b], 95% DMEA[c], 99.5% | Glycerin, 99.5% | TEGOSTAB ® B-8404[d] | $CO_2$ from addition of 2% deionized $H_2O$ |

[a]MDI: Diphenylmethane diisocyanate, from Bayer Materials Science, Pittsburgh, PA
[b]DBTDL: Dibutin Dilaurate, main catalyst, from Sigma Aldrich, USA
[c]DMEA: N,N-Dimethylethanolamine, co-catalyst, from Fischer Chemical, USA
[d]TEGOSTAB ® B-8404, Polyether-modified, a general-purpose silicone surfactant, from Goldschmidt Chemical, Canada

TABLE 12

OH and acid value of PMTAG Polyol

| | OH-value (mg KOH/g) | Acid-value (mg KOH/g) |
|---|---|---|
| PMTAG Polyol | 155 | 2 |

Distillation of MDI

Figure 30:
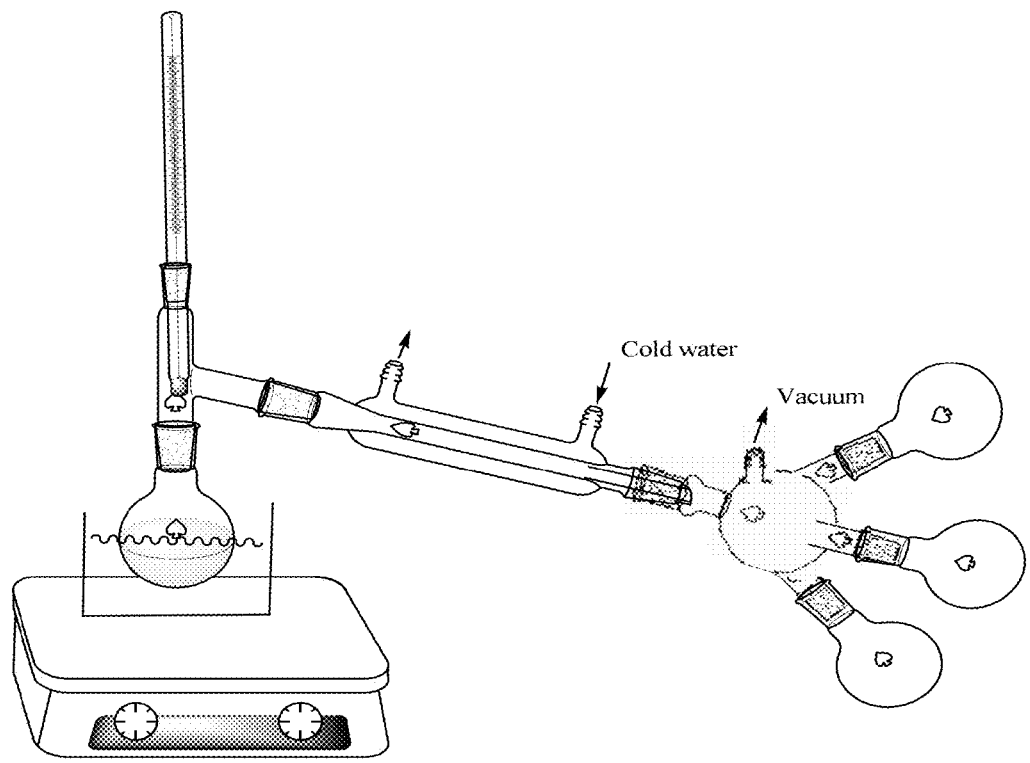
FIG. 30 depicts a setup for distillation of MDI.

The physical properties of the crude MDI as provided by the supplier are reported in Table 13. MDI was distilled in order to separate the 4,4' MDI from its mixed isomers and polymeric constituents, and in order to assess the relative properties of foams produced using distilled vs. non-distilled MDI. Around 60 g of crude MDI was transferred to a 250 mL round bottom (RB) flask fitted with a thermometer and connected to a condenser with continuous water flow. The RB was placed in an oil bath. The condenser was connected to three 100 mL collection flasks through an adapter that is connected to a vacuum pump (FIG. 30). A solvent trap kept in ice was attached to the vacuum to collect any solvents and/or impurities. Under reduced pressure the temperature of the hot plate was raised gradually to 210° C. MDI distilled out between 173-176° C. and at 500 mTorr. The assembly was insulated using cotton wool wrapped around the reaction vessel and maintained with aluminum foil. The initial fraction was discarded and the pure fraction (50% yields) was collected and stored in the fridge for further use. The % NCO content of the distilled and non-distilled MDI is listed in Table 14.

TABLE 13

Physical properties of crude MDI.

| Property | Value |
|---|---|
| Form | Dark brown liquid |
| Boiling Point (° C.) | 208 |
| NCO content (% wt.) | 31.5 |
| Equivalent weight | 133 |
| Functionality | 2.4 |
| Viscosity @ 25° C. (mPas) | 200 |
| Bulk density (kgm$^{-3}$) | 1234 |
| Composition | Polymeric MDI: 40-50% |
| | (4,4' diphenylmethane diisocyanate): 30-40% |
| | MDI mixed isomers: 15-25% |

TABLE 14

NCO content of distilled and non-distilled MDI

| Sample | EW (g/mol) | % NCO content |
|---|---|---|
| Distilled MDI | 138.4 ± 1.8 | 30.4% |
| non-Distilled | 133.8 ± 2.0 | 31.4% |

Figure 31A:
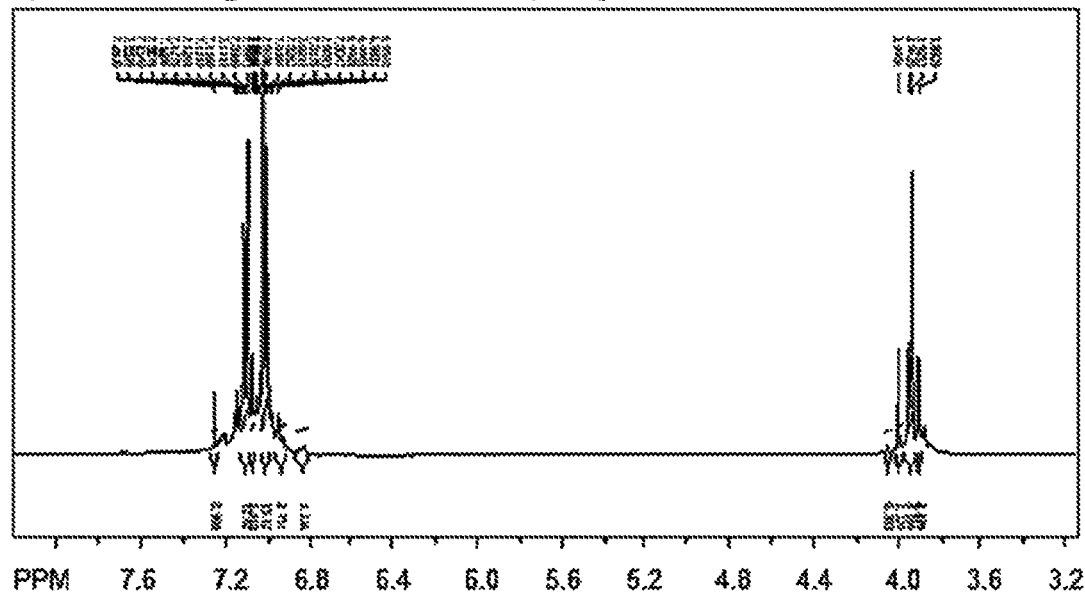
FIG. 31a depicts a $^1$H-NMR spectrum of non-distilled MDI.
Figure 31B:
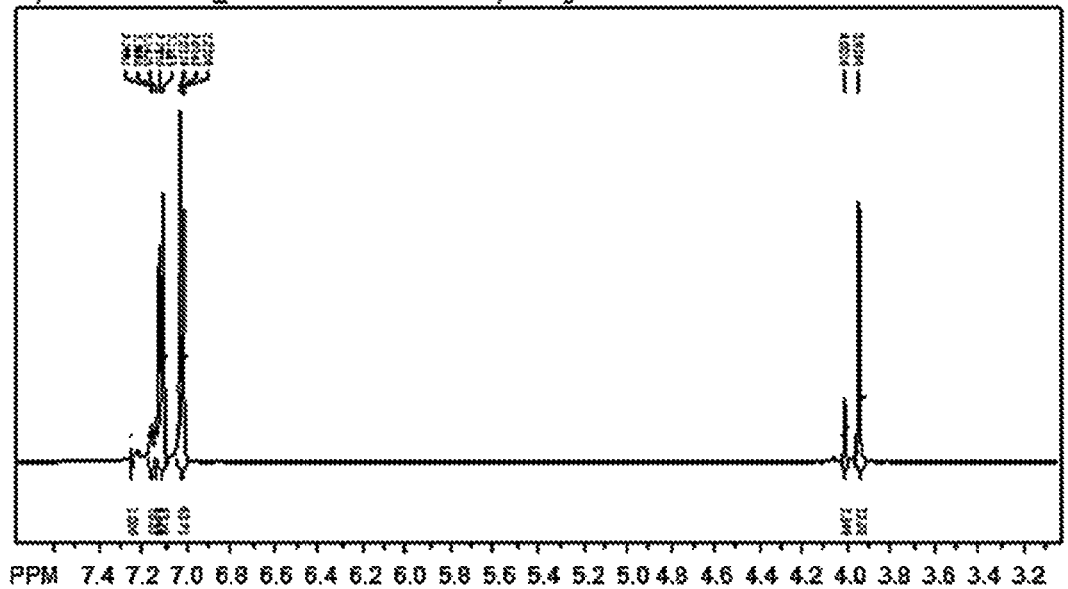
FIG. 31b depicts a $^1$H-NMR spectrum of distilled MDI

FIG. 31a and FIG. 31b show the $^1$H-NMR spectra of both non-distilled and distilled MDI, respectively. Table 15 shows the corresponding chemical shift values. The $^1$H-NMR data confirmed the separation of the oligomers from the monomeric components of MDI.

TABLE 15

$^1$H-NMR data of the diisocyanates

| | Protons | | | | | | | |
|---|---|---|---|---|---|---|---|---|
| | p, o, m (CH=CH) (NCO at 2-position of Benzene) | m(CH=CH) NCO at 4 position of Benzene) | o(CH=CH) (NCO at 4 position of Benzene) | CH$_2$ in 2,2' isomer | CH$_2$ in 2,4' isomer | CH$_2$ in 4,4' isomer | CH$_2$ in oligomers | CH$_2$ in other isomers |
| Distilled MDI | | | | | | | | |
| Chemical shift (ppm) | 7.1466-7.1661 | 7.1155-7.1320 | 7.0208-7.0374 | 4.04 | 4.0016 | 3.9386 | | |
| NON Distilled MDI | | | | | | | | |
| Chemical shift (ppm) | 7.1386-7.1599 | 7.0779-7.1275 | 7.0175-7.0384 | 4.04 | 3.9904 | 3.9420 | 3.9253 | 3.8929 |

Synthesis of Foams from PMTAG Polyol

The amount of each component of the polymerization mixture was based on 100 parts by weight of total polyol. The amount of MDI was taken based on the isocyanate index 1.2. All the ingredients, except MDI, were weighed into a beaker and MDI was added to the beaker using a syringe, and then mechanically mixed vigorously for 10 to 20 s. At the end of the mixing period, mixed materials was added into a cylindrical Teflon mold (60 mm diameter and 35 mm long) which was previously greased with silicone release agent and sealed with a hand tightened clamp. The sample was cured for four (4) days at 40° C. and post cured for one (1) day at room temperature.

Rigid foam formulation was determined based on a total hydroxyl value of 450 mg KOH/g according to prior teachings. Table 16a presents the formulation recipe used to prepare the rigid foams. Note that in this case, around 16.2 parts of glycerin were added into the reaction mixture in order to reach the targeted hydroxyl value of 450 mg KOH/g. Flexible Foam formulation was based on a total hydroxyl value of 155 mg KOH/g according to prior teachings. Table 16b presents the formulation recipe used to prepare the flexible foams. In this case, no glycerin was added into the reaction mixture, and the catalyst amount was fixed to 0.1 parts for proper control of the polymerization reaction.

TABLE 16a

Formulation Recipe for Rigid Foams

| Ingredient | Part |
|---|---|
| PMTAG Polyol | 100 |
| OH:NCO ratio | 1:1.2 |
| Glycerin | 16.2 |
| Water | 2 |
| Surfactant | 2 |
| Catalyst | 1 |
| Co-catalyst | 1 |
| Mixing Temperature (° C.) | 40 |
| Oven Temperature (° C.) | 40 |

TABLE 16b

Formulation Recipe for Flexible Foams

| Ingredient | Part |
|---|---|
| PMTAG Polyol | 100 |
| OH:NCO ratio | 1:1.2 |

TABLE 16b-continued

Formulation Recipe for Flexible Foams

| Ingredient | Part |
|---|---|
| Glycerin | 0 |
| Water | 2 |
| Surfactant | 2 |
| Catalyst | 0.1 |
| Co-catalyst | 0.1 |
| Mixing Temperature (° C.) | 40 |
| Oven Temperature (° C.) | 40 |

PMTAG Polyol Foam Produced Using Non-Distilled MDI

Figure 32A:
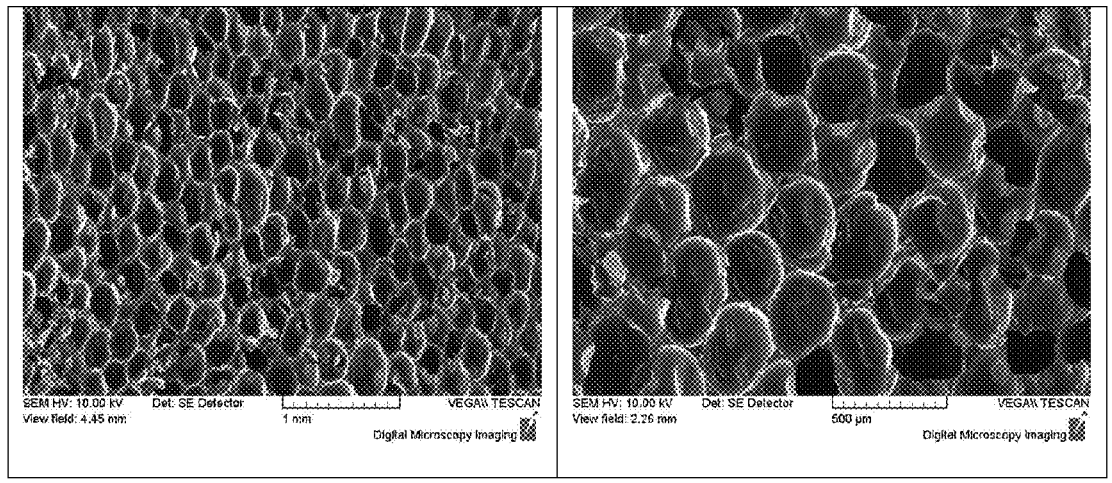
FIG. 32a depicts a SEM micrograph of rigid PMTAG polyol foams.
Figure 32B:
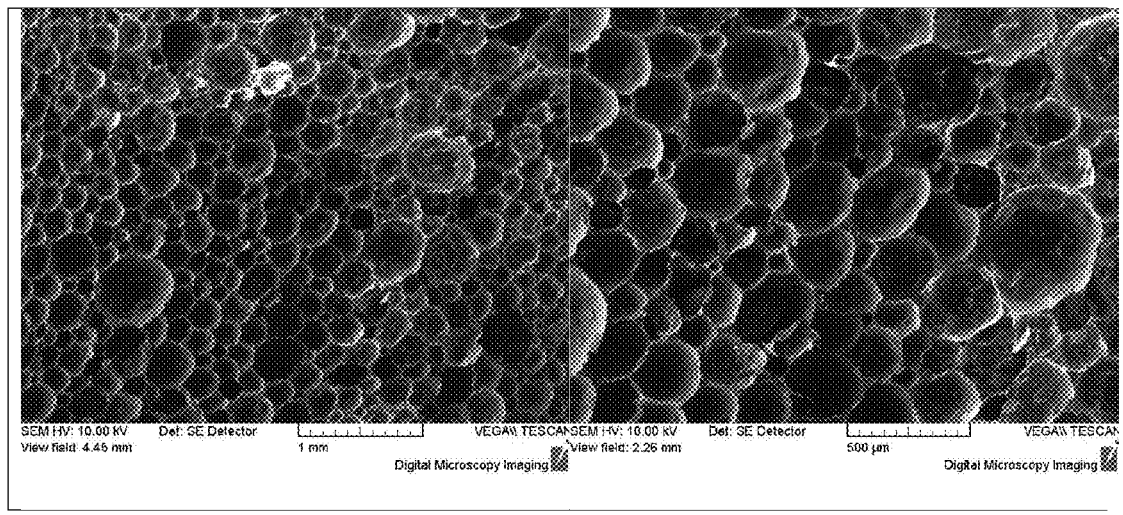
FIG. 32b depicts a SEM micrograph of flexible PMTAG polyol foams.

Five different rigid foams with densities of 93, 127, 156, 165 and 250 kgm$^{-3}$ and five different flexible foams with densities of 106, 126, 146, 164, and 193 kgm$^{-3}$ were prepared from the PMTAG Polyol using non-distilled MDI. The resulting foams presented a homogenous closed cell structure elucidated through SEM micrographs, examples of which are shown in FIGS. 32a and 32b for the rigid and flexible PMTAG Polyol foams, respectively.

FTIR of PMTAG Polyol Foam

Figure 33:
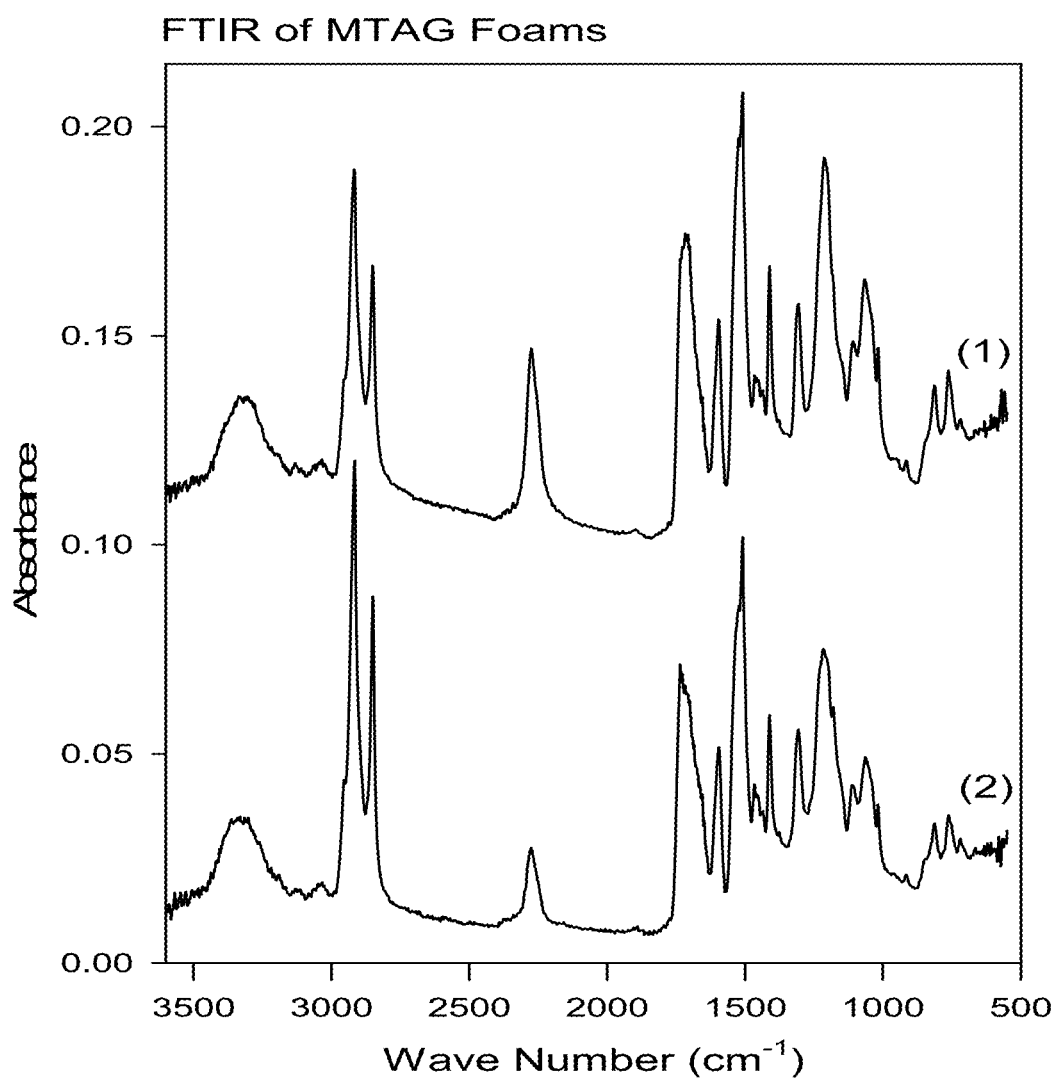
FIG. 33 depicts a FTIR spectra of the PMTAG polyol foams. Curve (1): Rigid PMTAG polyol foam, 250 kg/m³, Curve (2): Rigid PMTAG polyol foam, 165 kg/m³.

FTIR spectra of PMTAG Polyol Foams are shown in FIG. 33. Table 17 lists the characteristic vibrations of the foams. The broad absorption band observed at 3300-3400 cm$^{-1}$ in the foam is characteristic of NH group associated with the urethane linkage. The weak band at 2270 cm$^{-1}$ indicates that free NCO are present in the foam. The overlapping peaks between 1710 and 1735 cm$^{-1}$ suggest the formation of urea, isocyanurate and free urethane in the PMTAG Polyol foams.

The CH$_2$ stretching vibration is clearly visible at 2800-3000 cm$^{-1}$ region in the spectra. The band centered at 1700 cm$^{-1}$ is characteristic of C=O, which demonstrates the formation of urethane linkages. The band at 1744 cm$^{-1}$ is attributed to the C=O stretching of the ester groups. The sharp band at 1150-1160 cm$^{-1}$ and 1108-1110 cm$^{-1}$ are the O—C—C and C—C(=O)—O stretching bands, respectively, of the ester groups. The band at 1030-1050 cm$^{-1}$ is due to CH$_2$ bend.

TABLE 17

FTIR data of PMTAG Polyol foam

| Moiety | Wavelengths (cm$^{-1}$) |
|---|---|
| H-bonded and free N—H groups | 3300-3400 |
| Free NCO | 2270 |
| Urea | 1717 |
| Isocyanurate | 1710 |
| Free Urethane | 1735 |

Physical Properties of PMTAG Polyol Foams

Thermal Stability of PMTAG Polyol Foams

Figure 34A:
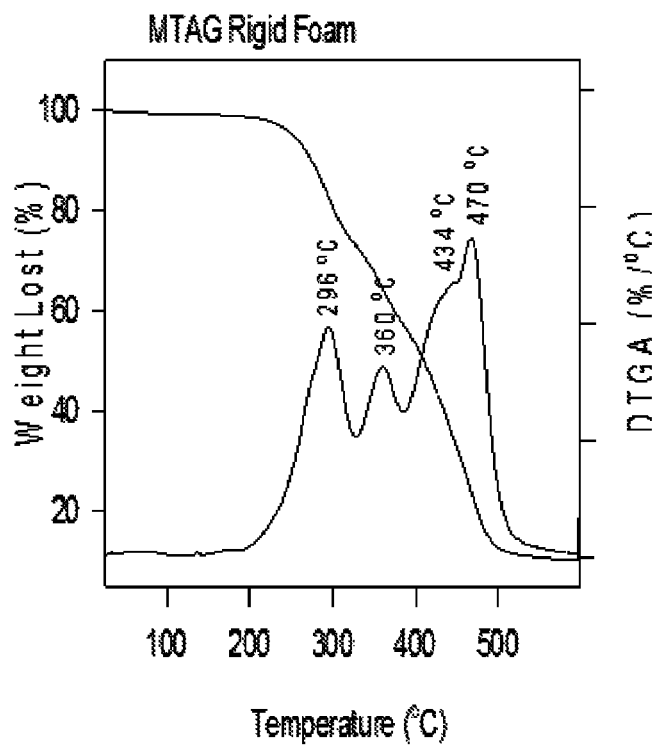
FIG. 34a depicts a TGA and DTG curve of a rigid PMTAG polyol foam.
Figure 34B:
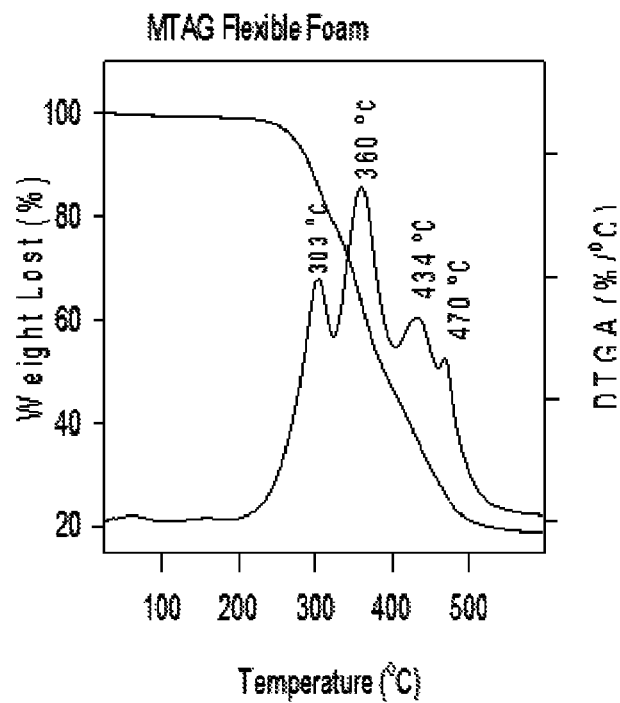
FIG. 34b depicts a TGA and DTG curve of flexible PMTAG polyol foam.

The thermal stability of the PMTAG Polyol foams were determined by TGA. TGA and DTG curves of rigid and flexible PMTAG Polyol foams are shown in FIGS. 34a and 34b, respectively. Table 18 lists the onset temperature ($T_{on}$) of degradation of PMTAG Polyol foam determined at 1, 5 and 10% weight loss. The initial step of decomposition indicated by the DTG peak at 303° C. with a total weight loss of 15% is due to the degradation of urethane linkages, which involves dissociations to the isocyanate and the alcohol, amines and olefins or to secondary amines. The second decomposition step in the range of temperature between 330 and 430° C. and indicated by the DTG peak at 360° C. with a total weight loss of 65%, was due to degradation of the ester groups. The degradation steps at higher temperatures were attributed to the degradation of more strongly bonded fragments.

TABLE 18

Onset temperature of PMTAG Polyol Foam degradation determined at 1, 5 and 10% weight loss ($T_{1\%}$, $T_{5\%}$ and $T_{10\%}$, respectively)

| | $T_{1\%}$ (° C.) | $T_{5\%}$ (° C.) | $T_{10\%}$ (° C.) |
|---|---|---|---|
| Rigid PMTAG Polyol Foam | 180 | 253 | 275 |
| Flexible PMTAG Polyol Foam | 216 | 272 | 292 |

Thermal Behavior of PMTAG Polyol Foam

Figure 35A:
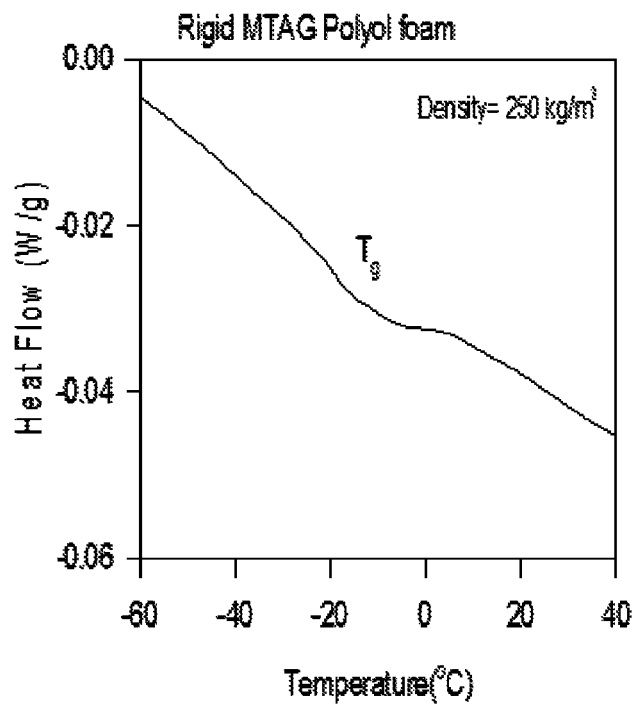
FIG. 35a depicts a DSC thermogram of rigid PMTAG polyol foam.
Figure 35B:
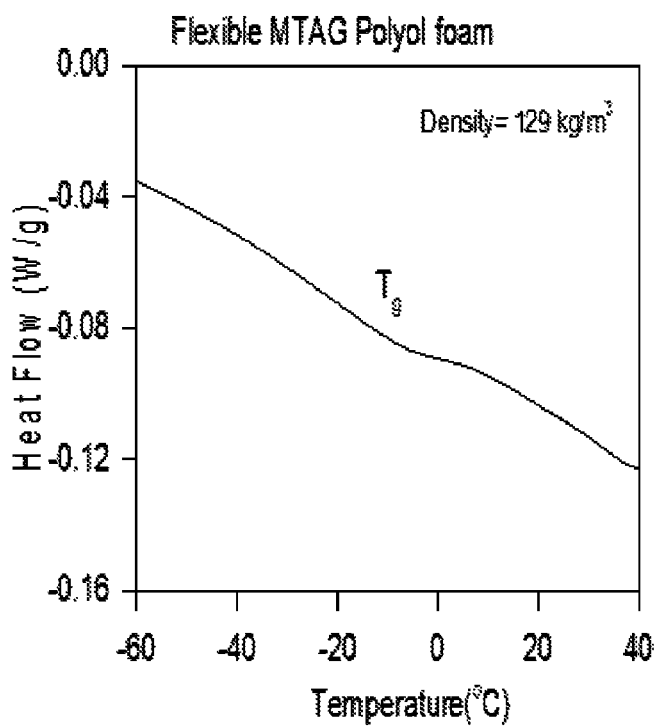
FIG. 35b depicts a DSC thermogram of flexible PMTAG polyol foam.

Curves obtained from the modulated DSC obtained during the second heating cycle of the rigid and flexible PMTAG Polyol foams are shown in FIGS. 35a and 35b, respectively. Table 19 lists the glass transition temperature ($T_g$) of the rigid and flexible PMTAG Polyol foams produced. As can be seen, the glass transition temperature was well below room temperature (RT) indicating that the foams are in the rubbery state at RT.

TABLE 19

Glass transition temperature ($T_g$) of PMTAG Polyol foams produced.

| | Rigid PMTAG Polyol Foam | Flexible PMTAG Polyol Foam |
|---|---|---|
| $T_g$ (° C.) | −17.59 | −21.46 |

Compressive Strength of Rigid PMTAG Polyol Foams

Figure 36:
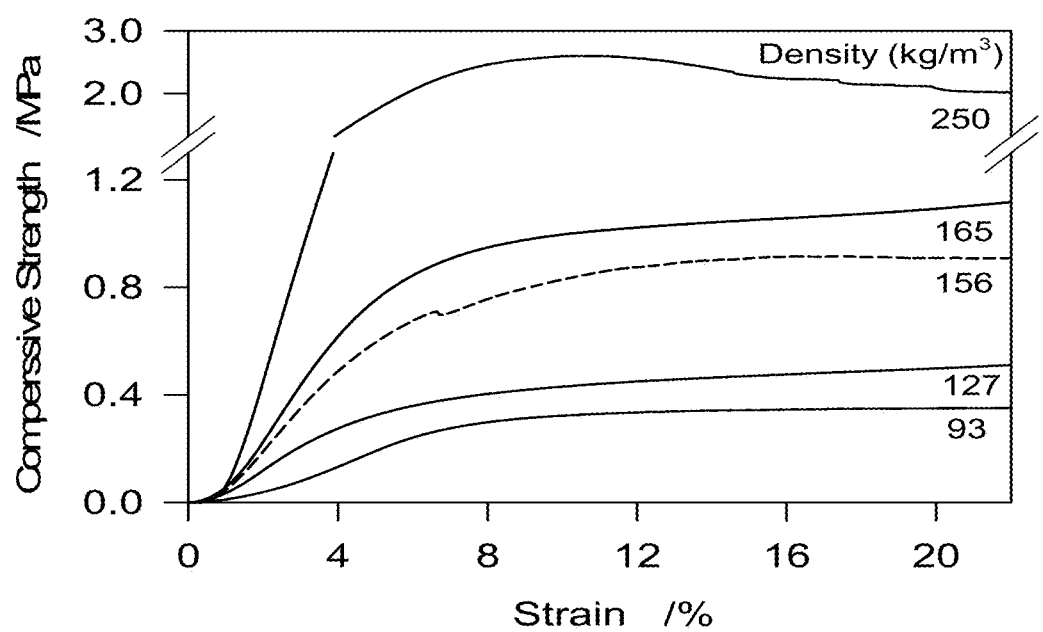
FIG. 36 depicts a stress versus strain curve of rigid PMTAG polyol foams. Density (kg/m³) of the foam is indicated at the right hand-side below each curve.
Figure 37A:
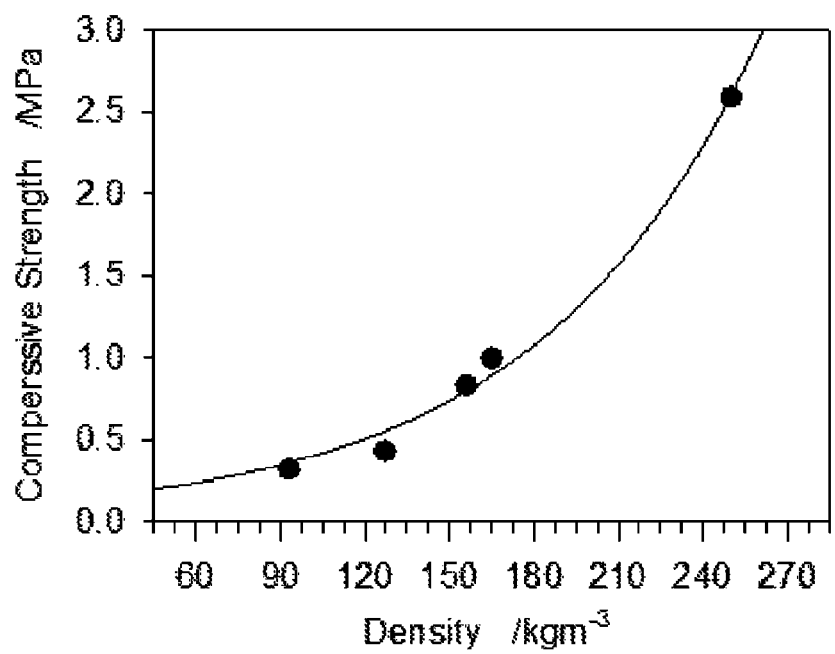
FIG. 37a depicts a density versus compressive strength of rigid PMTAG Polyol foams at 10% deformation.
Figure 37B:
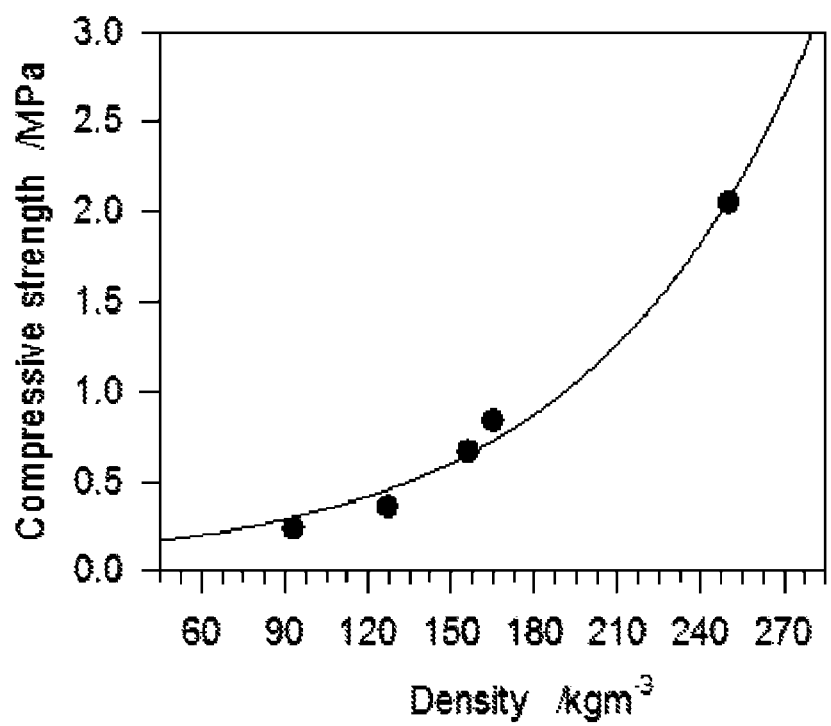
FIG. 37b depicts a density versus compressive strength of rigid PMTAG Polyol foams at 6% deformation.

The strength of the foams were characterized by the compressive stress-strain measurements. Stress strain curves of the different rigid foams are shown in FIG. 36. The compressive strength values for the rigid PMTAG Polyol foams are listed in Table 20. FIGS. 37A and 37B show the compressive strength of rigid PMTAG Polyol foams versus density curves at (a) 10% deformation and (b) 6% deformation.

The highest compressive strength value (2.59 MPa) was obtained for the rigid PMTAG Polyol foam with the highest density, e.g., 250 kg/m$^3$. As shown by FIGS. 37A and 37B, compressive strength value increased exponentially with increasing foam density. The fitted parameters to an exponential growth function (Eq. 4) are listed in Table 21.

$$f = a \times e^{bx} \qquad \text{Eq. 4}$$

TABLE 20

Compressive strength at 10% deformation of rigid PMTAG Polyol foams of different densities.

| Density (kg/m$^3$) | Compressive strength (MPa) |
|---|---|
| 250 | 2.59 |
| 165 | 1.00 |
| 156 | 0.83 |
| 127 | 0.43 |
| 93 | 0.32 |

TABLE 21

Fit parameters of the density versus compressive strength of rigid PMTAG Polyol foam to an exponential growth function (Eq. 4).

| Deformation | R$^2$ | a | B |
|---|---|---|---|
| 10% | 0.991133 | 0.112 ± 0.021 | 0.013 ± 0.003 |
| 6% | 0.987433 | 0.096 ± 0.021 | 0.012 ± 0.001 |

The compressive strength is highly dependent on the cellular structure of the foam. In the case of the rigid PMTAG Polyol foams, the high mechanical strength of the foams was due to compact and closed cells as shown in FIG. 32a. The cell density from the SEM micrographs is ~21 cells per mm$^2$. The elongation of the cells are due to the direction of rise and the boundaries caused by the walls of the cylindrical mold.

Compressive Strength of Flexible PMTAG Polyol Foams

Figure 38:
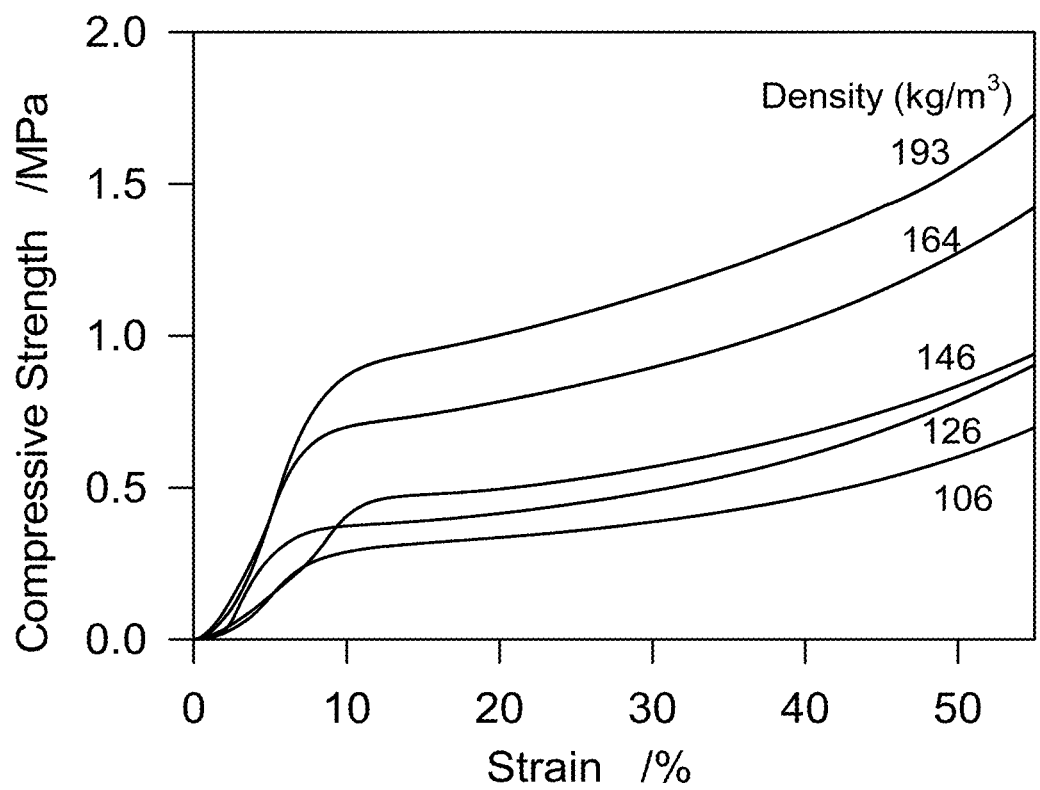
FIG. 38 depicts a compressive strength versus strain of flexible PMTAG polyol foams. Density (kg/m³) of the foams is reported at the right-hand side of each curve.
Figure 39:
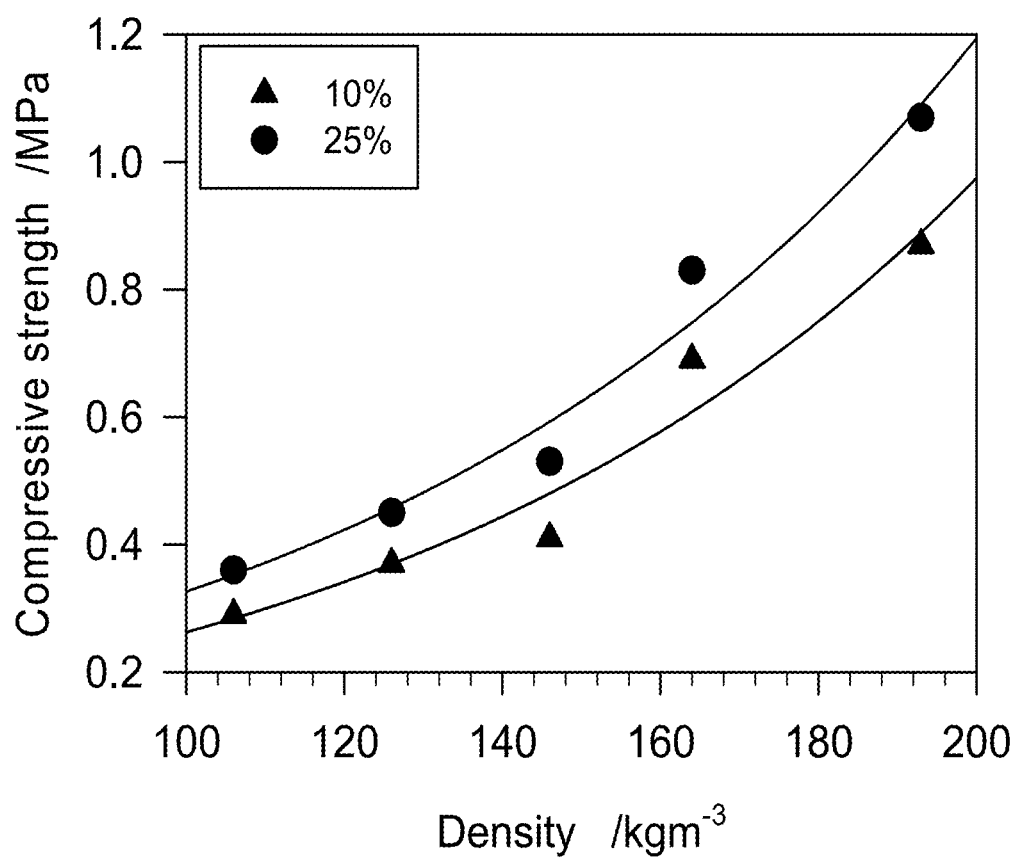
FIG. 39 depicts the density versus compressive strength of flexible PMTAG Polyol foams at their 10 and 25% deformation.

FIG. 38 shows the compressive strength versus strain of flexible PMTAG Polyol foams produced using non-distilled MDI. FIG. 39 shows the compressive strength versus density curves obtained at 10 and 25% deformation of the flexible PMTAG Polyol foams, and Table 22 lists the related data. As can be seen in FIG. 39, the compressive strength of the flexible foams increased exponentially with density. The fitted parameters to an exponential growth function (Eq. 4) are listed in Table 23.

TABLE 22

Compressive strength value at 10 and 25% deformation of flexible PMTAG Polyol foams

| Density | Compressive Strength (MPa) | |
|---|---|---|
| (kgm$^{-3}$) | at 10% | at 25% |
| 106 | 0.29 | 0.36 |
| 126 | 0.37 | 0.45 |
| 146 | 0.41 | 0.53 |
| 164 | 0.69 | 0.83 |
| 193 | 0.87 | 1.07 |

TABLE 23

Fit parameters of the density versus compressive strength of flexible PMTAG Polyol foams to an exponential growth function (Eq. 4).

| Deformation | $R^2$ | A | b |
|---|---|---|---|
| 10% | 0.949503 | 0.0708 ± 0.022 | 0.013 ± 0.002 |
| 25% | 0.968084 | 0.0892 ± 0.022 | 0.013 ± 0.001 |

Figure 40:
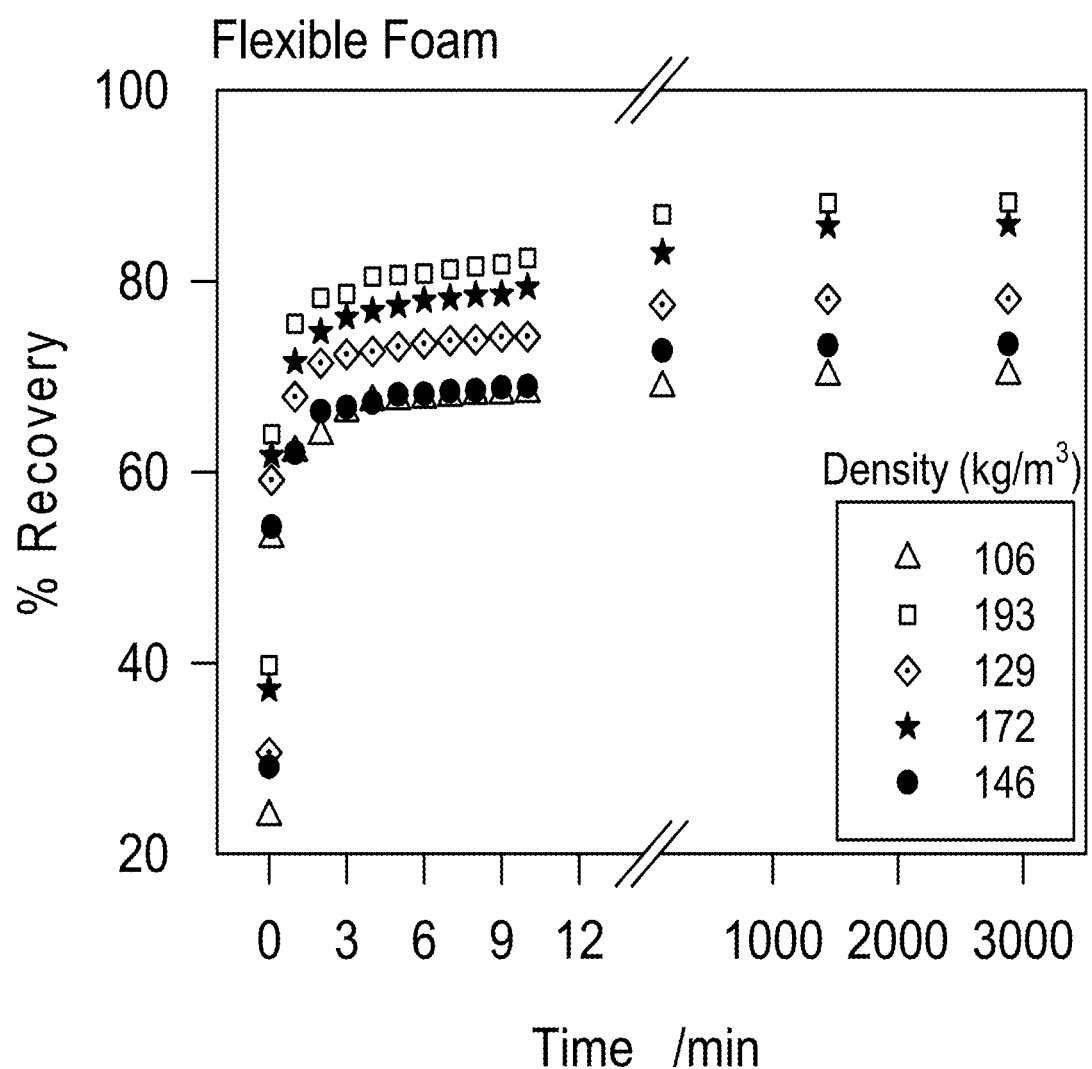
FIG. 40 depicts a % recovery of flexible PMTAG polyol foams as a function of time.

FIG. 40 shows the percentage of recovery of flexible PMTAG Polyol foams as a function of time. Note that ~70-80% recovery of flexible PMTAG Polyol foams was achieved after 10 min. The flexible PMTAG Polyol foam having a density of 193 kgm$^{-3}$ presented 91% recovery in less than 10 min.

Figure 41:
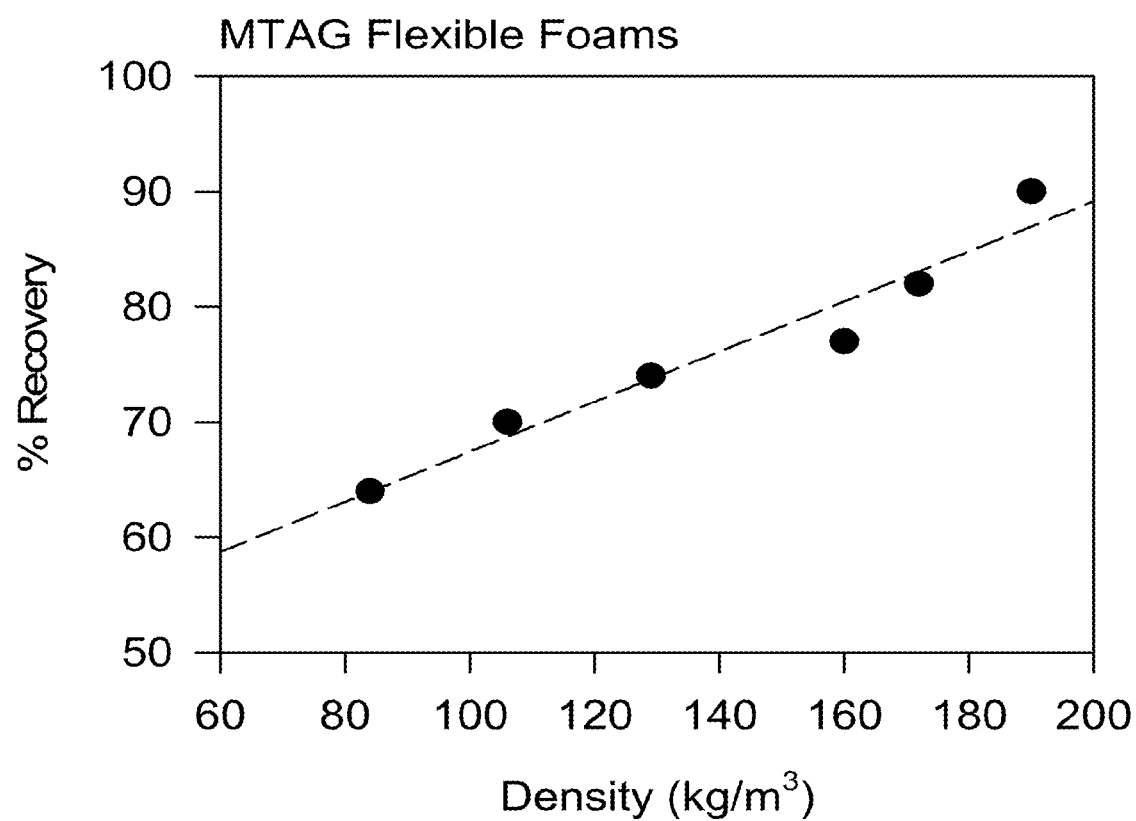
FIG. 41 depicts a density versus % recovery of flexible PMTAG polyol foams after 48 hours. Dashed line is a fit to a straight line.

FIG. 41 shows the percentage of recovery after 48 hours versus density of the flexible foams. The trend observed in FIG. 41 also confirmed that the % recovery of flexible PMTAG Polyol foam is proportional to the density of the foams. The fitted parameters to a linear function (Eq. 5) are listed in Table 24.

$$f = y_0 + ax \qquad \text{Eq. 5}$$

TABLE 24

Fit parameters of the density versus % Recovery of flexible PMTAG Polyol foams after 48 hours to a linear function (Eq. 5).

| $R^2$ | $y_0$ | a |
|---|---|---|
| 0.942570 | 45.738 ± 3.89 | 0.217 ± 0.027 |

PMTAG Polyol Foam Produced Using Distilled MDI

Figure 42:
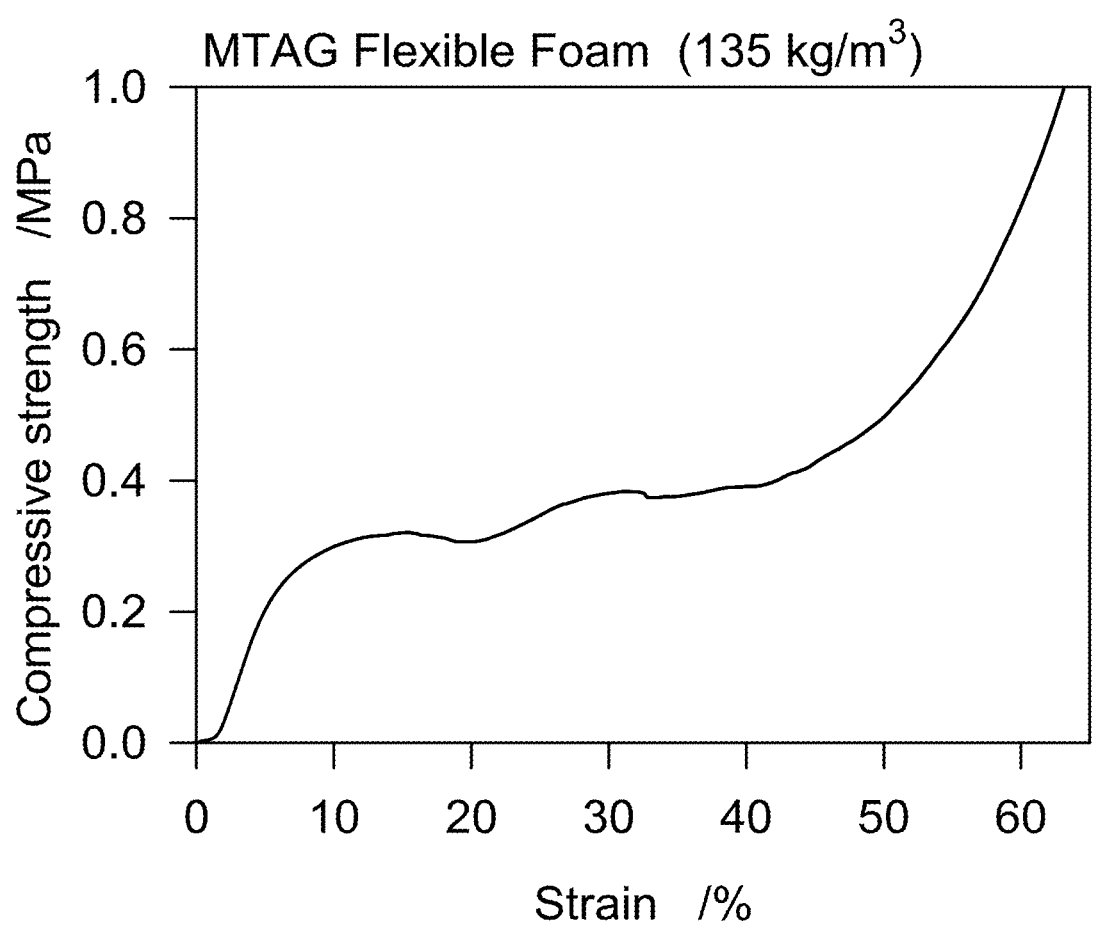
FIG. 42 depicts a compressive strength versus strain plot of flexible PMTAG foams obtained using distilled MDI. Density of presented sample=135 kg/m³.

A flexible PMTAG Polyol foam having density 135 kgm$^{-3}$ was produced using distilled MDI. FIG. 42 shows its compressive strength versus strain plot. As listed in Table 25, its compressive strength at 10 and 25% deformation was found to be 0.29 MPa and 0.35 MPa, respectively.

TABLE 25

Comparison of compressive strength of flexible PMTAG Polyol foams made from distilled and non-distilled MDI.

| Density | | Compressive Strength (MPa) @ | |
|---|---|---|---|
| (kgm$^{-3}$) | MDI Type | 10% | 25% |
| 106 | non-distilled MDI | 0.29 | 0.36 |
| 126 | non-distilled MDI | 0.37 | 0.45 |
| 146 | non-distilled MDI | 0.41 | 0.53 |
| 135 | Distilled MDI | 0.29 | 0.35 |

From Table 25, it was found that the foam with density 135 kgm$^{-3}$ prepared from distilled MDI shows almost equal compressive strength to the foam produced using non-distilled MDI with a density of 106 kgm$^{-3}$. At 25% percent deformation the 106 kgm$^{-3}$ foam showed better compressive strength than the 135 kgm$^{-3}$ foam. This may be due to the absence of oligomers in the distilled MDI, which is accountable for the higher compressive strength of the foams from non-distilled MDI.

Mixtures of PMTAG Polyol with Polyether Polyol in Flexible Foam Applications

The performance of PMTAG Polyol in comparison to a commercial Natural Oil Based Polyol (NOP) as drop-in replacements for a conventional polyether polyol in a model high resilient (HR) flexible polyurethane foam formulation was studied.

Agrol 3.6 polyol from BioBased Technologies was selected as a reference NOP in the comparative study. Agrol 3.6 polyol is well established commercial soy-based polyol suitable for flexible foam applications. This polyol is a low viscosity liquid with estimated functionality of 3 and equivalent weight in a range of 479-524. Agrol 3.6 polyol as a reference NOP was introduced up to 40% based on total polyols as a drop-in replacement for Poly-G 85-29 in the model high resilient foam formulation without any adjustment in the formulation.

As for the foams generated from mixtures of PMTAG Polyol and polyether polyol, the foaming experiments were carried out using a model formulation targeting high resilient flexible foams. This formulation is based on Poly-G 85-29 ethylene oxide tipped polyether triol (polyether polyol) and Mondur MRS-2 as an isocyanate, which is a 2,4'-MDI rich isocyanate. Blends of PMTAG Polyol and Poly-G 85-29 in a 5/95, 10/90, 20/80, 25/75 and 30/70 blends of PMTAG Polyol to Poly-G 85-29 were produced.

Materials:

A list of raw materials used in this evaluation is shown in Table A.

TABLE A

| Materials | | |
|---|---|---|
| Designation | Type | Supplier |
| POLYOLS | | |
| Poly-G 85-29 | Ethylene oxide caped polyether polyol Hydroxyl Value = 26.2; Eq. wt. = 2141.22 | Arch |
| PMTAG Polyol | Hydroxyl Value = 188.25; Eq. wt. = 298.01 Acidity Value = 2.47; Water content = 0.13% | Applicants |
| Agrol 3.6 | Soy based polyol; OH # 118 mg KOH/g; Acid # 0.52 mg KOH/g; Water Content = 0.036% | BioBased Technologies |

TABLE A-continued

Materials

| Designation | Type | Supplier |
|---|---|---|
| Lumulse POE 26 | Ethoxylated glycerol; Eq. Wt. = 416.2 | Lambent |
| SURFACTANTS | | |
| Tegostab B 4690 | Polyether/Silicone Oil Mix Eq. Wt. = 1335.7 | Evonik |
| CHAIN EXTENDERS/ CROSSLINKERS | | |
| Diethanolamine | 99% Diethanol amine; Eq. Wt. = 35.04 | Aldrich |
| CATALYSTS | | |
| Dabco 33LV | 33% Triethylene diamine in dipropylene glycol | Air Products |
| Niax A1 | bis(2-dimethylaminoethyl) ether | Momentive |
| Dabco T12 | Dibutyltin dilaurate | Air Products |
| ISOCYANATES | | |
| Mondur MRS-2 | 2,4'-rich diphenylmethane diisocyanate (F = 2.2; Eq. wt. = 128.83) | Bayer |

Properties of the PMTAG polyol were measured according to the test methods below.

| Property | Test method |
|---|---|
| Acid Value, mg KOH/g | ASTM D 4662-08 |
| Hydroxyl Value, mg KOH/g | ASTM D 4274-05 |
| Moisture, % | ASTM D 4672-00 |
| Viscosity (Brookfield Viscometer), cps | ASTM D 4878-08 |

Compatibility of PMTAG Polyols

Blends of PMTAG Polyols with Poly-G 85-29 polyether polyol used in the model, high-resilient foam formulations were prepared using the following procedure. The polyether polyol and PMTAG Polyol preheated at 70° C. were weighed into a Speed Mixer cup and then mixed for 60 seconds at 2200 rpm using Speed Mixer (FlackTek Inc.). Immediately after mixing, polyol mixtures were transferred into vials. One set of vials was kept at room temperature and the second set at 70° C. Consistency and compatibility of blends with different ratios of PMTAG Polyol and petroleum based polyol at room temperature and 70° C. were observed after 7 days and after two weeks. Results of this evaluation are shown in Table B below. Compatibility was evaluated at 5/95, 10/90, 20/80, and 30/70 PMTAG polyol and Poly-G 85-20 weight ratios.

TABLE B

Compatibility of PMTAG Polyol in Blends with Poly G 85-29

| Designation | Observation after 7 days | | Observation after 2 weeks | |
|---|---|---|---|---|
| | Compatible @ RT | Compatible @ 70° C. | Compatible @ RT | Compatible 70° C. |
| 5 pbw MTAG | Y | Y | Y | Y |
| 10 pbw MTAG | Y | Y | Y | Y |
| 20 pbw MTAG | Solid* | Y | Solid* | Y |
| 30 pbw MTAG | Solid* | Y | Solid* | Y |

*Blends were solid after storage for one day at room temperature

Preparation and Testing of Foams

The foaming experiments were carried out using a model formulation targeting high resilient flexible foams. This formulation is based on Poly-G 85-29 ethylene oxide tipped polyether triol (polyol). Lumulse POE 26 (ethoxylated glycerol) was used as a reactive cell opener. Diethanol amine was used as a co-catalyst and cross-linker. PMTAG Polyol was evaluated as drop-in replacements for Poly-G 85-29 polyol up to 25% levels, respectively. All foams were prepared at 90 Isocyanate Index with Mondur MRS-2 as an isocyanate, which is a 2,4'-MDI rich isocyanate. The representative data is shown in Tables C, D, E, and F below.

Agrol 3.6 polyol was used as a reference NOP, and was introduced up to 40% based on total polyols as a drop-in replacement for Poly-G 85-29 in the model HR foam formulation without any adjustment in the formulation. The representative data is shown in Tables G and H below.

Dabco 33LV and Niax A-1 were catalysts used in the foam formulations. Dabco 33LV catalyst promotes both gelling reaction (reaction of isocyanate with polyol) and blowing reaction (reaction of isocyanate with water).

These foams were prepared using a high-torque mixer (CRAFSTMAN 10-Inch Drill Press, Model No. 137.219000) at 3,100 rpm speed. In all foaming experiments, polyol components and isocyanate components of the foam systems were mixed for 7 seconds. Afterwards, the mixtures were transferred into open plastic container covered with 0.55-mil polyethylene liner and allowed to free-rise.

Polyol component of the model polyurethane system based on Poly-G 85-39 as a sole polyol and polyol components of the reference polyurethane foams based on Agrol 3.6 polyol were prepared using polyols conditioned at room temperature.

Foaming profiles, including cream time, gel time, and rise time were measured on all free-rise foams. After the rise time, the free-rise foams were immediately placed for 30 minutes in an air-circulating oven preheated at 80° C. to complete the cure.

The following foam properties in the Tables below were measured on the free-rise foams according to ASTM D 3574-08:

Foam Density,

Resilience via Ball Rebound,

Tensile Strength at Break,

Elongation at Break,

Tear Strength,

CFD, Compression Force Deflection,

Hysteresis,

All free-rise foams were aged under room conditions for a minimum one week before the testing.

TABLE C

Screening of Free-Rise Flexible Foams Based on PMTAG Polyol

| Designation | Eq. Wt. | 1 | 2 | 3 | 4 | 5 | 6 |
|---|---|---|---|---|---|---|---|
| Sample designation | | REF | TAG-5 | TAG-10 | TAG-15 | TAG-20 | TAG-25 |
| PMTAG Polyol based on total polyols, % | | 0 | 5 | 10 | 15 | 20 | 25 |
| PMTAG Polyol based on total weight | | 0 | 2.94 | 5.82 | 8.65 | 11.43 | 14.15 |
| Polyol component of PU system, pbw | | | | | | | |
| Poly-G 85-29 | 2141.22 | 97 | 92.15 | 87.3 | 82.45 | 77.6 | 72.75 |
| PMTAG | 298.01 | — | 4.85 | 9.7 | 14.55 | 19.4 | 24.25 |
| Water | 9 | 3.6 | 3.6 | 3.6 | 3.6 | 3.6 | 3.6 |
| Lumulse POE 26 | 416.2 | 3 | 3 | 3 | 3 | 3 | 3 |
| Tegostab B 4690 | 1335.7 | 1 | 1 | 1 | 1 | 1 | 1 |
| Dabco 33LV | 105 | 0.8 | 0.8 | 0.8 | 0.8 | 0.8 | 0.8 |
| Diethanolamine | 35.04 | 1 | 1 | 1 | 1 | 1 | 1 |
| Niax A-1 | 233.7 | 0.1 | 0.1 | 0.1 | 0.1 | 0.1 | 0.1 |
| Dabco T12 | — | — | — | — | — | — | — |
| Isocyanate component of PU System, pbw | | | | | | | |
| Mondur MRS-2 | 128.83 | 56.80 | 58.42 | 60.05 | 61.67 | 63.30 | 64.92 |
| Isocyanate Index | | 90 | 90 | 90 | 90 | 90 | 90 |
| Reaction Profile | | | | | | | |
| Total amount of polyols used in foaming experiments, g | | 100 | 200 | 100 | 100 | 100 | 100 |
| Mix time, sec. | | 7 | 7 | 7 | 7 | 7 | 7 |
| Cream time, sec. | | 11 | 11 | 10 | 10 | 12 | 11 | 12 |
| Gel time, sec. | | 27 | 30 | 24 | 25 | 28 | 24 | 24 |
| Rise time, sec. | | 74 | 78 | 77 | 85 | 75 | 85 | 75 |
| Post-curing time & temperature | | 30 min. @ 80° C. | | | | | |
| Apparent cell structure | | Uniform | Uniform | Uniform | Uniform | Uniform | Coarse |

TABLE D

Screening of Free-Rise Flexible Foams Based on PMTAG Polyol

| Designation | Eq. Wt. | 1 | 2 | 3 | 4 | 5 |
|---|---|---|---|---|---|---|
| Sample designation | | REF | TAG-25 | TAG-25-T12 | TAG-30 | TAG-30-T12 |
| PMTAG Polyol based on total polyols, % | | 0 | 25 | 25 | 30 | 30 |
| PMTAG Polyol based on total weight | | 0 | 14.15 | 14.14 | 16.82 | 16.81 |
| Polyol component of PU system, pbw | | | | | | |
| Poly-G 85-29 | 2141.22 | 97 | 72.75 | 72.75 | 67.9 | 67.9 |
| PMTAG | 298.01 | — | 24.25 | 24.25 | 29.1 | 29.1 |
| Water | 9 | 3.6 | 3.6 | 3.6 | 3.6 | 3.6 |
| Lumulse POE 26 | 416.2 | 3 | 3 | 3 | 3 | 3 |
| Tegostab B 4690 | 1335.7 | 1 | 1 | 1 | 1 | 1 |
| Dabco 33LV | 105 | 0.8 | 0.8 | 0.8 | 0.8 | 0.8 |
| Diethanolamine | 35.04 | 1 | 1 | 1 | 1 | 1 |
| Niax A-1 | 233.7 | 0.1 | 0.1 | 0.1 | 0.1 | 0.1 |
| Dabco T12 | — | — | — | 0.1 | — | 0.1 |
| Isocyanate component of PU System, pbw | | | | | | |
| Mondur MRS-2 | 128.83 | 56.80 | 64.92 | 64.92 | 66.54 | 66.54 |
| Isocyanate Index | | 90 | 90 | 90 | 90 | 90 |
| Reaction Profile | | | | | | |
| Total amount of polyols used in foaming experiments, g | | 100 | 200 | 100 | 100 | 100 |
| Mix time, sec. | | 7 | 7 | 7 | 7 | 7 |
| Cream time, sec. | | 11 | 11 | 12 | 11 | 13 | 10 |
| Gel time, sec. | | 27 | 30 | 24 | 22 | 30 | 21 |
| Rise time, sec. | | 74 | 78 | 75 | 50 | — | 48 |

TABLE D-continued

Screening of Free-Rise Flexible Foams Based on PMTAG Polyol

| Designation | Eq. Wt. | 1 | 2 | 3 | 4 | 5 |
|---|---|---|---|---|---|---|
| Post-curing time & temperature | | | | 30 min. @ 80° C. | | |
| Apparent cell structure | | Uniform | Coarse | Uniform | Spilled over @ 45 sec. | Coarse |

TABLE E

Formulations and Properties of Free-Rise Flexible Foams with Uniform Cell Structure Based on PMTAG Polyol

| Designation | Eq. Wt. | 1 | 2 | 3 | 4 | 5 | 6 |
|---|---|---|---|---|---|---|---|
| Sample designation | | REF | TAG-5 | TAG-10 | TAG-15 | TAG-20 | TAG-25-T12 |
| PMTAG Polyol based on total polyols, % | | 0 | 5 | 10 | 15 | 20 | 25 |
| PMTAG Polyol based on total weight | | 0 | 2.94 | 5.82 | 8.65 | 11.43 | 14.14 |
| Polyol component of PU system, pbw | | | | | | | |
| Poly-G 85-29 | 2141.22 | 97 | 92.15 | 87.3 | 82.45 | 77.6 | 72.75 |
| PMTAG | 298.01 | — | 4.85 | 9.7 | 14.55 | 19.4 | 24.25 |
| Water | 9 | 3.6 | 3.6 | 3.6 | 3.6 | 3.6 | 3.6 |
| Lumulse POE 26 | 416.2 | 3 | 3 | 3 | 3 | 3 | 3 |
| Tegostab B 4690 | 1335.7 | 1 | 1 | 1 | 1 | 1 | 1 |
| Dabco 33LV | 105 | 0.8 | 0.8 | 0.8 | 0.8 | 0.8 | 0.8 |
| Diethanolamine | 35.04 | 1 | 1 | 1 | 1 | 1 | 1 |
| Niax A-1 | 233.7 | 0.1 | 0.1 | 0.1 | 0.1 | 0.1 | 0.1 |
| Dabco T12 | — | — | — | — | — | — | 0.1 |
| Isocyanate component of PU System, pbw | | | | | | | |
| Mondur MRS-2 | 128.83 | 56.80 | 58.42 | 60.05 | 61.67 | 63.30 | 64.92 |
| Isocyanate Index | | 90 | 90 | 90 | 90 | 90 | 90 |
| Reaction Profile | | | | | | | |
| Total amount of polyols used in foaming experiments, g | | 100   200 | 100   200 | 100   200 | 100   200 | 100   200 | 100   200 |
| Mix time, sec. | | 7   7 | 7   7 | 7   7 | 7   7 | 7   7 | 7   7 |
| Cream time, sec. | | 11   11 | 10   12 | 10   11 | 12   13 | 11   14 | 11   11 |
| Gel time, sec. | | 27   30 | 24   26 | 25   27 | 28   29 | 24   31 | 22   23 |
| Rise time, sec. | | 74   78 | 77   78 | 85   89 | 75   77 | 85   91 | 50   54 |
| Post-curing time & temperature | | | | 30 min. @ 80° C. | | | |
| Properties* | | | | | | | |
| Free-rise density, pcf | | 2.40 ± 0.13 | 2.10 ± 0.03 | 2.18 ± 0.09 | 2.39 ± 0.23 | 2.17 ± 0.08 | 1.98 ± 0.01 |
| Apparent cell structure | | Uniform | Uniform | Uniform | Uniform | Uniform | Uniform |

*Testing was carried out on foams prepared with 200 g of polyols in the formulation.

TABLE F

Formulations and Properties of Free-Rise Flexible Foams with Uniform Cell Structure Based on PMTAG Polyol

| Designation | Eq. Wt. | 1 | 2 | 3 | 4 | 5 | 6 |
|---|---|---|---|---|---|---|---|
| Sample designation | | REF | TAG-5 | TAG-10 | TAG-15 | TAG-20 | TAG-25-T12 |
| PMTAG Polyol based on total polyols, % | | 0 | 5 | 10 | 15 | 20 | 25 |

TABLE F-continued

Formulations and Properties of Free-Rise Flexible Foams with Uniform Cell Structure Based on PMTAG Polyol

| Designation | Eq. Wt. | 1 | 2 | 3 | 4 | 5 | 6 |
|---|---|---|---|---|---|---|---|
| PMTAG Polyol based on total weight | | 0 | 2.94 | 5.82 | 8.65 | 11.43 | 14.14 |
| Properties | | | | | | | |
| Free-rise density, pcf | | 2.40 ± 0.13 | 2.10 ± 0.03 | 2.18 ± 0.09 | 2.39 ± 0.23 | 2.17 ± 0.08 | 1.98 ± 0.01 |
| Resilience, Ball (16 mm) Rebound, % | | 62.5 ± 1.4 | 53.4 ± 1.8 | 49.8 ± 1.4 | 44.2 ± 1.4 | 40.1 ± 1.1 | 34.0 ± 1.4 |
| CFD @ 25% | | 0.29 ± 0.1 | 0.18 ± 0.01 | 0.27 ± 0.05 | 0.35 ± 0.04 | 0.41 ± 0.03 | 0.62 ± 0.07 |
| CFD @ 50% | | 0.53 ± 0.3 | 0.36 ± 0.01 | 0.59 ± 0.06 | 0.69 ± 0.05 | 0.77 ± 0.06 | 1.00 ± 0.06 |
| CFD @ 65% | | 1.03 ± 0.13 | 0.75 ± 0.04 | 1.10 ± 0.07 | 1.20 ± 0.10 | 1.34 ± 0.13 | 1.66 ± 0.05 |
| Support Facto #1, 50% CFD/25% CFD | | 1.83 | 2.00 | 2.19 | 1.97 | 1.88 | 1.61 |
| Support Facto #2, 65% CFD/25% CFD | | 3.55 | 4.17 | 4.07 | 3.43 | 3.27 | 2.68 |
| Tensile Strength, psi | | 16.7 ± 2.1 | 16.7 ± 0.9 | 20.2 ± 2.1 | 18.6 ± 1.3 | 16.4 ± 1.2 | 22.6 ± 1.3 |
| Elongation at Break, % | | 106 ± 4 | 103 ± 5 | 108 ± 3 | 101 ± 6 | 92 ± 2 | 70 ± 4 |
| Tear Strength, lbf/in, die C | | 2.8 ± 0.2 | 3.0 ± 0.1 | 3.3 ± 0.1 | 3.5 ± 0.1 | 3.4 ± 0.1 | 4.4 ± 0.1 |
| Hysteresis, % | | 52.7 ± 1.1 | 59.7 ± 1.3 | 63.9 ± 1.6 | 66.6 ± 2.0 | 68.9 ± 2.0 | 81.3 ± 2.3 |
| Properties Normalized to Density of 2.40 pcf | | | | | | | |
| CFD @ 25% | | 0.29 | 0.21 | 0.30 | 0.35 | 0.45 | 0.75 |
| CFD @ 50% | | 0.53 | 0.41 | 0.65 | 0.69 | 0.85 | 1.21 |
| CFD @ 65% | | 1.03 | 0.86 | 1.21 | 1.21 | 1.48 | 2.01 |
| Tensile Strength, psi | | 16.70 | 19.09 | 22.24 | 18.68 | 18.14 | 27.39 |
| Tear Strength, lbf/in | | 2.8 | 3.43 | 3.63 | 3.51 | 3.76 | 5.33 |
| Apparent cell structure | | Uniform | Uniform | Uniform | Uniform | Uniform | Uniform |

* Testing was carried out on foams prepared with 200 g of polyols in the formulation.

TABLE G

Formulations and Properties of Free-Rise Flexible Foams Based on Agrol 3.6

| Designation | Eq. Wt. | 1 | 2 | 3 | 4 | 5 | 6 | 7 |
|---|---|---|---|---|---|---|---|---|
| Sample designation | | REF | Ag-5 | Ag-10 | Ag-15 | Ag-20 | Ag-30 | Ag-40 |
| Agrol 3.6 Polyol based on total polyols, % | | 0 | 5 | 10 | 15 | 20 | 30 | 40 |
| Agrol 3.6 Polyol based on total weight Polyol component of PU system, pbw | | 0 | 2.95 | 5.87 | 8.76 | 11.62 | 17.24 | 22.74 |
| Poly-G 85-29 | 2141.22 | 97 | 92.15 | 87.3 | 82.45 | 77.6 | 67.9 | 58.2 |
| Agrol 3.6 | 475.42 | — | 4.85 | 9.7 | 14.55 | 19.4 | 29.1 | 38.8 |
| Water | 9 | 3.6 | 3.6 | 3.6 | 3.6 | 3.6 | 3.6 | 3.6 |
| Lumulse POE 26 | 416.2 | 3 | 3 | 3 | 3 | 3 | 3 | 3 |
| Tegostab B 4690 | 1335.7 | 1 | 1 | 1 | 1 | 1 | 1 | 1 |
| Dabco 33LV | 105 | 0.8 | 0.8 | 0.8 | 0.8 | 0.8 | 0.8 | 0.8 |
| Diethanol-amine | 35.04 | 1 | 1 | 1 | 1 | 1 | 1 | 1 |
| Niax A-1 | 233.7 | 0.1 | 0.1 | 0.1 | 0.1 | 0.1 | 0.1 | 0.1 |

TABLE G-continued

Formulations and Properties of Free-Rise Flexible Foams Based on Agrol 3.6

| Designation | Eq. Wt. | 1 | 2 | 3 | 4 | 5 | 6 | 7 |
|---|---|---|---|---|---|---|---|---|
| Isocyanate component of PU System, pbw | | | | | | | | |
| Mondur MRS-2 | 128.83 | 56.80 | 57.72 | 58.64 | 59.56 | 60.48 | 62.32 | 64.16 |
| Isocyanate Index | | 90 | 90 | 90 | 90 | 90 | 90 | 90 |
| Reaction Profile | | | | | | | | |
| Total amount of polyols used in foaming experiments, g | | 100  200 | 100  200 | 100  200 | 100  200 | 100  200 | 100  200 | 100  200 |
| Mix time, sec. | | 7  7 | 7  7 | 7  7 | 7  7 | 7  7 | 7  7 | 7  7 |
| Cream time, sec. | | 11  11 | 10  11 | 11  13 | 12  13 | 13  14 | 14  16 | 17 |
| Gel time, sec. | | 27  30 | 26  27 | 28  30 | 29  30 | 30  32 | 37  36 | 42 |
| Rise time, sec. | | 74  78 | 62  66 | 64  74 | 69  77 | 73  82 | 90  85 | 90 |
| Post-curing time & temperature | | | | 30 min. @ 80° C. | | | | |
| Properties* | | | | | | | | |
| Free-rise density, pcf | | 2.40 ± 0.13 | 2.42 ± 0.16 | 2.39 ± 0.10 | 2.21 ± 0.07 | 2.42 ± 0.16 | 2.55 ± 0.12 | 2.86 ± 0.24 |
| Apparent cell structure | | Uniform | Uniform | Uniform | Uniform | Uniform | Uniform | Uniform |

*Testing was carried out on foams prepared with 200 g of polyols in the formulation.

TABLE H

Formulations and Properties of Free-Rise Flexible Foams Based on Agrol 3.6

| Designation | Eq. Wt. | 1 | 2 | 3 | 4 | 5 | 6 | 7 |
|---|---|---|---|---|---|---|---|---|
| Sample designation | | REF | Ag-5 | Ag-10 | Ag-15 | Ag-20 | Ag-30 | Ag-40 |
| Agrol 3.6 Polyol based on total polyols, % | | 0 | 5 | 10 | 15 | 20 | 30 | 40 |
| Agrol 3.6 Polyol based on total weight, | | 0 | 2.95 | 5.87 | 8.76 | 11.62 | 17.24 | 22.74 |
| Properties* | | | | | | | | |
| Free-rise density, pcf | | 2.40 ± 0.13 | 2.42 ± 0.16 | 2.39 ± 0.10 | 2.21 ± 0.07 | 2.42 ± 0.16 | 2.55 ± 0.12 | 2.86 ± 0.24 |
| Resilience, Ball (16 mm) Rebound, % | | 62.5 ± 1.4 | 54.4 ± 1.4 | 52.3 ± 1.4 | 49.8 ± 1.4 | 44.2 ± 1.4 | 41.2 ± 1.1 | 35.1 ± 1.1 |
| CFD @ 25% | | 0.29 ± 0.1 | 0.28 ± 0.03 | 0.26 ± 0.03 | 0.27 ± 0.06 | 0.22 ± 0.05 | 0.32 ± 0.01 | 0.35 ± 0.03 |
| CFD @ 50% | | 0.53 ± 0.3 | 0.56 ± 0.06 | 0.46 ± 0.04 | 0.51 ± 0.09 | 0.43 ± 0.05 | 0.61 ± 0.03 | 0.73 ± 0.07 |
| CFD @ 65% | | 1.03 ± 0.13 | 1.09 ± 0.10 | 0.85 ± 0.09 | 1.00 ± 0.14 | 0.84 ± 0.07 | 1.17 ± 0.08 | 1.33 ± 0.11 |
| Support Facto #1, 50% CFD/25% CFD | | 1.83 | 2.00 | 1.77 | 1.89 | 1.95 | 1.91 | 2.09 |
| Support Facto #2, 65% CFD/25% CFD | | 3.55 | 3.89 | 3.27 | 3.70 | 3.82 | 3.66 | 3.80 |
| Tensile Strength, psi | | 16.7 ± 2.1 | 21.3 ± 1.8 | 18.6 ± 1.9 | 16.4 ± 1.0 | 18.9 ± 2.3 | 19.0 ± 2.2 | 14.6 ± 1.9 |
| Elongation at Break, % | | 106 ± 4 | 110 ± 5 | 105 ± 5 | 116 ± 3 | 105 ± 5 | 95 ± 4 | 78 ± 5 |
| Tear Strength, lbf/in, die C | | 2.8 ± 0.2 | 3.6 ± 0.2 | 2.5 ± 0.1 | 2.7 ± 0.1 | 3.2 ± 0.1 | 3.4 ± 0.1 | 2.8 ± 0.2 |
| Hysteresis, % | | 52.7 ± 1.1 | 60.6 ± 3.7 | 62.9 ± 3.7 | 59.5 ± 3.6 | 68.9 ± 1.1 | 76.3 ± 3.7 | 85.2 ± 3.8 |
| Properties Normalized to Density of 2.40 pcf | | | | | | | | |
| CFD @ 25% | | 0.29 | 0.28 | 0.26 | 0.29 | 0.22 | 0.30 | 0.29 |
| CFD @ 50% | | 0.53 | 0.56 | 0.46 | 0.55 | 0.43 | 0.57 | 0.61 |
| CFD @ 65% | | 1.03 | 1.08 | 0.85 | 1.09 | 0.83 | 1.10 | 1.12 |

TABLE H-continued

Formulations and Properties of Free-Rise Flexible Foams Based on Agrol 3.6

| Designation | Eq. Wt. | 1 | 2 | 3 | 4 | 5 | 6 | 7 |
|---|---|---|---|---|---|---|---|---|
| Tensile Strength, psi | | 16.7 | 21.12 | 18.68 | 17.81 | 18.74 | 17.88 | 12.25 |
| Tear Strength, lbf/in | | 2.8 | 3.57 | 2.51 | 2.93 | 3.17 | 3.2 | 2.35 |
| Apparent cell structure | | Uniform | Uniform | Uniform | Uniform | Uniform | Uniform | Uniform |

*Testing was carried out on foams prepared with 200 g of polyols in the formulation.

Foaming Performance of PMTAG Polyols

Agrol 3.6 polyol as a reference NOP was introduced up to 40% based on total polyols as a drop-in replacement for Poly-G 85-29 in the model HR foam formulation without any adjustment in the formulation, as shown in Tables G and H above. The reactivity of the foaming system slightly decreased with introduction of Agrol 3.6 polyol. The foam density did not change significantly with addition of up to 20% Agrol 3.6. The density of foams prepared with higher levels of Agrol 3.6 was somewhat higher in comparison to the reference foams prepared without Agrol 3.6 polyol which might be ascribed to somewhat lower reactivity of the foaming system. In order to minimize the effect of density, properties that are directly dependent on foam density, such as CFD, tensile and tear strength were normalized to density of the reference foam of 2.40 pcf (Table H).

In the case of PMTAG polyol, foams with uniform cell structure were obtained without any adjustment in the catalyst package with up to 20% PMTAG polyol based on total polyols (Tables C and D)

Foams with uniform cell structures were obtained with 25% PMTAG polyol after addition of a small amount (0.1 pbw per 100 pbw of total polyols) of Dabco T-12 catalyst to the catalyst package (Tables C and D). Dabco T-12 is very efficient gelling catalyst (catalyst for reaction of isocyanate with polyol hydroxyl groups).

Formulations and properties of foams with uniform cell structure based on PMTAG polyol are summarized in Table E and F.

Foam Properties

Properties of reference foams based on Agrol 3.6 and foams based on PMTAG polyol are summarized in the aforementioned Tables. As expected, resilience decreased and hysteresis increased with introduction of NOPs, regardless on the type of NOP.

The CFD values were not significantly affected with introduction of Agrol 3.6 polyol as a drop-in replacement for Poly-G 85-29 polyol. However, CFD values increased significantly with introduction of PMTAG polyol.

Support factor (comfort factor) as a measure of load bearing properties of foams was calculated as a ratio of CFD at 65% deflection and CFD at 25% deflection and as a ratio of CFD at 50% deflection and CFD at 25% deflection, respectively. Support factors were not significantly affected with introduction of NOPs. In all foams, with exception of foams prepared with 25% PMTAG polyol, the 65% CFD/ 25% CFD support factor was higher than 3. In most applications of flexible foams, the support factor higher than 2 is required.

The tensile strength and tear resistance of foams increased with introduction of PMTAG polyols. The tensile strength and tear resistance of foams based on PMTAG polyol was higher in comparison to foams based on the same amounts of Agrol 3.6 polyol and foams based on the same amounts of PMTAG polyol.

Elongation at break in all foams prepared with up to 20% NOPs was close to 100% or higher, which is a characteristic of most flexible foams. The elongation at break of the reference foam prepared using a model foam formulation without any NOP was 104%.

Mixtures of Polyol 1314 with Polyether Polyol in Flexible Foam Applications

Another palm oil based polyol was also synthesized in addition to those previously disclosed herein. This polyol, made without solvent and referred to as Polyol 1314, was synthesized as follows: The hydroxylation process was carried in a 2 L jacketed reactor. The reactor was checked so that it was clear, and purged with N2 for 20 min. Meanwhile, the palm oil MTAG was melted in a microwave and the temperature of the jacketed reactor was set at 60° C. Once the desired temperature was achieved, 551 g the melted palm oil MTAG was charged into the reactor, and 410 ml of 98% formic acid was also added to the reactor. The acidified reaction mixture was stirred for 30 minutes to until it was homogeneous. 610 ml of 30% hydrogen peroxide was added dropwise to the stirring mixture. The addition was for 3 hours. After the addition, the reaction was continued at 60-65° C. for 27 hours. After the 27 hours, about 2500 ml of a saturated solution of $NaHCO_3$ was added to the reaction and stirred for 20 minutes. After this, the stirring was stopped and the layers were allowed to separate, and the lower layer (aqueous) layer was discarded. This was repeated five times. The oily layer was then washed with 250 ml of sodium thiosulfate and cleaned with a brine solution. The brine wash was carried out until the pH of the aqueous solution was 7. The remaining oily layer was drained off, dried under a vacuum and weighted. 546 g of oil was obtained.

The performance of Polyol 1314 in comparison to a commercial Natural Oil Based Polyol (NOP) as drop-in replacements for a conventional polyether polyol in a model high resilient (HR) flexible polyurethane foam formulation was studied.

Agrol 3.6 polyol from BioBased Technologies was selected as a reference NOP in the comparative study. Agrol 3.6 polyol is well established commercial soy-based polyol suitable for flexible foam applications. This polyol is a low viscosity liquid with estimated functionality of 3 and equivalent weight in a range of 479-524. Agrol 3.6 polyol as a reference NOP was introduced up to 40% based on total polyols as a drop-in replacement for Poly-G 85-29 in the model high resilient foam formulation without any adjustment in the formulation.

As for the foams generated from mixtures of Polyol 1314 and commercial polyol, the foaming experiments were carried out using a model formulation targeting high resilient flexible foams. This formulation is based on Poly-G 85-29 ethylene oxide tipped polyether triol (polyol) and Mondur MRS-2 as an isocyanate, which is a 2,4'-MDI rich isocyanate. Blends of Polyol 1314 and Poly-G 85-29 in a 5/95, 10/90, 20/80, 25/75 and 30/70 blends of Polyol 1314 to Poly-G 85-29 were produced.

Materials:

A list of raw materials used in this evaluation is shown in Table I.

TABLE I

Materials

| Designation | Type | Supplier |
|---|---|---|
| POLYOLS | | |
| Poly-G 85-29 | Ethylene oxide caped polyether polyol Hydroxyl Value = 26.2; Eq. wt. = 2141.22 | Arch |
| Polyol 1314 | Bio-based polyol (no solvent used) Hydroxyl Value = 164.87; Eq. wt. = 340.27 Acidity Value = 0.88; Water content = 0.04% | Applicants |
| Agrol 3.6 | Soy based polyol; OH # 118 mg KOH/g; Acid # 0.52 mg KOH/g; Water Content = 0.036% | BioBased Technologies |
| Lumulse POE 26 | Ethoxylated glycerol; Eq. Wt = 416.2 | Lambent |
| SURFACTANTS | | |
| Tegostab B 4690 | Polyether/Silicone Oil Mix Eq. Wt. = 1335.7 | Evonik |
| CHAIN EXTENDERS/ CROSSLINKERS | | |
| Diethanolamine | 99% Diethanol amine; Eq. Wt. = 35.04 | Aldrich |
| CATALYSTS | | |
| Dabco 33LV | 33% Triethylene diamine in dipropylene glycol | Air Products |
| Niax A1 | bis(2-dimethylaminoethyl) ether | Momentive |
| Dabco T12 | Dibutyltin dilaurate | Air Products |
| ISOCYANATES | | |
| Mondur MRS-2 | 2,4'-rich diphenylmethane diisocyanate (F = 2.2; Eq. wt. = 128.83) | Bayer |

Properties of the Polyol 1314 were measured according to the test methods below.

| Property | Test method |
|---|---|
| Acid Value, mg KOH/g | ASTM D 4662-08 |
| Hydroxyl Value, mg KOH/g | ASTM D 4274-05 |
| Moisture, % | ASTM D 4672-00 |
| Viscosity (Brookfield Viscometer), cps | ASTM D 4878-08 |

Compatibility of Polyol 1314

Blends of Polyol 1314 with Poly-G 85-29 polyether polyol used in the model, high-resilient foam formulations were prepared using the following procedure. The polyether polyol and Polyol 1314 preheated at 70° C. were weighed into a Speed Mixer cup and then mixed for 60 seconds at 2200 rpm using Speed Mixer (FlackTek Inc.). Immediately after mixing, polyol mixtures were transferred into vials. One set of vials was kept at room temperature and the second set at 70° C. Consistency and compatibility of blends with different ratios of Polyol 1314 and petroleum based polyol at room temperature and 70° C. were observed after 7 days and after two weeks. Results of this evaluation are shown in Table J below. Compatibility was evaluated at 5/95, 10/90, 20/80, and 30/70 Polyol 1314 and Poly-G 85-20 weight ratios.

TABLE J

Compatibility of Polyol 1314 in Blends with Poly G 85-29

| | Observation after 7 days | | Observation after 2 weeks | |
|---|---|---|---|---|
| Designation | Compatible @ RT | Compatible @ 70° C. | Compatible @ RT | Compatible 70° C. |
| 5 pbw 1314 | Y | Y | Y | Y |
| 10 pbw 1314 | Y | Y | Y | Y |
| 20 pbw 1314 | Y | Y | Y | Y |
| 30 pbw 1314 | Solid* | Y | Solid* | Y |

*Blends were solid after storage for one day at room temperature

Preparation and Testing of Foams

The foaming experiments were carried out using a model formulation targeting high resilient flexible foams. This formulation is based on Poly-G 85-29 ethylene oxide tipped polyether triol (polyol). Lumulse POE 26 (ethoxylated glycerol) was used as a reactive cell opener. Diethanol amine was used as a co-catalyst and cross-linker.

Polyol 1314 was evaluated as drop-in replacements for Poly-G 85-29 polyol up to 25% levels, respectively. All foams were prepared at 90 Isocyanate Index with Mondur MRS-2 as an isocyanate, which is a 2,4'-MDI rich isocyanate. The representative data is shown in Tables K, L, M, and N below.

Agrol 3.6 polyol was used as a reference NOP, and was introduced up to 40% based on total polyols as a drop-in replacement for Poly-G 85-29 in the model HR foam formulation without any adjustment in the formulation. The representative data is shown in Tables G and H above.

Dabco 33LV and Niax A-1 were catalysts used in the foam formulations. Dabco 33LV catalyst promotes both gelling reaction (reaction of isocyanate with polyol) and blowing reaction (reaction of isocyanate with water).

These foams were prepared using a high-torque mixer (CRAFSTMAN 10-Inch Drill Press, Model No. 137.219000) at 3,100 rpm speed. In all foaming experiments, polyol components and isocyanate components of the foam systems were mixed for 7 seconds. Afterwards, the mixtures were transferred into open plastic container covered with 0.55-mil polyethylene liner and allowed to free-rise.

Polyol component of the model polyurethane system based on Poly-G 85-39 as a sole polyol and polyol components of the reference polyurethane foams based on Agrol 3.6 polyol were prepared using polyols conditioned at room temperature.

Foaming profiles, including cream time, gel time, and rise time were measured on all free-rise foams. After the rise time, the free-rise foams were immediately placed for 30 minutes in an air-circulating oven preheated at 80° C. to complete the cure.

The following foam properties in the Tables below were measured on the free-rise foams according to ASTM D 3574-08:

Foam Density,
Resilience via Ball Rebound,
Tensile Strength at Break,
Elongation at Break,
Tear Strength,
CFD, Compression Force Deflection,
Hysteresis, All free-rise foams were aged under room conditions for a minimum one week before the testing.

TABLE K

Screening of Free-Rise Flexible Foams Based on Polyol 1314

| Designation | Eq. Wt. | 1 | 2 | 3 | 4 | 5 | 6 | 7 | 8 |
|---|---|---|---|---|---|---|---|---|---|
| Sample designation | | REF | ES-5 | ES-10 | ES-10-T12 | ES-10-T12-2 | ES-15-T12 | ES-15-T12-2 | ES-15-T12-3 |
| Polyol 1314 based on total polyols, % | | 0 | 5 | 10 | 10 | 10 | 15 | 15 | 15 |
| Polyol 1314 based on total weight, | | 0 | 2.94 | 5.84 | 5.84 | 5.84 | 8.69 | 8.71 | 8.90 |
| Polyol component of PU system, pbw | | | | | | | | | |
| Poly-G 85-29 | 2141.22 | 97 | 92.15 | 87.3 | 87.3 | 87.3 | 82.45 | 82.45 | 82.45 |
| Polyol 1314 | 340.27 | — | 4.85 | 9.7 | 9.7 | 9.7 | 14.55 | 14.55 | 14.55 |
| Water | 9 | 3.6 | 3.6 | 3.6 | 3.6 | 3.6 | 3.6 | 3.6 | 3.6 |
| Lumulse POE 26 | 416.2 | 3 | 3 | 3 | 3 | 3 | 3 | 3 | 3 |
| Tegostab B 4690 | 1335.7 | 1 | 1 | 1 | 1 | 1 | 1 | 1 | 1 |
| Dabco 33LV | 105 | 0.8 | 0.8 | 0.8 | 0.8 | 0.8 | 0.8 | 0.6 | 0.8 |
| Diethanolamine | 35.04 | 1 | 1 | 1 | 1 | 1 | 1 | 1 | 0 |
| Niax A-1 | 233.7 | 0.1 | 0.1 | 0.1 | 0.1 | 0 | 0 | 0 | 0 |
| Dabco T12 | — | — | — | — | 0.1 | 0.1 | 0.1 | 0.2 | 0.5 |
| Isocyanate component of PU System, pbw | | | | | | | | | |
| Mondur MRS-2 | 128.83 | 56.80 | 58.19 | 59.58 | 59.58 | 59.53 | 60.92 | 60.70 | 57.61 |
| Isocyanate Index | | 90 | 90 | 90 | 90 | 90 | 90 | 90 | 90 |
| Reaction Profile | | | | | | | | | |
| Total amount of polyols used in foaming experiments, g | | 100 | 200 | 100 | 100 | 100 | 100 | 100 | 100 |
| Mix time, sec. | | 7 | 7 | 7 | 7 | 5 | 7 | 7 | 7 | 7 |
| Cream time, sec. | | 11 | 11 | 10 | 9 | 6 | 9 | 9 | 11 | 10 |
| Gel time, sec. | | 27 | 30 | 25 | 23 | 15 | 23 | 22 | 23 | 20 |
| Rise time, sec. | | 74 | 78 | 63 | 62 | 40 | 56 | 54 | 61 | 43 |
| Post-curing time & temperature | | | | | | 30 min. @ 80° C. | | | | |
| Apparent cell structure | | Uniform | Uniform | Coarse | Coarse | Uniform | Coarse | Coarse | Uniform |

TABLE L

Screening of Free-Rise Flexible Foams Based on Polyol 1314

| Designation | Eq. Wt. | 1 | 2 | 3 |
|---|---|---|---|---|
| Sample designation | | REF | ES-20-T12-0.5 | ES-25-T12-0.5 |
| Polyol 1314 based on total polyols, % | | 0 | 20 | 25 |
| Polyol 1314 based on total weight, | | 0 | 11.76 | 14.58 |
| Polyol component of PU system, pbw | | | | |
| Poly-G 85-29 | 2141.22 | 97 | 77.6 | 72.75 |
| Polyol 1314 | 340.27 | — | 19.4 | 24.25 |
| Water | 9 | 3.6 | 3.6 | 3.6 |
| Lumulse POE 26 | 416.2 | 3 | 3 | 3 |
| Tegostab B 4690 | 1335.7 | 1 | 1 | 1 |
| Dabco 33LV | 105 | 0.8 | 0.8 | 0.8 |
| Diethanolamine | 35.04 | 1 | 0 | 0 |
| Niax A-1 | 233.7 | 0.1 | 0 | 0 |
| Dabco T12 | — | — | 0.5 | 0.5 |
| Isocyanate component of PU System, pbw | | | | |
| Mondur MRS-2 | 128.83 | 56.80 | 59.00 | 60.39 |
| Isocyanate Index | | 90 | 90 | 90 |
| Reaction Profile | | | | |
| Total amount of polyols used in foaming experiments, g | | 100 | 200 | 100 | 100 |
| Mix time, sec. | | 7 | 7 | 7 | 7 |
| Cream time, sec. | | 11 | 11 | 9 | 11 |
| Gel time, sec. | | 27 | 30 | 19 | 22 |
| Rise time, sec. | | 74 | 78 | 50 | 51 |
| Post-curing time & temp. | | | 30 min. @ 80° C. | | |
| Apparent cell structure | | Uniform | Uniform | Coarse |

TABLE M

Formulations and Properties of Free-Rise Flexible Foams with Uniform Cell Structure Based on Polyol 1314

| Designation | Eq. Wt. | 1 | 2 | 3 | 4 | 5 |
|---|---|---|---|---|---|---|
| Sample designation | | REF | ES-5 | ES-10-T12-2 | ES-15-T12-3 | ES-20-T12-0.5 |
| Polyol 1314 based on total polyols, % | | 0 | 5 | 10 | 15 | 20 |
| Polyol 1314 based on total weight | | 0 | 2.94 | 5.84 | 8.90 | 11.76 |
| Polyol component of PU system, pbw | | | | | | |
| Poly-G 85-29 | 2141.22 | 97 | 92.15 | 87.3 | 82.45 | 77.6 |
| Polyol 1314 | 340.27 | — | 4.85 | 9.7 | 14.55 | 19.4 |
| Water | 9 | 3.6 | 3.6 | 3.6 | 3.6 | 3.6 |
| Lumulse POE 26 | 416.2 | 3 | 3 | 3 | 3 | 3 |
| Tegostab B 4690 | 1335.7 | 1 | 1 | 1 | 1 | 1 |
| Dabco 33LV | 105 | 0.8 | 0.8 | 0.8 | 0.8 | 0.8 |
| Diethanolamine | 35.04 | 1 | 1 | 1 | 0 | 0 |
| Niax A-1 | 233.7 | 0.1 | 0.1 | 0 | 0 | 0 |
| Dabco T12 | — | — | — | 0.1 | 0.5 | 0.5 |
| Isocyanate component of PU System, pbw | | | | | | |
| Mondur MRS-2 | 128.83 | 56.80 | 58.19 | 59.53 | 57.61 | 59.00 |
| Isocyanate Index | | 90 | 90 | 90 | 90 | 90 |
| Reaction Profile | | | | | | |
| Total amount of polyols used in foaming experiments, g | | 100  200 | 100  200 | 100  200 | 100  200 | 100  200 |
| Mix time, sec. | | 7  7 | 7  7 | 7  7 | 7  7 | 7  7 |
| Cream time, sec. | | 11  11 | 9  12 | 9  12 | 10  11 | 9  10 |
| Gel time, sec. | | 27  30 | 23  27 | 23  25 | 20  21 | 19  20 |
| Rise time, sec. | | 74  78 | 56  65 | 56  57 | 43  44 | 50  54 |
| Post-curing time & temperature | | 30 min. @ 80° C. | | | | |
| Properties* | | | | | | |
| Free-rise density, pcf | | 2.40 ± 0.13 | 2.00 ± 0.11 | 1.88 ± 0.05 | 1.97 ± 0.08 | 2.19 ± 0.04 |
| Resilience, Ball (16 mm) Rebound, % | | 62.5 ± 1.4 | 60.0 ± 1.4 | 47.3 ± 1.4 | 42.2 ± 1.4 | 39.6 ± 1.4 |
| Apparent cell structure | | Uniform | Uniform | Uniform | Uniform | Uniform |

*Testing was carried out on foams prepared with 200 g of polyols in the formulation.

TABLE N

Formulations and Properties of Free-Rise Flexible Foams with Uniform Cell Structure Based on Polyol 1314

| Designation | Eq. Wt. | 1 | 2 | 3 | 4 | 5 |
|---|---|---|---|---|---|---|
| Sample designation | | REF | ES-5 | ES-10-T12-2 | ES-15-T12-3 | ES-20-T12-0.5 |
| Polyol 1314 based on total polyols, % | | 0 | 5 | 10 | 15 | 20 |
| Polyol 1314 based on total weight | | 0 | 2.94 | 5.84 | 8.90 | 11.76 |
| Properties* | | | | | | |
| Free-rise density, pcf | | 2.40 ± 0.13 | 2.00 ± 0.11 | 1.88 ± 0.05 | 1.97 ± 0.08 | 2.19 ± 0.04 |
| Resilience, Ball (16 mm) Rebound, % | | 62.5 ± 1.4 | 60.0 ± 1.4 | 47.3 ± 1.4 | 42.2 ± 1.4 | 39.6 ± 1.4 |
| CFD @ 25% | | 0.29 ± 0.1 | 0.18 ± 0.01 | 0.25 ± 0.02 | 0.38 ± 0.02 | 0.53 ± 0.06 |
| CFD @ 50% | | 0.53 ± 0.3 | 0.38 ± 0.03 | 0.46 ± 0.04 | 0.68 ± 0.04 | 0.97 ± 0.05 |
| CFD @ 65% | | 1.03 ± 0.13 | 0.73 ± 0.08 | 0.83 ± 0.08 | 1.21 ± 0.08 | 1.89 ± 0.08 |
| Support Facto #1, 50% CFD/25% CFD | | 1.83 | 2.11 | 1.84 | 1.79 | 1.83 |
| Support Facto #2, 65% CFD/25% CFD | | 3.55 | 4.06 | 3.32 | 3.18 | 3.57 |

TABLE N-continued

Formulations and Properties of Free-Rise Flexible Foams with Uniform Cell Structure Based on Polyol 1314

| Designation | Eq. Wt. | 1 | 2 | 3 | 4 | 5 |
|---|---|---|---|---|---|---|
| Tensile Strength, psi | | 16.7 ± 2.1 | 17.0 ± 2.8 | 23.9 ± 0.8 | 25.2 ± 2.6 | 27.1 ± 2.3 |
| Elongation at Break, % | | 106 ± 4 | 92 ± 4 | 119 ± 5 | 135 ± 2 | 129 ± 10 |
| Tear Strength, lbf/in, die C | | 2.8 ± 0.2 | 3.4 ± 0.2 | 3.3 ± 0.1 | 4.0 ± 0.2 | 5.1 ± 0.2 |
| Hysteresis, % | | 52.7 ± 1.1 | 47.3 ± 0.8 | 70.5 ± 1.1 | 72.2 ± 0.6 | 82.3 ± 1.6 |
| Properties Normalized to Density of 2.40 pcf | | | | | | |
| CFD @ 25% | | 0.29 | 0.22 | 0.32 | 0.46 | 0.58 |
| CFD @ 50% | | 0.53 | 0.46 | 0.59 | 0.83 | 1.06 |
| CFD @ 65% | | 1.03 | 0.88 | 1.06 | 1.47 | 2.07 |
| Tensile Strength, psi | | 16.70 | 20.40 | 30.51 | 30.70 | 29.70 |
| Tear Strength, lbf/in | | 2.8 | 4.08 | 4.21 | 4.87 | 5.59 |
| Apparent cell structure | | Uniform | Uniform | Uniform | Uniform | Uniform |

*Testing was carried out on foams prepared with 200 g of polyols in the formulation.

The foregoing detailed description and accompanying figures have been provided by way of explanation and illustration, and are not intended to limit the scope of the invention. Many variations in the present embodiments illustrated herein will be apparent to one of ordinary skill in the art, and remain within the scope of the invention and their equivalents. The skilled person in the art will recognize many variations that are within the spirit of the invention and scope of any current or future claims.

The invention claimed is:

1. A composition comprising a polyol, wherein the composition comprises the following polyols:

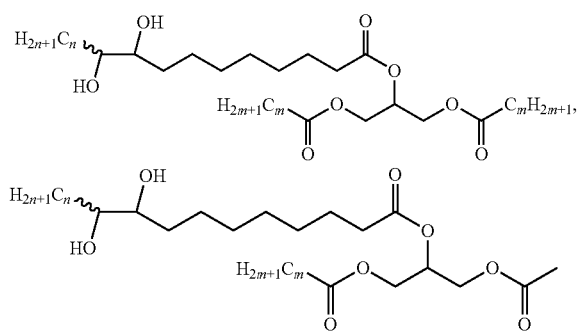

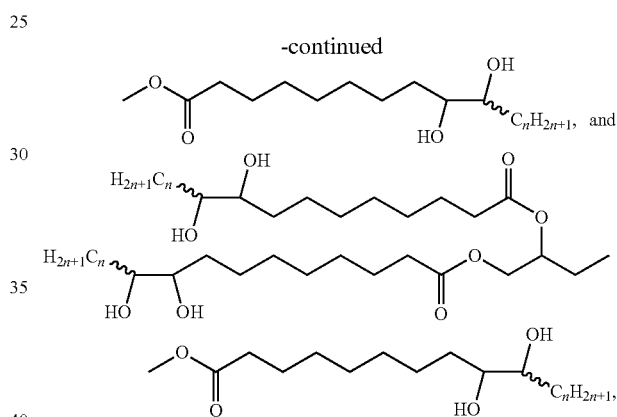

wherein:
n=1, 2, 3, 4, 5, 6, 7, 8, 9, 10, 11, or 12, and
m=11 to 20,
wherein the composition is prepared by a process comprising:
i) metathesizing palm oil to obtain palm oil metathesized triacylglycerides; and
ii) subjecting the palm oil metathesized triacylglycerides to epoxidation in a halogenated hydrocarbon solvent and subsequent hydroxylation.

2. The composition of claim 1, wherein the composition further comprises at least one polyol selected from the group consisting of the following structures:

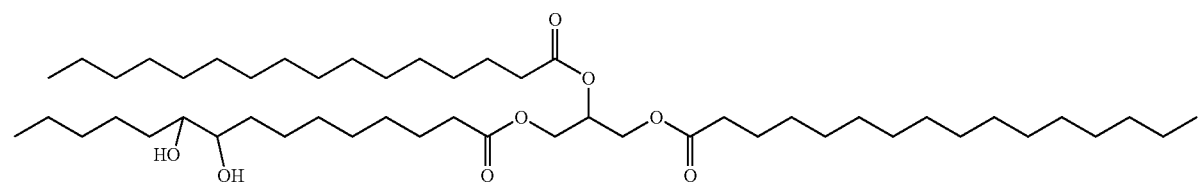

Chemical Formula: $C_{50}H_{96}O_8$
Exact Mass: 824.71
Molecular Weight: 825.29

-continued
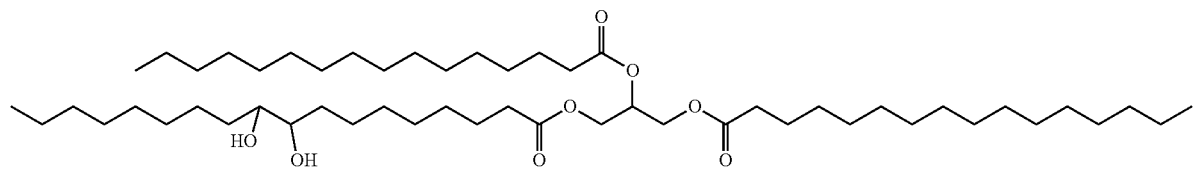
Chemical Formula: $C_{53}H_{102}O_8$
Exact Mass: 866.76
Molecular Weight: 867.37
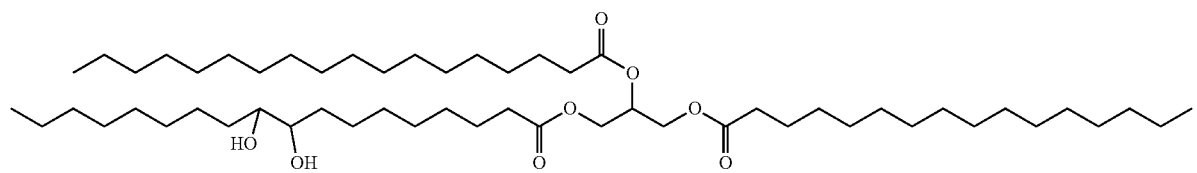
Chemical Formula: $C_{55}H_{106}O_8$
Exact Mass: 894.79
Molecular Weight: 895.43
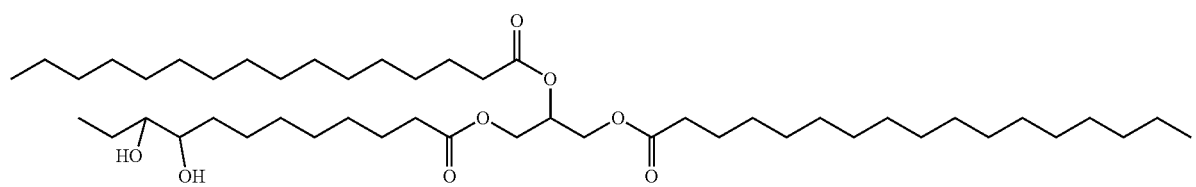
Chemical Formula: $C_{48}H_{92}O_8$
Exact Mass: 796.68
Molecular Weight: 797.24
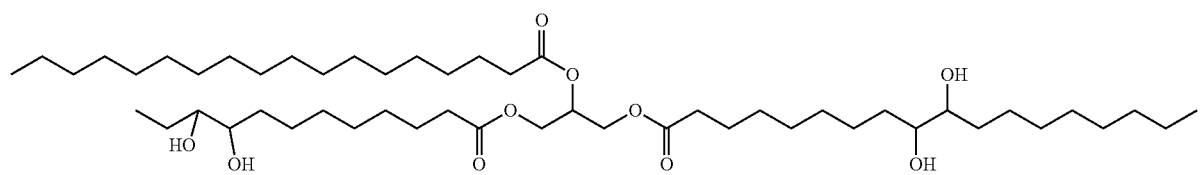
Chemical Formula: $C_{51}H_{98}O_{10}$
Exact Mass: 870.72
Molecular Weight: 871.32
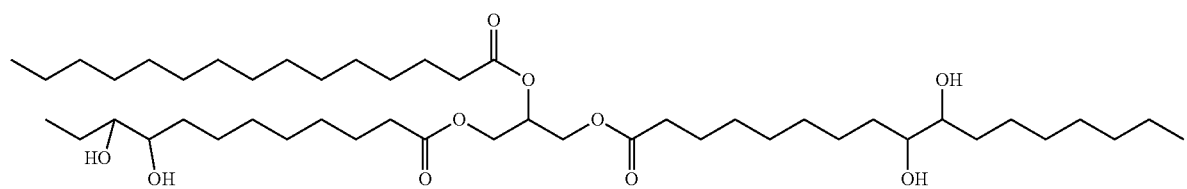
Chemical Formula: $C_{47}H_{90}O_{10}$
Exact Mass: 814.65
Molecular Weight: 815.21
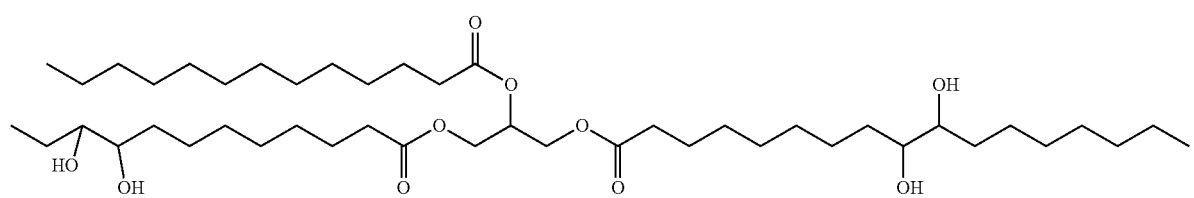
Chemical Formula: $C_{45}H_{86}O_{10}$
Exact Mass: 786.62
Molecular Weight: 787.16

-continued
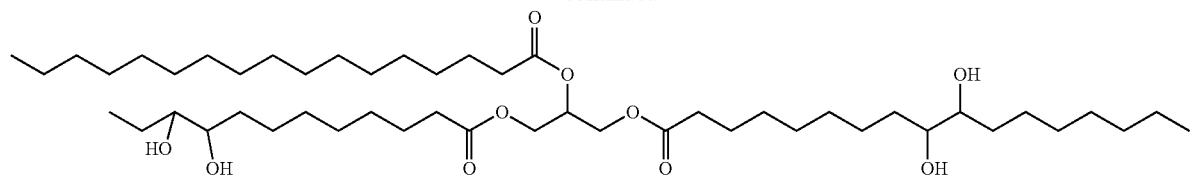
Chemical Formula: $C_{49}H_{94}O_{10}$
Exact Mass: 842.68
Molecular Weight: 843.26
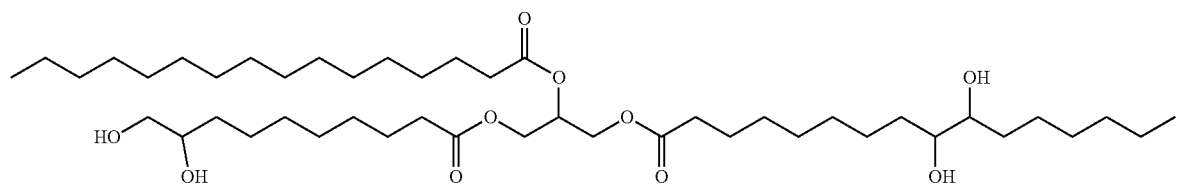
Chemical Formula: $C_{45}H_{86}O_{10}$
Exact Mass: 786.62
Molecular Weight: 787.16
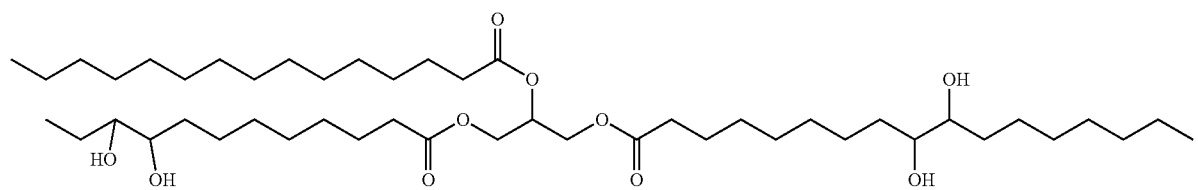
Chemical Formula: $C_{47}H_{90}O_{10}$
Exact Mass: 814.65
Molecular Weight: 815.21
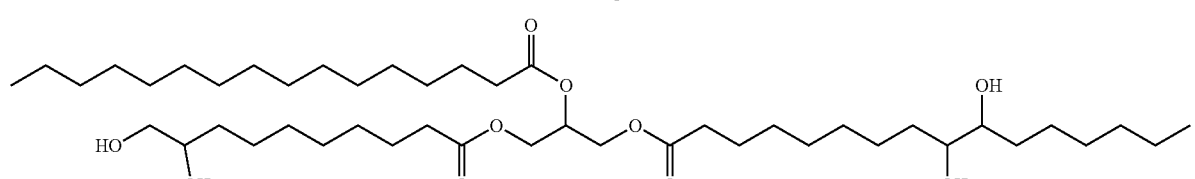
Chemical Formula: $C_{45}H_{86}O_{10}$
Exact Mass: 786.62
Molecular Weight: 787.16
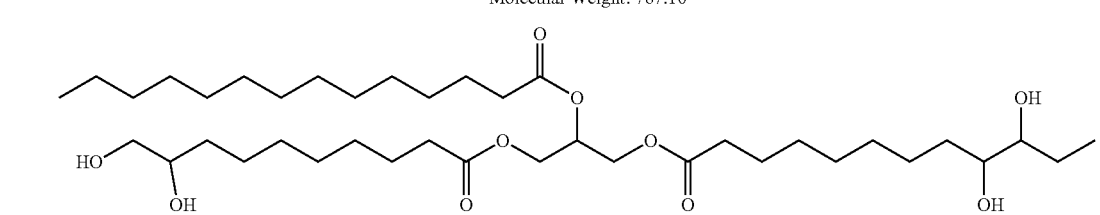
Chemical Formula: $C_{39}H_{74}O_{10}$
Exact Mass: 702.53
Molecular Weight: 703.00
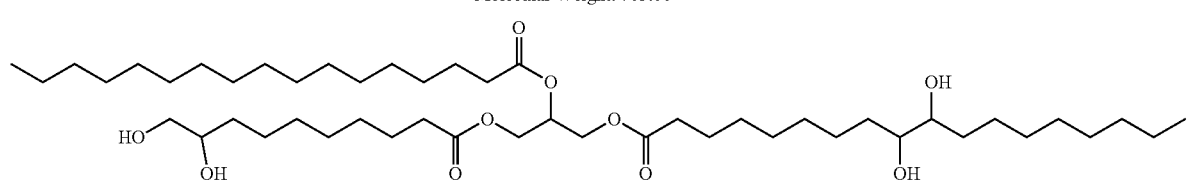
Chemical Formula: $C_{48}H_{92}O_{10}$
Exact Mass: 828.67
Molecular Weight: 829.24

-continued

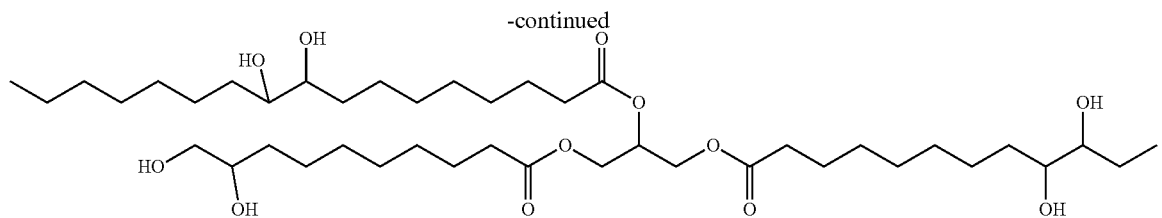

Chemical Formula: $C_{42}H_{80}O_{12}$
Exact Mass: 776.56
Molecular Weight: 777.08

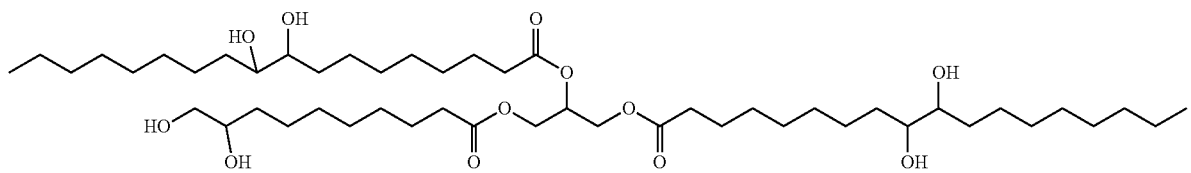

Chemical Formula: $C_{49}H_{94}O_{12}$
Exact Mass: 874.67
Molecular Weight: 875.26

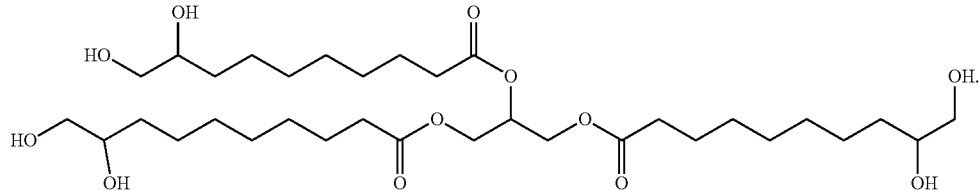

Chemical Formula: $C_{33}H_{62}O_{12}$
Exact Mass: 650.42
Molecular Weight: 650.84

3. The composition of claim 1, wherein the composition further comprises the following structures

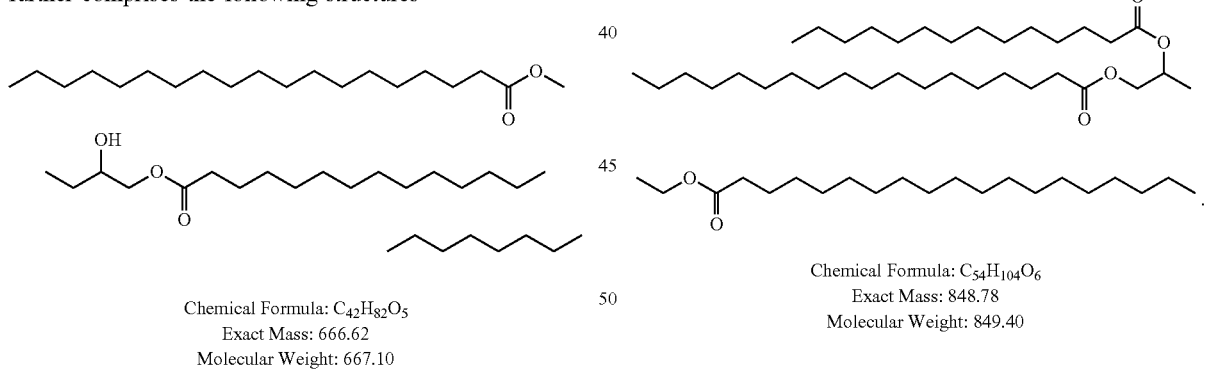

Chemical Formula: $C_{42}H_{82}O_5$
Exact Mass: 666.62
Molecular Weight: 667.10

Chemical Formula: $C_{61}H_{118}O_6$
Exact Mass: 946.89
Molecular Weight: 947.59

Chemical Formula: $C_{54}H_{104}O_6$
Exact Mass: 848.78
Molecular Weight: 849.40

4. The composition of claim 1, wherein n=2 or 8.

5. The composition of claim 1, wherein the halogenated hydrocarbon solvent is dichloromethane or chloroform.

6. The composition of claim 5, wherein the halogenated hydrocarbon solvent is dichloromethane.

7. The composition of claim 1, wherein the hydroxylation reaction is conducted in a mixture of water and tetrahydrofuran.

8. The composition of claim 7, wherein the hydroxylation reaction is performed in the presence of perchloric acid.

9. A flexible polyurethane foam prepared from a blend composition comprising:

(i) the polyol composition of claim 1;

(ii) at least one polyisocyanate component, wherein the ratio of hydroxy groups in the polyol composition to isocyanate groups in the at least one polyisocyanate component is less than 1;

(iii) at least one blowing agent;

(iv) at least one cell stabilizer component; and (v) at least one catalyst component.

10. The flexible polyurethane foam of claim 9, wherein the at least one polyisocyanate component comprises the formula $R(NCO)_n$, wherein n is 1 to 10, and wherein R is 2 to 40 carbon atoms, and wherein R contains at least one aliphatic, cyclic, alicyclic, aromatic, branched, aliphatic- and alicyclic-substituted aromatic, or aromatic-substituted aliphatic and alicyclic group.

11. The flexible polyurethane foam of claim 10, wherein the at least one polyisocyanate component comprises non-distilled diphenylmethane-4,4'-diisocyanate and the foam exhibits:

(1) a compressive strength for 10% deformation of 0.29 MPa to 0.96 MPa; and (2) a compressive strength for 25% deformation of 0.29 MPa to 1.41 MPa.

12. The flexible polyurethane foam of claim 10, wherein the at least one polyisocyanate component comprises non-distilled diphenylmethane-4,4'-diisocyanate and the foam exhibits:

(1) a compressive strength for 10% deformation of 0.29 MPa; and (2) a compressive strength for 25% deformation of 0.35 MPa.

13. The flexible polyurethane foam of claim 9, wherein:

(i) the blowing agent is selected from the group consisting of water, carbon dioxide, nitrogen gas, chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), hydrochlorfluoroolefins (HCFOs), acetone, and low-boiling hydrocarbons;

(ii) the cell stabilizer component comprises a silicone surfactant, and (iii) the catalyst component is selected from the group consisting of tertiary amines, organometallic derivatives or salts of bismuth, tin, iron, antimony, cobalt, thorium, aluminum, zinc, nickel, cerium, molybdenum, vanadium, copper, manganese and zirconium, metal carboxylates, metal hydroxides, and phosphines.

14. The flexible polyurethane foam of claim 9, wherein:

(i) the polyol composition is present in the blend composition in an amount of 100 parts by weight;

(ii) the ratio of hydroxy groups in the polyol composition to isocyanate groups in the at least one polyisocyanate component is 1:1.2;

(iii) the at least one blowing agent is present in the blend composition in an amount of 2 parts by weight;

(iv) the at least one cell stabilizer component is present in the blend composition in an amount of 2 parts by weight; and (v) the at least one catalyst component is present in the blend composition in an amount of 0.2 parts by weight.

15. A rigid polyurethane foam prepared from a blend composition comprising:

(i) the polyol composition of claim 1;

(ii) at least one polyisocyanate component, wherein the ratio of hydroxy groups in the polyol composition to isocyanate groups in the at least one polyisocyanate component is less than 1;

(iii) at least one cross-linking agent;

(iv) at least one blowing agent;

(v) at least one cell stabilizer component; and (vi) at least one catalyst component.

16. The rigid polyurethane foam of claim 15, wherein the at least one polyisocyanate component comprises the formula $R(NCO)_n$, wherein n is between 1 to 10, and wherein R is between 2 and 40 carbon atoms, and wherein R contains at least one aliphatic, cyclic, alicyclic, aromatic, branched, aliphatic- and alicyclic-substituted aromatic, or aromatic-substituted aliphatic and alicyclic group.

17. The composition rigid polyurethane foam of claim 15, wherein:

(i) the blowing agent is selected from the group consisting of water, carbon dioxide, nitrogen gas, chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), hydrochlorfluoroolefins (HCFOs), acetone, and low-boiling hydrocarbons;

(ii) the cell stabilizer component comprises a silicone surfactant, (iii) the catalyst component is selected from the group consisting of tertiary amines, organometallic derivatives or salts of bismuth, tin, iron, antimony, cobalt, thorium, aluminum, zinc, nickel, cerium, molybdenum, vanadium, copper, manganese and zirconium, metal carboxylates, metal hydroxides, and phosphines; and (iv) the cross-linking agent is selected from the group consisting of glycerin, diethanol amine, triethanol amine, trimethylol propane, and D-sorbitol.

18. The rigid polyurethane foam of claim 15, wherein the foam exhibits a compressive strength for 10% deformation of 0.30 MPa to 2.50 MPa.

19. The rigid polyurethane foam of claim 15, wherein:

(i) the polyol composition is present in the blend composition in an amount of 100 parts by weight;

(ii) the ratio of hydroxy groups in the polyol composition to isocyanate groups in the at least one polyisocyanate component is 1:1.2;

(iii) the at least one cross-linking agent is present in the blend composition in an amount of 18 parts by weight;

(iv) the at least one blowing agent is present in the blend composition in an amount of 2 parts by weight;

(v) the at least one cell stabilizer component is present in the blend composition in an amount of 2 parts by weight; and (vi) the at least one catalyst component is present in the blend composition in an amount of 2 parts by weight.

* * * * *